United States Patent
Balch et al.

(10) Patent No.: US 11,578,344 B2
(45) Date of Patent: *Feb. 14, 2023

(54) BIOSYNTHESIS OF RETINOIDS

(71) Applicant: DSM IP ASSETS B.V., Heerlen (NL)

(72) Inventors: Nathalie Balch, Kaiseraugst (CH); Paul Blomquist, Kaiseraugst (CH); Reed Doten, Kaiseraugst (CH); Peter Houston, Kaiseraugst (CH); Ethan Lam, Kaiseraugst (CH); Jenna McMahon, Kaiseraugst (CH); Joshua Trueheart, Kaiseraugst (CH); Celine Viarouge, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/647,730

(22) PCT Filed: Sep. 25, 2018

(86) PCT No.: PCT/EP2018/076033
§ 371 (c)(1),
(2) Date: Mar. 16, 2020

(87) PCT Pub. No.: WO2019/058000
PCT Pub. Date: Mar. 28, 2019

(65) Prior Publication Data
US 2020/0231993 A1    Jul. 23, 2020

Related U.S. Application Data

(60) Provisional application No. 62/562,712, filed on Sep. 25, 2017, provisional application No. 62/562,699, filed on Sep. 25, 2017, provisional application No. 62/562,672, filed on Sep. 25, 2017, provisional application No. 62/562,602, filed on Sep. 25, 2017.

(30) Foreign Application Priority Data

Apr. 20, 2018  (EP) ..................... 18168564
Jun. 5, 2018  (CH) ........................ 715/18

(51) Int. Cl.
*C12P 7/22* (2006.01)
*C12N 9/04* (2006.01)
*C12N 9/10* (2006.01)
*C12P 7/62* (2022.01)

(52) U.S. Cl.
CPC ............. *C12P 7/22* (2013.01); *C12N 9/0006* (2013.01); *C12N 9/1029* (2013.01); *C12P 7/62* (2013.01); *C12Y 101/01105* (2013.01); *C12Y 203/0102* (2013.01)

(58) Field of Classification Search
CPC ..... C12N 9/1029; C12N 9/0006; C12P 23/00; C12P 7/62; C12P 7/22; C12Y 203/01084; C12Y 101/01105; C12Y 203/0102; A61K 31/07

See application file for complete search history.

(56) References Cited

U.S. PATENT DOCUMENTS

| | | | | |
|---|---|---|---|---|
| 7,851,199 B2 * | 12/2010 | Bailey | ............... | A61P 3/00 |
| | | | | 435/254.2 |
| 8,691,555 B2 * | 4/2014 | Bailey | ............... | C12N 15/52 |
| | | | | 435/254.2 |
| 9,644,217 B2 * | 5/2017 | Kim | ............... | C12P 7/22 |
| 2003/0166595 A1 | 9/2003 | Von Lintig et al. | | |
| 2014/0170720 A1 | 6/2014 | Kim et al. | | |

FOREIGN PATENT DOCUMENTS

| | | |
|---|---|---|
| CN | 105339490 | 2/2016 |
| EP | 1031627 A1 | 8/2000 |
| JP | 2016-501543 | 1/2016 |
| WO | 2008042338 A2 | 4/2008 |
| WO | 2009/009142 A2 | 1/2009 |
| WO | 2009/126890 A2 | 10/2009 |
| WO | 2014/096992 | 6/2014 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chen et al., Molecular mechanisms of the coordination between astaxanthin and fatty acid biosynthesis in Haematococcus pluvialis (Chlorophyceae). The Plant J., 2015, vol. 81: 95-107. (Year: 2015).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Wikipedia, Acyl-CoA, 5 pages downloaded from https://en.wikipedia.org/wiki/Acyl-CoA on Jul. 23, 2021. (Year: 2021).*
ENZYME-2.3.1.84 Alcohol O-acetyltransferase, 2 pages downloaded from https://enzyme.expasy.org/ on Jul. 23, 2021 (Year: 2021).*
ENZYME-2.3.1.76 Retinol O-fatty-acyltransferase, 2 pages https://enzyme.expasy.org/ on Jul. 23, 2021 (Year: 2021).*
Menendez-Bravo et al., Metabolic engineering of microorganisms for the production of structurally diverse esters. Appl Microbiol Biotechnol., 2017, vol. 101: 3043-3053. (Year: 2017).*
Seffernick et al., Melamine deaminase and Atrazine chlorohydrolase: 98 percent identical but functionally different. J. Bacteriol., 2001, vol. 183 (8): 2405-2410. (Year: 2001).*

(Continued)

*Primary Examiner* — Ganapathirama Raghu
(74) *Attorney, Agent, or Firm* — Nixon & Vanderhye, PC

(57) ABSTRACT

The present invention is related to a novel enzymatic process for production of retinoids via a multi-step process, which process includes the use of heterologous enzymes having activity in a carotene-producing host cell, particularly wherein such process results in high percentage of retinoids, in trans-isoform.

17 Claims, No Drawings
Specification includes a Sequence Listing.

(56) References Cited

OTHER PUBLICATIONS

Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: 20120318, pp. 1-10. (Year: 2013).*
Verstrepen et al., Expression Levels of the Yeast Alcohol Acetyltransferase Genes ATF1, Lg-ATF1, and ATF2 Control the Formation of a Broad Range of Volatile Esters. Appl Environ. Microbiol., 2003, vol. 69(9): 5228-5237. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report for PCT/EP2018/076033, dated Nov. 22, 2018, 8 pages.
Written Opinion of the ISA for PCT/EP2018/076033, dated Nov. 22, 2018, 10 pages.
Bao-Jian Ding et al., "The Yeast ATF1 Acetyltransferase Efficiently Acetylates Insect Pheromone Alcohols: Implications for the Biological Production of Moth Pheromones", Lipids, vol. 51, No. 4, Jan. 22, 2016, pp. 469-475.
Hui-Jeong Jang, et al., "Retinoid production using metabolically engineered *Escherichia coil* with a two-phase culture system", Microbial Cell Factories 2011, 10:59, pp. 1-12.
Hui-Jeong Jang, et al., "Selective Retinol Production by Modulating the Composition of Retinoids From Metabolically Engineered *E. coli*", Biotechnology and Bioengineering, vol. 112, No. 8, Aug. 2015, 9 pages.
Alfonso Prado-Cabrero et al., "Retinal Biosynthesis in Fungi: Characterization of the Carotenoid Oxygenase CarX from Fusarium fujikuroi", Eukaryotic Cell, vol. 6, No. 4, Apr. 2007, pp. 650-657.
Unknown, Database UniProt, "SubName: Full=Oxidoreductase {ECO:0000313|EMBL:EXK27040.1}", XP002786088, 1 page, accessed on Oct. 25, 2018.
Unknown, Database UniProt, "SubName: Full=Alcohol acyl transferase {ECO:0000313|EMBL:AEM43830.1}", XP002786089, 1 page, accessed on Oct. 25, 2018.
Unknown, Database UniProt, "RecName: Full=Chloramphenicol acetyltransferase {ECO:0000256|RuleBase: RU000503}; EC=2.3.1.28 {ECO:0000256|RuleBase:RU000503}", XP002786090, 2 pages, accessed on Oct. 25, 2018.
Unknown, Database UniProt, "SubName: Full=1,2-diacyl-sn-glycerol:acetyl-CoA acetyltransferase {ECO:0000313|EMBL:ADF57327.1}", XP002786091, 1 page, accessed on Oct. 25, 2018.
Unknown, Database UniProt, "SubName: Full=Alcohol acyl transferase {ECO:0000313|EMBL:AAS79797.1}", XP002786092, 1 page, accessed on Oct. 25, 2018.
Unknown, Database UniProt, "SubName: Full=Coniferyl alcohol acyltransferase {ECO:0000313|EMBL:ABG75942.1}", XP002786093, 1 page, accessed on Oct. 26, 2018.
Unknown, Database UniProt, "SubName: Full=LAFE_0F18162g1_1 {ECO:0000313|EMBL:SCW02964.1}", XP002786094, 1 page, accessed on Oct. 26, 2018.
Unknown, Database UniProt, "SubName: Full=LAFE_0A06766g1_1 {ECO:0000313|EMBL:SCV99600.1}", XP002786095, 1 page, accessed on Oct. 26, 2018.
Unknown, Database UniProt, "SubName: Full=Putative carotenoid oxygenase {ECO:0000313|EMBL:CAH70723.1}", XP002786096, accessed on Dec. 17, 2018.
Unknown, Database UniProt, "RecName: Full=Zeaxanthin 7,8(7',8')—cleavage dioxygenase, chromoplastic; EC=1.13.11.84 {ECO:0000269|PubMed:12509521}; AltName: Full=CsZCD; AltName: Full=Zeaxanthin 7,8-dioxygenase; Flags: Precursor", XP002786097, 2 pages, accessed on Oct. 26, 2018.
Unknown, Database UniProt, "RecName: Full=Carotenoid isomerooxygenase; EC=1.13.11.65; AltName: Full=Beta-carotene 15,15'—monooxygenase and retinoid isomerase; AltName: Full=Beta-carotene dioxygenase and retinoid isomerase; AltName: Full=Neither inactivation nor afterpotential mutant B", XP002786098, dated Dec. 17, 2018.
Unknown, Database UniProt, "Beta,beta-carotene 15,15'—dioxygenase [Esox lucius]", XP002786099, 2 pages, accessed on Oct. 26, 2018.
International Search Report for PCT/EP2018/076032 dated Dec. 7, 2018, 7 pages.
Written Opinion of the ISA for PCT/EP2018/076032 dated Dec. 7, 2018, 9 pages.
Hong et al., "Biochemical properties of retinoid-converting enzymes and biotechnological production of retinoids", Applied Microbiology and Biotechnology, vol. 99, No. 19, Aug. 1, 2015, pp. 7813-7826.
Estrada et al., "Ustilago maydis accumulates β-carotene at levels determined by a retinal-forming carotenoid oxygenase", Fungal Genetics and Biology, vol. 46, 2009, pp. 803-813.
Unknown, Database UniProt [ONLINE], XP002786384, "Characterization of a gene in the car cluster of Fusarium fujikuroi that codes for a protein of the cartotenoid oxygenase family", Mar. 1, 2005, 1 page.
Unknown, Database UniProt [Online], XP002786385, "The complete DNA sequence of the mitochondrial genome of a 'living fossil,' the coelacanth (Latimeria chalumnae)", Apr. 18, 2012, 2 pages.
Unknown, Database UniProt [ONLINE], XP002786386, "Filing the gap in vitamin A research. Molecular identification of an enzyme cleaving beta-cartotene to retinal," Oct. 16, 2013, 4 pages.
Unknown, Database UniProt [ONLINE], XP002786387, Subname: Full-Zgc:63614 {ECO: 0000313 EMBL:AAH56789.1}, Jul. 5, 2004, 1 page.
Unknown, Database Protein [ONLINE], XP002786388, "beta, beta-carotene 15.15'-dioxygenase-like [Ictalurus punctatus]", Jul. 6, 2016, 1 page.
Unknown, Database Protein [ONLINE], "beta, beta-carotene 15, 15'-dioxygenase [Esox Lucius]", Jan. 30, 2017, 1 page.
S. Thewes et al., "Characterization of a gene in the *car* cluster of *Fusarium fujikuroi* that codes for a protein of the carotenoid oxygenase family", published Jul. 28, 2005, *Molecular Genetics and Genomics*, vol. 274, pp. 217-228.
Database Protein, "Beta-carotene oxygenase 1, like [Esox lucius]", Jan. 30, 2017, retrieved from NCBI Database accession No. XP_010867139.2, 1 page.
Database Uniprot, "SubName: Full=Beta-carotene oxygenase 1 {ECO:0000313|Ensembl:ENSLACP00000000167}", H2ZRZ6, submitted Feb. 2012, 2 pages.
Database Uniprot, "SubName: Full=Zgc:63614 {ECO:0000313|EMBL:AAH56789.1}", Q6PGY1; submitted Aug. 2003, 1 page.

* cited by examiner

BIOSYNTHESIS OF RETINOIDS

This application is the U.S. national phase of International Application No. PCT/EP2018/076033 filed 25 Sep. 2018, which designated the U.S. and claims priority to CH Patent Application No. 00715/18 filed 5 Jun. 2018, EP Patent Application No. 18168564.5 filed 20 Apr. 2018, and claims the benefit of U.S. Application No. 62/562,712 filed 25 Sep. 2017, U.S. Application No. 62/562,699 filed 25 Sep. 2017, U.S. Application No. 62/562,672 filed 25 Sep. 2017, and U.S. Application No. 62/562,602 filed 25 Sep. 2017, the entire contents of each of which are hereby incorporated by reference.

The present invention is related to a novel enzymatic process for production of retinoids via a multi-step process, which process includes the use of heterologous enzymes having activity in a carotene-producing host cell, particularly wherein such process results in high percentage of retinoids, in trans-isoform.

Retinoids, including vitamin A, are one of very important and indispensable nutrient factors for human beings which have to be supplied via nutrition. Retinoids promote well-being of humans, inter alia in respect of vision, the immune system and growth.

Current chemical production methods for retinoids, including vitamin A and precursors thereof, have some undesirable characteristics such as e.g. high-energy consumption, complicated purification steps and/or undesirable by-products. Therefore, over the past decades, other approaches to manufacture retinoids, including vitamin A and precursors thereof, including microbial conversion steps, which would be more economical as well as ecological, have been investigated.

In general, the biological systems that produce retinoids are industrially intractable and/or produce the compounds at such low levels that commercial scale isolation is not practicable. There are several reasons for this, including instability of the retinoids in such biological systems or the relatively high production of by-products.

Thus, it is an ongoing task to improve the product-specificity and/or productivity of the enzymatic conversion of beta-carotene into vitamin A. Particularly, it is desirable to optimize the productivity and selectivity of enzymes involved in conversion of precursors and/or intermediates.

Surprisingly, we now could identify a process for production of retinyl esters, particularly retinyl acetate, using a modified host organism, such as a carotenoid-producing host cell, particularly fungal host cell, comprising and expressing genes involved in the conversion of beta-carotene to retinyl acetate, with a total conversion of at least about 10% towards generation of retinol and with a percentage of trans-retinyl acetate of at least 65%.

In particular, the present invention is directed to a host cell, particularly a carotenoid-producing host cell, such as a fungal host cell, comprising (1) a stereoselective/trans-selective beta-carotene oxidase (BCO) catalyzing the conversion of beta-carotene to a retinal mix with a percentage of at least 65% present as trans-retinal, and (2) acetyl transferases (ATFs) catalyzing the conversion of retinol to a retinyl acetate mix with a total conversion of at least 10% of retinol acetylated into retinyl esters, particularly retinyl acetate and wherein the ATFs have a preference for acetylation of trans-retinol. Preferably, at least 80% of the retinyl esters are in the form of retinyl acetate, preferably as trans-retinyl acetate.

A carotenoid-producing host cell, particularly fungal host cell, according to the present invention is optionally furthermore comprising (3) (preferably heterologous) retinol dehydrogenase (RDH) which is capable of converting retinal into retinol, particularly with a total conversion of at least about 90% towards generation of retinol.

A carotenoid-producing host cell, particularly fungal host cell, according to the present invention is optionally furthermore comprising (4) a modification in the endogenous acyltransferase activity, i.e. activity towards acylating retinol into long chain retinyl esters, said modification leading to reduction or abolishment of said endogenous acyltransferase activity.

As used herein, the term "fungal host cell" includes particularly yeast as host cell, such as e.g. *Yarrowia* or *Saccharomyces*.

As used herein, the terms "stereoselective", "selective", "trans-selective" or "trans-isomer selective" enzyme with regards to BCO are used interchangeably herein. They refer to enzymes, i.e. BCOs as disclosed herein, with increased catalytic activity towards trans-isomers, i.e. increased activity towards catalysis of beta-carotene into trans-retinal. An enzyme according to the present invention is trans-specific, if the percentage of trans-isoforms, such as e.g. trans-retinal, is in the range of at least about 65% based on the total amounts of retinoids produced by such an enzyme or such carotene-producing host cell, particularly fungal host cell, comprising/expressing such enzyme.

As used herein, the terms "beta-carotene oxidizing enzyme", "beta-carotene oxygenase", "enzyme having beta-carotene oxidizing activity" or "BCO" are used interchangeably herein and refer to enzymes which are capable of catalyzing the conversion of beta-carotene into retinal in a trans-isomer selective way, leading to a retinal mix with at least about 65%, such as e.g. 68, 70, 75, 80, 85, 90, 95, 98% or up to 100%, of retinal in trans-isoform, based on the total amount of retinoids including retinal produced by said host cell.

Trans-selective BCOs as defined herein might be obtained from any source, such as e.g. plant, animal, bacteria, fungi, algae. Particular useful stereoselective BCOs are obtained from fungi, in particular Dikarya, including but not limited to fungi selected from Ascomycota or Basidiomycota, preferably obtained from *Fusarium* or *Ustilago*, more preferably isolated from *F. fujikuroi* or *U. maydis*, such as e.g. FfCarX (polypeptide sequence derived from AJ854252), UmCCO1 (polypeptide sequence derived from EAK81726). Furthermore, particularly useful stereoselective BCOs are obtained from insects, in particular Diptera, preferably obtained from *Drosophila*, more preferably from *D. melanogaster*, such as e.g. DmNinaB or DmBCO (polypeptide sequence derived from NP_650307.2). Furthermore, particularly useful stereoselective BCOs are obtained from plants, in particular Angiosperms, preferably obtained from *Crocus*, more preferably from *C. sativus*, such as e.g. CsZCO (polypeptide sequence derived from Q84K96.1). Furthermore, particularly useful stereoselective BCOs are obtained from eukaryotes, in particular pesces, preferably obtained from *Danio* or *Ictalurus*, more preferably from *D. rerio* or *I. punctatus*, such as e.g. DrBCO1, IpBCO (polypeptide sequence derived from XP_017333634).

Thus, in one aspect the present invention is directed to a carotenoid-producing host cell, particularly a fungal host cell, used for biosynthesis of retinoids including vitamin A, said host cell comprising a polypeptide with at least 60%, such as e.g. 65, 70, 75, 80, 85, 90, 95, 97, 98, 99% or up to 100% identity to a polypeptide known from the database selected from the group consisting of SEQ ID NOs:1, 3, 5, 7 or polynucleotides encoding such sequences, or a polypeptide with at least 50%, such as e.g. 55, 60, 65, 70, 75, 80, 85, 90, 93, 95, 97, 98, 99% or up to 100% identity to a polypeptide according to SEQ ID NOs:9, 11, 13, 15, 17 or polynucleotides encoding such sequences.

Besides the stereoselective BCO as described above, which is preferably heterologous expressed in the carotene-producing host cell, particularly fungal host cell, as defined herein, the host cell furthermore comprises (2) acetyl transferases (ATFs) catalyzing the conversion of retinol to a retinyl acetate mix with a total conversion of at least 10% of retinol acetylated into retinyl esters, particularly retinyl acetate and wherein the ATFs have a preference for acetylation of trans-retinol.

As used herein, the terms "acetyl transferase", "retinol acetylating enzyme", "enzyme having retinol acetylating activity" or "ATE" are used interchangeably herein and refer to enzymes [EC 2.3.1.84] which are capable of catalyzing the conversion of retinol into retinyl acetate with an amount of at least 80%, about 87, 90, 92, 95, 97, 99 or up to 100% of produced retinyl acetate in the trans-isoform. Said ATFs are capable of converting retinol, preferably trans-retinol, into retinyl ester, particularly retinyl acetate, with a total conversion of at least about 10%, preferably 12, 15, 20, 30, 40, 50, 80, 90 or even 100% (based on the total amount of retinoids within the retinoid mix produced by said host cell) towards generation of retinyl esters, e.g. retinyl acetate. A preferred isoform is ATF1.

ATFs as defined herein might be obtained from any source, such as e.g. plants, animals, including humans, algae, fungi, including yeast, or bacteria. Particular useful ATFs, preferably ATF1 enzymes, are obtained from yeast, in particular *Saccharomyces* or *Lachancea*, preferably obtained from *Saccharomyces bayanus*, such as e.g. SbATF1 (polypeptide sequence derived from AHX23958.1), *Lachancea mirantina* (LmATF1; SEQ ID NO:33), or *Lachancea fermentati* such as LfATF1 (polypeptide sequence derived from SCW02964.1) or LffATF1 polypeptide sequence derived from LT598487). Furthermore, particularly useful ATF1 enzymes are obtained from plants, including but not limited to plants selected from *Petunia, Euonymus, Malus*, or *Fragaria*, preferably obtained from *P. hybrida*, such as PhATF (polypeptide sequence derived from ABG75942.1), *E. alatus*, such as EaCAcT (polypeptide sequence derived from ADF57327.1), *M. domestica* (polypeptide sequence derived from AY517491) or *F. ananassa* (polypeptide sequence derived from AEM43830.1). Furthermore, particularly useful ATF1 enzymes are obtained from *Escherichia*, preferably *E. coli*, such as e.g. EcCAT (polypeptide sequence derived from EDS05563.1).

Thus, in one aspect the present invention is directed to a carotenoid-producing host cell, particularly a fungal host cell, used for biosynthesis of retinoids including vitamin A, said host cell comprising:

(1) a polypeptide with at least 60%, such as e.g. 65, 70, 75, 80, 85, 90, 95, 97, 98, 99% or up to 100% identity to a polypeptide selected from the group consisting of SEQ ID NOs:1, 3, 5 and 7 or a polypeptide with at least 50%, such as e.g. 55, 60, 65, 70, 75, 80, 85, 90, 93, 95, 97, 98, 99% or up to 100% identity to a polypeptide selected from SEQ ID NO:9, 11, 13, 15 or 17; and (2) a polypeptide with at least 60%, such as e.g. 65, 70, 75, 80, 85, 90, 92, 95, 97, 98, 99% or up to 100% identity to a polypeptide selected from the group consisting of SEQ ID NO:21, 23, 25, 27, 29, 31, 33, 36, or 38 as encoded by a polynucleotide including a nucleotide sequence according to SEQ ID NO:22, 24, 26, 28, 30, 32, 34, 35, 37 or 39.

According to an aspect of the present invention, the carotenoid-producing host cell comprising (1) stereoselective BCOs as defined herein and (2) trans-acting ATFs, preferably ATF1 enzymes, used in a process for production of retinyl acetate with a percentage of at least 80% present as trans-isoforms in the retinyl acetate mix, said host cell further comprising selective retinol dehydrogenases (RDHs) catalyzing the reduction of retinal into retinol with a total conversion of at least 90% towards production of retinol.

As used herein, the terms "retinal reductase", "retinol dehydrogenase", "enzyme having retinal reducing activity" or "RDH" are used interchangeably herein and refer to enzymes [EC 1.1.1.105] which nearly exclusively (90% or more) are capable of catalyzing the conversion of retinal into retinol, i.e. which are capable of catalyzing the conversion of retinal to retinol with a total conversion of at least about 90%, preferably 92, 95, 97, 98, 99 or even 100% towards retinol formation.

For the purpose of the present invention, any retinal reducing enzyme which results in an increase of at least about 18%, such as e.g. at least about 20, 30, 40, 50, 60, 70, 80, 90, 100% towards formation of retinol can be used in a process as defined herein, such increase being calculated on the retinol formation using endogenous RDHs present in suitable carotenoid-producing host cells, particularly fungal host cells, such as e.g. strains of *Yarrowia* or *Saccharomyces*.

RDHs with activity towards retinol formation, i.e. retinal reduction reaction, as defined herein might be obtained from any source, such as e.g. plants, animals, including humans, algae, fungi, including yeast, or bacteria. Particular useful RDHs are obtained from fungi, in particular Dikarya, including but not limited to fungi selected from Ascomycota, preferably obtained from *Fusarium*, more preferably isolated from *F. fujikuroi*, such as e.g. FfRDH12 (SEQ ID NO:19).

Thus, in a further aspect the present invention is directed to a carotenoid-producing host cell, particularly a fungal host cell, used for biosynthesis of retinoids including vitamin A, said host cell comprising:

(1) a polypeptide with at least 60%, such as e.g. 65, 70, 75, 80, 85, 90, 95, 97, 98, 99% or up to 100% identity to a polypeptide selected from the group consisting of SEQ ID NOs:1, 3, 5 and 7 or a polypeptide with at least 50%, such as e.g. 55, 60, 65, 70, 75, 80, 85, 90, 93, 95, 97, 98, 99% or up to 100% identity to a polypeptide selected from SEQ ID NO:9, 11, 13, 15 or 17;

(2) a polypeptide with at least 60%, such as e.g. 65, 70, 75, 80, 85, 90, 92, 95, 97, 98, 99% or up to 100% identity to a polypeptide selected from the group consisting of SEQ ID NO:21, 23, 25, 27, 29, 31, 33, 36, or 38 as encoded by a polynucleotide including a nucleotide sequence according to SEQ ID NO:22, 24, 26, 28, 30, 32, 34, 35, 37 or 39; and (3) a polypeptide with at least 60%, such as e.g. 65, 70, 75, 80, 85, 90, 95, 97, 98, 99% or up to 100% identity to a polypeptide according to SEQ ID NO:19, encoded by a polynucleotide including a nucleic acid sequence according to SEQ ID NO:20.

According to another aspect of the present invention, the carotenoid-producing host cell according to the present invention is used in a process for production of retinyl acetate with a percentage of at least 65% present as trans-isoforms, said host cell comprising (1) stereoselective or trans-selective BCOs as defined herein, (2) ATFs as defined herein, such as ATF1, with preference for acetylation of trans-retinol, (3) RDHs with about 90% or more activity towards formation of retinol via reduction of retinal, optionally further comprising modifications in the endogenous acyltransferase activity, such as reduced or abolished endogenous activity towards acylating retinol into long chain retinyl esters.

As used herein, the terms "acyltransferase", "retinol acylating enzyme", "enzyme having retinol acylating activity" are used interchangeable herein and refer to enzymes which are capable of catalyzing the conversion of retinol into long chain retinyl esters. Suitable acylating enzymes might be selected from acyl-CoA:diacylglycerol acyltransferase family members [EC 2.3.1], including but not limited to DGATs [EC 2.3.1.20] such as e.g. DGAT1 or DGAT2, ARATs, mdy.

Thus, in one embodiment the present invention is directed to a carotenoid-producing host cell, particularly a fungal host cell, used for biosynthesis of retinoids including vitamin A, said host cell comprising:

(1) a polypeptide with at least 60%, such as e.g. 65, 70, 75, 80, 85, 90, 95, 97, 98, 99% or up to 100% identity to a polypeptide selected from the group consisting of SEQ ID NOs:1, 3, 5 and 7 or a polypeptide with at least 50%, such as e.g. 55, 60, 65, 70, 75, 80, 85, 90, 93, 95, 97, 98, 99% or up to 100% identity to a polypeptide selected from SEQ ID NO:9, 11, 13, 15 or 17;

(2) a polypeptide with at least 60%, such as e.g. 65, 70, 75, 80, 85, 90, 92, 95, 97, 98, 99% or up to 100% identity to a polypeptide selected from the group consisting of SEQ ID NO:21, 23, 25, 27, 29, 31, 33, 36, or 38 as encoded by a polynucleotide including a nucleotide sequence according to SEQ ID NO:22, 24, 26, 28, 30, 32, 34, 35, 37 or 39;

(3) a polypeptide with at least 60%, such as e.g. 65, 70, 75, 80, 85, 90, 95, 97, 98, 99% or up to 100% identity to a polypeptide according to SEQ ID NO:19, encoded by a polynucleotide including a nucleic acid sequence according to SEQ ID NO:20; and (4) reduced or abolished activity of a polypeptide having acyltransferase activity catalyzing the acetylation of retinol into long chain retinyl esters, such as DGATs [EC 2.3.1.20].

Modification with regards to acylation activity in a process for production of retinoids using the carotenoid-producing host cell, particularly fungal host cell, as defined herein, means a reduction or abolishment of the endogenous gene(s) encoding acyltransferase activity, such that the activity of endogenous acyltransferases is reduced or abolished, preferably abolished, said host cell being capable or used for production of a retinyl acetate mix comprising at least about 65% in trans-isoform compared to a host cell expressing the respective endogenous acyltransferases prior to the modification of the host cell, i.e. wherein the endogenous acyltransferases are still active. When using said host cell in a vitamin A production process, the percentage of trans-isoforms, such as trans-retinyl acetate, can be increased to about 65% or more, preferably such as 68, 70, 75, 80, 85, 90, 95, 98 or up to 100% based on the total amount of retinyl esters.

Reduction or abolishment of endogenous gene/protein activity, such as retinol acyltransferase activity, might be achieved by, e.g. introducing mutation(s) into the endogenous gene(s) coding for enzymes having said activity, such as acyltransferase activity. The skilled person knows how to genetically manipulate a host cell as defined herein resulting in reduction or abolishment of such activity, e.g. acyltransferase activity. These genetic manipulations include, but are not limited to, e.g. gene replacement, gene amplification, gene disruption, transfection, transformation using plasmids, viruses, or other vectors.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

Modifications in order to have the host cell as defined herein produce less or no copies of genes and/or proteins, such as e.g. acylating enzymes as defined herein, i.e. to have less or no acyltransferase activity, may include the use of weak promoters, or the mutation (e.g. insertion, deletion or point mutation) of (parts or) the respective enzymes (as described herein), in particular its regulatory elements. An example of such a genetic manipulation may for instance affect the interaction with DNA that is mediated by the N-terminal region of enzymes as defined herein or interaction with other effector molecules. In particular, modifications leading to reduced or abolished specific enzyme activity may be carried out in functional, such as functional for the catalytic activity, parts of the proteins. Furthermore, reduction or abolishment of enzyme specific activity might be achieved by contacting said enzymes with specific inhibitors or other substances that specifically interact with them. In order to identify such inhibitors, the respective enzymes, such as e.g. the acylating enzymes as defined herein, may be expressed and tested for activity in the presence of compounds suspected to inhibit their activity.

Modifications in order to have the host cell as defined herein produce more copies of genes and/or proteins, such as e.g. stereoselective BCOs, (trans-acting) ATFs and/or RDHs with selectivity towards formation of retinol as defined herein, may include the use of strong promoters, suitable transcriptional- and/or translational enhancers, or the introduction of one or more gene copies into the carotenoid-producing host cell, particularly fungal host cell, leading to increased accumulation of the respective enzymes in a given time. The skilled person knows which techniques to use in dependence of the host cell. The increase or reduction of gene expression can be measured by various methods, such as e.g. Northern, Southern or Western blot technology as known in the art.

The terms "conversion", "oxidation", "reduction", "acylation", "acetylation" in connection with enzymatic catalysis of enzymes as defined herein are art-recognized and refer to actions of the enzymes towards formation/production of retinoids, in particular retinyl acetate.

Preferably, the enzymes used in a process for production of retinoids, in particular retinyl acetate as defined herein, are expressed as heterologous enzymes. They might be integrated on suitable expression vectors or might be integrated in the chromosomal DNA. Such carotenoid-producing host cell, particularly fungal host cell, comprising a heterologous polynucleotide either on an expression vector or integrated into the chromosomal DNA of the host cell encoding enzymes involved in retinoid production, in particular production of retinyl acetate as described herein, is called a recombinant host cell.

In one particular aspect, the present invention is related to a carotenoid-producing host cell, particularly fungal host cell, carrying one or more (genetic) modifications as defined herein, to be used in a process for production of retinoids, in particular retinyl acetate with at least about 65-90% of the retinyl acetate in trans-isoform and wherein the percentage of acetylated retinol forms, i.e. retinyl esters, such as retinyl acetate, is about at least 10% based on the total amount of retinoids produced by said host cell.

According to another aspect of the present invention, the amount of extracellular retinoids produced with a carotenoid-producing host cell as defined herein can be increased, in particular using a carotenoid-producing host cell which is selected from fungi including yeast, such as e.g. *Yarrowia* or *Saccharomyces*. Thus, a process as described herein leads to at least 80% of retinoids exported outside of the cell, such as e.g. 85, 90, 92, 95, 98, 99 or up to 100% of the retinoids, in particular retinyl acetate with preferably a percentage of about at least 80% in trans-isoform. This is in particular useful with regards to further isolation and purification steps.

Suitable carotenoid-producing host cells used for the process as described herein might be selected from any (micro)organisms, which is suitable for carotenoid/retinoid production and which allows expression of the nucleic acids encoding one of the enzymes as disclosed herein, including functional equivalents or derivatives as described herein. Examples of suitable carotenoid/retinoid-producing host (micro)organisms are bacteria, algae, fungi, including yeasts, plant or animal cells. Preferred bacteria are those of the genera *Escherichia*, such as, for example, *Escherichia coli, Streptomyces, Pantoea* (*Erwinia*), *Bacillus, Flavobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis, Paracoccus*, such as, for example, *Paracoccus zeaxanthinifaciens*. Preferred eukaryotic microorganisms, in particular fungi including yeast, are selected from *Saccharomyces*, such as *Saccharomyces cerevisiae, Aspergillus*, such as *Aspergillus niger, Pichia*, such as *Pichia pastoris, Hansenula*, such as *Hansenula polymorpha, Phycomyces*, such as *Phycomyces blakesleanus, Mucor, Rhodotorula, Sporobolomyces, Xanthophyllomyces, Phaffia, Blakeslea*, such as e.g. *Blakeslea trispora*, or *Yarrowia*, such as *Yarrowia lipolytica*. In particularly preferred is expression in a fungal host cell, such as e.g. *Yarrowia* or *Saccharomyces*, or expression in *Escherichia*, more preferably expression in *Yarrowia lipolytica* or *Saccharomyces cerevisiae*.

With regards to the present invention, it is understood that organisms, such as e.g. microorganisms, fungi, algae, or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain *Lachancea mirantina* is a synonym of strain *Zygosaccharomyces* sp. IFO 11066, originated from Japan.

Depending on the host cell, the polynucleotides as defined herein, such as e.g. the polynucleotides encoding BCOs, RDHs, ATFs as defined herein, might be optimized for expression in the respective host cell. The skilled person knows how to generate such modified polynucleotides. It is understood that the polynucleotides as defined herein also encompass such host-optimized nucleic acid molecules as long as they still express the polypeptide with the respective activities as defined herein.

Thus, in one embodiment, the present invention is directed to a carotenoid-producing host cell, particularly fungal host cell, comprising polynucleotides encoding BCOs, ATFs, and/or RDHs as defined herein which are optimized for expression in said host cell, with no impact on growth of expression pattern of the host cell or the enzymes. Particularly, a carotenoid-producing host cell is selected from *Yarrowia*, such as *Yarrowia lipolytica*, comprising optimized polynucleotide sequences selected from the group consisting of SEQ ID NOs: 2, 4, 6, 8, 10, 12, 14, 16, 18, 20, 22, 24, 26, 28, 30, 32, 35, 37 and 39 or sequences with at least 60%, such as e.g. 65, 70, 75, 80, 85, 90, 92, 95, 97, 98, 99% or up to 100% identity thereto.

The present invention is directed to a process for production of a retinyl ester mix comprising retinyl acetate, preferably with a percentage of at least 65% a trans-retinyl acetate, via enzymatic activity of (1) stereospecific BCO as defined herein, comprising contacting beta-carotene with said BCO leading to a retinal mix with a percentage of at least 65%, such as e.g. at least 65-90%, of trans-retinal, and (2) one of the Atf1 enzymes as defined herein, comprising contacting retinol, preferably trans-retinol or a retinol mix with at least 65-90% in trans-isoform, with said Atf1 enzyme. Particularly, the invention is directed to a process for production of vitamin A, said process comprising (a) introducing a nucleic acid molecule encoding (1) one of the stereoselective BCO enzymes as defined herein and (2) one of the Atf1 enzymes as defined herein into a suitable carotenoid-producing host cell, particularly fungal host cell, as defined herein, (b) enzymatic conversion of beta-carotene into retinal, with at least about 65% of trans-retinal, enzymatic conversion, i.e. acetylation, of retinol, preferably with a percentage of at least 65-90% of trans-retinol, via action of said expressed Atf1 into a mix of trans- and cis-retinyl acetate, and (3) conversion of said retinyl acetate into vitamin A under suitable conditions known to the skilled person.

The terms "sequence identity", "% identity" or "sequence homology" are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person knows plant-derived enzymes might contain a chloroplast targeting signal which is to be cleaved via specific enzymes, such as e.g. chloroplast processing enzymes (CPEs).

The enzymes as defined herein also encompasses enzymes carrying amino acid substitution(s) which do not alter enzyme activity, i.e. which show the same properties with respect to the wild-type enzyme and catalyze the conversion of beta-carotene to retinal, retinal to retinol, retinol to retinyl acetate, in particular with a total conversion of at least about 65%, such as e.g. at least about 65-90%, towards production of trans-isoform of retinyl acetate. Such mutations are also called "silent mutations", which do not alter the (enzymatic) activity of the enzymes as described herein.

A nucleic acid molecule according to the invention may comprise only a portion or a fragment of the nucleic acid sequence provided by the present invention, for example a fragment which may be used as a probe or primer or a fragment encoding a portion of an enzyme as defined herein. The nucleotide sequence determined from the cloning of the genes encoding the BCOs, ATFs and/or RDHs as defined herein allows for the generation of probes and primers designed for use in identifying and/or cloning other homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequences described herein.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The carotenoid-producing host cell, particularly fungal host cell, as defined herein, which is able to express beta-carotene producing genes, the beta-carotene oxidases as described herein, the retinol acetylating enzymes as defined herein, the retinal reducing enzymes as defined herein, and/or optionally further genes required for biosynthesis of vitamin A, may be cultured in an aqueous medium supplemented with appropriate nutrients under aerobic or anaerobic conditions and as known by the skilled person for the different host cells. Optionally, such cultivation is in the presence of proteins and/or co-factors involved in transfer of electrons, as defined herein. The cultivation/growth of the host cell may be conducted in batch, fed-batch, semi-continuous or continuous mode. Depending on the host cell, preferably, production of retinoids such as e.g. vitamin A and precursors such as retinal, retinol can vary, as it is known to the skilled person. Cultivation and isolation of beta-carotene and retinoid-producing host cells selected from *Yarrowia* is described in e.g. WO2008042338. With regards to production of retinoids in host cells selected from *E. coli*, methods are described in e.g. Jang et al, Microbial Cell Factories, 10:95 (2011). Specific methods for production of beta-carotene and retinoids in yeast host cells, such as e.g. *Saccharomyces cerevisiae*, are disclosed in e.g. WO2014096992.

The present invention is directed to a process for production of retinoids, in particular retinyl acetate with at least about 65% present in trans-isoform and a percentage of at least about 10% in acetylated form, i.e. as retinyl acetate based on the total amount of retinoids produced by the respective host cell, in a carotenoid-producing host cell under conditions as described herein. The produced retinoids, in particular retinyl acetate might be isolated and optionally further purified from the medium and/or host cell.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a system in the presence of a suitable substrate. The skilled person knows how to measure enzyme activity, in particular activity of BCOs, RDHs or ATFs as defined herein. Analytical methods to evaluate the capability of a suitable enzyme as defined herein for retinoid production are known in the art, such as e.g. described in Example 4 of WO2014096992. In brief, titers of products retinoids and carotenoids and the like can be measured by HPLC.

As used herein, a carotenoid-producing host cell, particularly fungal host cell, is a host cell, wherein the respective polypeptides are expressed and active in vivo leading to production of carotenoids, e.g. beta-carotene. The genes and methods to generate carotenoid-producing host cells are known in the art, see e.g. WO2006102342. Depending on the carotenoid to be produced, different genes might be involved.

As used herein, a retinoid-producing host cell, particularly fungal host cell, is a host cell wherein, the respective polypeptides are expressed and active in vivo, leading to production of retinoids, e.g. vitamin A and its precursors, via enzymatic conversion of beta-carotene via retinal, retinol and retinyl acetate. These polypeptides include the BCOs, RDHs and ATFs as defined herein. The genes of the vitamin A pathway and methods to generate retinoid-producing host cells are known in the art. Preferably, the beta-carotene is converted into retinal via action of beta-carotene oxidizing enzymes, the retinal is further converted into retinol via action of RDHs as defined herein, and the retinol, preferably trans-retinol, is converted into retinol acetate via action of acetyltransferase enzymes, such as e.g. ATF1. The retinol acetate might be the retinoid of choice which is isolated from the host cell.

Retinoids as used herein include beta carotene cleavage products also known as apocarotenoids, including but not limited to retinal, retinolic acid, retinol, retinoic methoxide, retinyl acetate, retinyl esters, 4-keto-retinoids, 3 hydroxy-retinoids or combinations thereof. Long chain retinyl esters as used herein define hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to linoleic acid, oleic acid or palmitic acid. Biosynthesis of retinoids is described in e.g. WO2008042338.

Retinal as used herein is known under IUPAC name (2E,4E,6E,8E)-3,7-Dimethyl-9-(2,6,6-trimethylcyclohexen-1-yl)nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

Vitamin A as used herein may be any chemical form of vitamin A found in aqueous solutions, such as for instance undissociated, in its free acid form or dissociated as an anion. The term as used herein includes all precursors or intermediates in the biotechnological vitamin A pathway. It also includes vitamin A acetate.

In particular, the present invention features the present embodiments:

A carotenoid-producing host cell, particularly fungal host cell, comprising:
(a) stereoselective beta-carotene oxidizing enzyme (BCO), said host cell producing a retinal mix comprising cis- and trans-retinal, wherein the percentage of trans-retinal in the mix is at least about 65%, preferably 68, 70, 75, 80, 85, 90, 95, 98% or up to 100% produced by said host cell; and
(b) an acetyl transferase (ATF) [EC 2.3.1.84], preferably an enzyme with acetyl transferase 1 (Atf1) activity, said enzyme catalyzing the conversion of retinol, preferably trans-retinol, to a retinyl acetate mix, with a percentage of at least 10% of acetylated retinol, i.e. retinyl acetate, based on the total amount of retinoids produced by said host cell.

A carotenoid-producing host cell, particularly fungal host cell, as above and defined herein, wherein the acetyl transferase [EC 2.3.1.84], preferably an enzyme with acetyl transferase 1 activity, catalyzes the conversion of retinol to a retinyl acetate mix, wherein the mix comprises at least about 65%, preferably 68, 70, 75, 80, 85, 90, 95, 98% or up to 100% retinyl acetate, such as e.g. at least 65-90% retinyl acetate, in trans-isoform.

The carotenoid-producing host cell, particularly fungal host cell, as above and defined herein, further comprising a (preferably heterologous) retinol dehydrogenase (RDH) [EC 1.1.1.105] capable of converting retinal into retinol with a total conversion of at least about 90% towards generation of retinol, preferably RDH obtained from fungi, in particular Dikarya, including but not limited to fungi selected from Ascomycota, more preferably obtained from *Fusarium*, even more preferably isolated from *F. fujikuroi*, such as a polypeptide with at least about 60% identity to FfRDH12 (SEQ ID NO:19).

The carotenoid-producing host cell, particularly fungal host cell, as above and defined herein, furthermore comprising a modification in the endogenous acyltransferase activity, wherein the endogenous acyltransferase activity, preferably [EC 2.3.1] activity, more preferably acyltransferase [EC 2.3.1.20] activity, has been reduced or abolished.

The carotenoid-producing host cell, particularly fungal host cell, as above and defined herein, wherein the BCO is selected from fungi, plants or animal, preferably selected from *Fusarium, Ustilago, Crocus, Drosophila, Danio, Ictalurus, Esox, Latimeria*, more preferably selected from *Fusarium fujikuroi, Ustilago maydis, Crocus sativus, Drosophila melanogaster, Danio rerio, Ictalurus punctatus, Esox lucius, Latimeria chalumnae* even more preferably selected from a polypeptide with at least about 60% identity to a polypeptide according to SEQ ID NOs:1, 3, 5 or 7 or a polypeptide with at least about 50% identity to a polypeptide sequence according to SEQ ID NOs:9, 11, 13, 15 or 17.

The carotenoid-producing host cell, particularly fungal host cell, as above and defined herein, wherein the acetyl transferase, preferably Atf1, is selected from plants, animals, including humans, algae, fungi, including yeast or bacteria, preferably selected from *Saccharomyces, Fragaria, Escherichia, Euonymus, Malus, Petunia* or *Lachancea*, more preferably selected from *Saccharomyces bayanus, Fragaria ananassa, Escherichia coli, Euonymus alatus, Malus domestica, Petunia hybrida, Lachancea mirantina* or *Lachancea fermentati*, even more preferably selected from a polypeptide with at least about 60% identity to a polypeptide according to SEQ ID NOs:21, 23, 25, 27, 29, 31, 33, 36, or 38.

The carotenoid-producing host cell, particularly fungal host cell, as above and defined herein, producing a retinyl acetate mix comprising at least about 65%, preferably 68, 70, 75, 80, 85, 90, 95, 98% or up to 100% trans-retinyl acetate isoform, such as at least 65-90% trans-retinyl acetate isoform.

The carotenoid-producing host cell as above and defined herein, wherein the host cell is selected from plants, fungi, algae or microorganisms, preferably selected from fungi including yeast, more preferably from *Saccharomyces, Aspergillus, Pichia, Hansenula, Phycomyces, Mucor, Rhodotorula, Sporobolomyces, Xanthophyllomyces, Phaffia, Blakeslea* or *Yarrowia*, even more preferably from *Yarrowia lipolytica* or *Saccharomyces cerevisiae*.

The carotenoid-producing host cell as above and defined herein, wherein the host cell is selected from plants, fungi, algae or microorganisms, preferably selected from *Escherichia, Streptomyces, Pantoea, Bacillus, Flavobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis* or *Paracoccus*.

The carotenoid-producing host cell, particularly fungal host cell, as above and defined herein used in a process for conversion of beta-carotene into vitamin A.

A process for production of trans-retinyl acetate comprising cultivation of the carotenoid-producing host cell, particularly fungal host cell, as above and defined herein in an aqueous medium under suitable culture conditions and isolating and optionally further purifying said trans-retinyl acetate from the medium and/or host cell.

A process for production of vitamin A comprising the steps of:

(a) introducing a nucleic acid molecule encoding stereo-selective BCO as defined herein, acetyl transferase [EC 2.3.1.84] as defined herein, optionally retinol dehydrogenase [EC 1.1.1.105] as defined herein, into a suitable carotene-producing host cell, particularly fungal host cell;

(b) optionally reducing or abolishing the endogenous acyltransferase activity [EC 2.3.1] as defined herein of the cell of (a), (c) enzymatic conversion of beta-carotene into retinyl acetate mix comprising a ratio of trans to cis-retinyl acetate of 4; and (d) conversion of retinyl acetate into vitamin A under suitable culture conditions.

A process for production of vitamin A comprising the steps of:

(a) introducing a nucleic acid molecule encoding stereo-selective BCO, acetyl transferase [EC 2.3.1.84], optionally retinol dehydrogenase [EC 1.1.1.105], into a suitable host cell;

(b) optionally reducing or abolishing the endogenous acyltransferase activity [EC 2.3.1] of the cell of (a), (c) enzymatic conversion of beta-carotene into retinoids comprising at least a percentage of 10% retinyl acetate, said retinyl acetates comprising at least a percentage of 65% in trans isoform based on the total amount of produced retinoids; and (d) conversion of retinyl acetate into vitamin A under suitable culture conditions.

The following examples are illustrative only and are not intended to limit the scope of the invention in any way. The contents of all references, patent applications, patents, and published patent applications, cited throughout this application are hereby incorporated by reference, in particular WO2006102342, WO2008042338 or WO2014096992.

EXAMPLES

Example 1: General Methods, Strains, and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake Plate Assay.

Typically, 800 µl of 0.075% Yeast extract, 0.25% peptone (0.25×YP) is inoculated with 10 µl of freshly grown *Yarrowia* and overlaid with 800 µl of mineral oil (Drakeol 5, Penreco Personal Care Products, Karns City, Pa., USA) carbon source 5% corn oil in mineral oil and/or 5% in glucose in aqueous phase. Transformants were grown in 24 well plates (Microplate Devices 24 Deep Well Plates Whatman 7701-5102), covered with mat seal (Analytical Sales and Services Inc. Plate Mats 24010CM), sterile sealed with Qiagen Airpore Tape Sheets (19571) and shaken in Infors multi plate shaker (Multitron), 30° C., 800 RPM in YPD media with for 4 days. The mineral oil fraction was removed from the shake plate wells and analyzed by HPLC on a normal phase column, with a photo-diode array detector. This method is used in Examples 2, 3, 4.

DNA Transformation.

Strains are transformed by overnight growth on YPD plate media 50 µl of cells is scraped from a plate and transformed by incubation in 500 µl with 1 µg transforming DNA, typically linear DNA for integrative transformation, 40% PEG 3550 MW, 100 mM lithium acetate, 50 mM Dithiothreitol, 5 mM Tris-Cl pH 8.0, 0.5 mM EDTA for 60 minutes at 40° C. and plated directly to selective media or in the case of dominant antibiotic marker selection the cells are out grown on YPD liquid media for 4 hours at 30° C. before plating on the selective media.

DNA Molecular Biology.

Genes were synthesized with NheI and MluI ends in pUC57 vector (GenScript, Piscataway, N.J.). Typically, the genes were subcloned to the MB5082 'URA3', MB6157 HygR, and MB8327 NatR vectors for marker selection in *Yarrowia lipolytica* transformations, as in WO2016172282. For clean gene insertion by random nonhomologous end joining of the gene and marker HindIII/XbaI (MB5082) or PvuII (MB6157 and MB8327), respectively purified by gel electrophoresis and Qiagen gel purification column. MB5082 'URA3' marker could be reused due to gratuitous repeated flanking sequences that enable selection of circular excisants of the URA3 cassette on FOA. The NatR and HygR markers can be removed by transient expression of Cre recombinase that results in excisants due to the flanking Lox sites.

Plasmid List.

Plasmid, strains, nucleotide and amino acid sequences to be used are listed in Table 1, 2 and the sequence listing. Nucleotide sequence ID NOs:2, 4, 6, 8, 10, 12, 14, 16, 18, 20, 22, 24, 26, 28, 30, 32, 35, 37, and 39 are codon optimized for expression in *Yarrowia*.

TABLE 1 list of plasmids used for construction of the strains carrying the heterologous BCO, RDH and ATF1-genes. The sequence ID NOs refer to the inserts. For more details, see text.

| MB plasmid | Backbone MB | Insert | SEQ ID NO: (aa/nt) |
|---|---|---|---|
| 8457 | 5082 | UmCCO1 | 1/2 |
| 8456 | 5082 | FfCarX | 3/4 |
| 6703 | 5082 | CsZCO | 5/6 |
| 6702 | 5082 | DmNinaB | 7/8 |
| 9068 | 5082 | DrBCO | 9/10 |
| 9279 | 5082 | DrBCO-TPI | 11/12 |
| 9123 | 5082 | IpBCO | 13/14 |
| 9121 | 5082 | EIBCO | 15/16 |
| 9126 | 5082 | LcBCO | 17/18 |
| 8200 | 5082 | FfRDH12 | 19/20 |
| 8064 | 5082 | SbATF1 | 21/22 |
| 8509 | 6157 | FaATF | 23/24 |
| 8510 | 6157 | EcCAT | 25/26 |
| 8511 | 6157 | EaCAcT | 27/28 |
| 8512 | 6157 | MdATF | 29/30 |
| 8513 | 6157 | PhATF | 31/32 |
| 8849 | 5082 | LmATF1 | 33/35 |
| 8610 | 5082 | LfATF1 | 36/37 |
| 8806 | 5082 | LffATF1 | 38/39 |

TABLE 2 list of Yarrowia strains used for production of retinoids carrying the heterologous BCO, RDH and ATF1-genes. For more details, see text.

| ML strain | Description | First described in |
|---|---|---|
| 7788 | Carotene strain | WO2016172282 |
| 15710 | ML7788 transformed with MB7311 -Mucor CarG | WO2016172282 |
| 17544 | ML15710 cured of URA3 by FOA and HygR by Cre/lox | here |
| 17767 | ML17544 transformed with MB6072 DmBCO-URA3 and MB6732 SbATF1-HygR and cured of markers | here |
| 17968 | ML17544 transformed with MB8457 UmCCO1-URA3 and cured of markers | here |
| 17978 | ML17968 transformed with MB8200 FfRDH-URA3 and cured of markers | here |

Normal Phase Retinol Method.

A Waters 1525 binary pump attached to a Waters 717 auto sampler were used to inject samples. A Phenomenex Luna 3µ Silica (2), 150×4.6 mm with a security silica guard column kit was used to resolve retinoids. The mobile phase consists of either, 1000 mL hexane, 30 mL isopropanol, and 0.1 mL acetic acid for astaxanthin related compounds, or 1000 mL hexane, 60 mL isopropanol, and 0.1 mL acetic acid for zeaxanthin related compounds. The flow rate for each is 0.6 mL per minute. Column temperature is ambient. The injection volume is 20 µL. The detector is a photodiode array detector collecting from 210 to 600 nm. Analytes were detected according to Table 3.

TABLE 3 list of analytes using normal phase retinol method. The addition of all added intermediates gives the amount of total retinoids. For more details, see text.

| Intermediates | Retention time [min] | Lambda max [nm] |
|---|---|---|
| 11-cis-dihydro-retinol | 7.1 | 293 |
| 11-cis-retinal | 4 | 364 |
| 11-cis-retinol | 8.6 | 318 |
| 13-cis-retinal | 4.1 | 364 |
| dihydro-retinol | 9.2 | 292 |
| retinyl-acetate | 3.5 | 326 |
| retinyl-ester | 3 | 325 |
| trans-retinal | 4.7 | 376 |
| trans-retinol | 10.5 | 325 |

Sample Preparation.

Samples were prepared by various methods depending on the conditions. For whole broth or washed broth samples the broth was placed in a Precellys® tube weighed and mobile phase was added, the samples were processed in a Precellys® homogenizer (Bertin Corp, Rockville, Md., USA) on the highest setting 3× according to the manufactures directions. In the washed broth the samples were spun in a 1.7 ml tube in a microfuge at 10000 rpm for 1 minute, the broth decanted, 1 ml water added mixed pelleted and decanted and brought up to the original volume the mixture was pelleted again and brought up in appropriate amount of mobile phase and processed by Precellys® bead beating. For analysis of mineral oil fraction, the sample was spun at 4000 RPM for 10 minutes and the oil was decanted off the top by positive displacement pipet (Eppendorf, Hauppauge, N.Y., USA) and diluted into mobile phase mixed by vortexing and measured for retinoid concentration by HPLC analysis.

Fermentation Conditions.

Fermentations were identical to the previously described conditions using preferably a silicone oil or a mineral oil overlay and stirred tank that was preferably glucose or corn oil fed in a bench top reactor with 0.5 L to 5 L total volume (see WO2016172282). Generally, the same results were observed with a fed batch stirred tank reactor with an increased productivity demonstrating the utility of the system for the production of retinoids. Preferably, fermentations were batched with 5% glucose and 20% silicone oil was added after dissolved oxygen plummeted and feed was resumed to achieve 20% dissolved oxygen throughout the feeding program. Alternatively, corn oil was used as a feed and mineral oil was used as a second phase to collect the aliphatic retinoids.

Example 2: Conversion of Beta-Carotene to Retinal in Yarrowia lipolytica

For expression of heterologous BCOs, a beta carotene strain ML17544 was transformed with purified linear DNA fragment by HindII and XbaI mediated restriction endonucleotide cleavage and gel purification of beta carotene oxidase (BCO) containing codon optimized fragments linked to a URA3 nutritional marker. Transforming DNA were derived from MB6702 Drosophila NinaB BCO gene, MB6703 Crocus BCO gene, MB8456 Fusarium BCO gene, and MB8457 Ustilago BCO gene and MB6098 Dario BCO gene, whereby the codon-optimized sequences (SEQ ID NOs:2, 4, 6, 8, 10, 12) had been used. The genes were then grown screening 6-8 isolates in a shake plate analysis, and isolates that performed well were run in a fed batch stirred tank reaction for 8-10 days. Detection of cis- and trans-retinal was made by HPLC using standard parameters as described in WO2014096992, but calibrated with purified standards for the retinoid analytes. The amount of trans-retinal in the retinal mix could be increased to 90% (using the Crocus BCO), 95% (using the Fusarium BCO), 98% (using the Ustilago BCO) and 98% (using Dario BCO), respectively. A comparison with the BCO from Drosophila melanogaster (SEQ ID NO:7) resulted in 61% of trans-retinal based on the total amount of retinal (see Table 4).

TABLE 4

Retinal production in Yarrowia as enhanced by action of heterologous BCOs. "% trans" means percentage of trans-retinal in the mix of retinoids. For more details, see text.

| Organism | BCO gene | % trans- | % retinoids/ DCW | ML strain | MB plasmid |
|---|---|---|---|---|---|
| Drosophila | DmNinB | 61 | 14 | 17544 | 6702 |
| Ustilago | UmCCO1 | 98 | 8 | 17544 | 8457 |
| Fusarium | FfCarX | 95 | 5 | 17544 | 8456 |
| Crocus | ZsZCO | 90 | 0.01 | 17544 | 6703 |
| Dario | DrBCO | 98 | 6 | 17544 | 9068 |
| Dario | DrBCO-TPI | 98 | 6 | 17544 | 9279 |
| Ictalurus | IpBCO | 98 | 5 | 17544 | 9123 |
| Esox | EIBCO | 98 | 3 | 17544 | 9121 |
| Latimeria | LcBCO | 98 | 2 | 17544 | 9126 |

Example 3: Conversion of Retinal to Retinol in Yarrowia lipolytica

For expression of heterologous RDHs, the beta carotene strain ML17767 was transformed with purified HinDIII/

XbaI fragments derived from plasmids containing retinol dehydrogenase (RDH) gene fragments linker to a URA3 promoter. Six to eight isolates were screened for a decrease in the retinol: retinal ratio in a shake plate assay and successful isolates were run in a fed batch stirred tank reactor for eight days which showed an order of magnitude increase in the productivity of the process which indicates a utility in large scale production. The best results were obtained with the Fusarium RDH12 homolog with only 2% or residual retinal maintained after 8 days of shake-flask incubation as described above. The isolate derived from the Fusarium sequence demonstrated an increased reduction of retinol.

Example 4: Conversion of Retinol to Retinyl Acetate in Yarrowia lipolytica

For expression of heterologous ATF1, the trans retinol producing strain ML17968 was transformed with purified PvuII gene fragments containing acetyltransferase gene fragments linked to a Hygromycin resistance marker (HygR) for selection rich media (YPD) containing 100 ug/ml hygromycin. Prior to plating the cultures were outgrown in YPD for four hours to synthesize the antibiotic resistance genes. Isolates were screened for acylation in shake plate assays and successful isolates were screened in fed batch stirred tank reactor which showed an order of magnitude increased productivity indicating utility in the production of retinoids. The data from the analysis are shown in Table 5).

TABLE 5

Trans retinoid production in Yarrowia as enhanced by action of heterologous ATF1 enzymes. "% acetylation" means percentage of trans-retinyl acetate in the mix of retinoids. For more details, see text.

| Organism | ATF1 gene | % acetylation- | ML strain | MB plasmid |
|---|---|---|---|---|
| S. bayanus | SbATFI | 10.3 | 17968 | 6832 |
| P. hybrida | PhATF | 2.1 | 17968 | 8513 |
| E. alatus | EaCAcT | 0.45 | 17968 | 8511 |
| E. coli | EcCAT | 0.35 | 17968 | 8510 |
| L. fermentata | LfATFI | 9.6 | 18523 | 8610 |
| L. fermentata | LffATFI | 11.7 | 18523 | 8806 |
| L. mirantina | LmATFI | 40.4 | 18523 | 8849 |

Example 5: ATF1 Activity Assay

For expression of heterologous ATF1, the trans retinol producing strain ML17968 was transformed with purified PvuII gene fragments containing acetyltransferase gene fragments linked to a Hygromycin resistance marker (HygR) for selection rich media (YPD) containing 100 ug/ml hygromycin. Prior to plating the cultures were outgrown in YPD for four hours to synthesize the antibiotic resistance genes. Isolates were screened for acylation in shake plate assays, specifically using 10% glucose as a carbon source in 0.25× YP with silicone oil as an overlay and successful isolates were further screened in fed batch stirred tank reactor with glucose feed and silicone oil overlay, which showed an order of magnitude increased productivity indicating utility in the production of retinoids. The data from the analysis are shown in Table 5.

Example 6: Conversion of Beta-Carotene to Retinyl Acetate in Saccharomyces cerevisiae Typically, a beta carotene strain is transformed with heterologous genes encoding for enzymes such as geranylgeranyl synthase, phytoene synthase, lycopene synthase, lycopene cyclase constructed that is producing beta carotene according to standard methods as known in the art (such as e.g. as described in US20160130628 or WO2009126890). Further, when transformed with beta carotene oxidase genes retinal can be produced. Further, when transformed with retinol dehydrogenase, then retinol can be produced. The retinol can be acetylated by transformation with genes encoding alcohol acetyl transferases. Optionally, the endogenous retinol acylating genes can be deleted. Further, the enzymes can be selected to produce and acylate the trans form of retinol to yield all trans retinyl acetate, and long chain esters of trans retinol, respectively. With this approach, similar results regarding specificity for trans-isoform or productivity towards retinyl acetate are obtained.

The invention claimed is:

1. A process for production of trans-retinyl acetate comprising cultivating a retinoid-producing fungal host cell in an aqueous medium under suitable culture conditions, wherein
 (a) the host cell expresses
  (i) a heterologous stereo-selective beta-carotene oxidizing enzyme (BCO) capable of catalyzing the conversion of beta-carotene into a retinal mix comprising cis- and trans-retinal,
  (ii) a heterologous retinol dehydrogenase (RDH) enzyme [EC 1.1.1.105] capable of converting retinal into retinol, and
  (iii) a heterologous fungal acetyl transferase 1 enzyme (ATF1) [EC 2.3.1.84] capable of catalysing the conversion of trans-retinol to a retinyl acetate, and
 (b) the host cell is capable of
  (i) producing a retinal mix comprising cis- and trans-retinal, wherein the percentage of trans-retinal in the mix is at least 90%,
  (ii) converting the retinal mix into retinol with a total conversion of at least 90% towards generation of retinol, and (iii) converting the retinol into retinyl acetate, wherein at least 40% of the total amount of retinoids produced by said host cell is retinyl acetate.

2. A process for production of vitamin A comprising the steps of:
(a) introducing a nucleic acid molecule encoding stereoselective BCO, acetyl transferase [EC 2.3.1.84], and retinol dehydrogenase [EC 1.1.1.105] enzymes into a suitable fungal host cell; and
(b) expressing said introduced enzymes to enable enzymatic conversion of beta-carotene into retinal comprising at least a percentage of 90% in trans isoform based on the total amount of retinoids produced by the host cell, to enable enzymatic conversion of said retinal into retinol comprising a percentage of at least 90% towards generation of retinol and to enable enzymatic conversion of retinol into retinyl acetate, wherein at least 40% of the total amount of retinoids produced by said host cell is retinyl acetate, said retinyl acetate comprising at least a percentage of 90% in trans isoform.

3. The process according to claim 1, wherein the heterologous ATF1 is capable of catalysing the conversion of trans-retinol into trans-retinyl acetate.

4. The process according to claim 1, wherein the heterologous RDH is a fungal RDH [EC 1.1.1.105].

5. The process according to claim 1, wherein the host cell further comprises a modification to reduce or abolish the activity of one or more endogenous acyltransferase(s) [EC 2.3.1] catalyzing the acylation of retinol into long chain retinyl esters.

6. The process according to claim 1, wherein the heterologous BCO is a fungal, plant or animal BCO.

7. The process according to claim 1, wherein the host cell produces a retinyl acetate mix comprising at least 65% trans-retinyl acetate isoform.

8. The process according to claim 1, wherein the fungal host cell is a yeast cell.

9. The process according to claim 1 further comprising isolating said retinyl acetate.

10. The process according to claim 7 further comprising isolating said trans-retinyl acetate.

11. The process according to claim 1, wherein the heterologous ATF1 comprises an amino acid sequence with at least 90% identity to SEQ ID NO: 33.

12. The process according to claim 11, wherein the heterologous BCO and RDH comprises an amino acid sequence with at least 90% identity to SEQ ID NO: 9 and 19, respectively.

13. The process according to claim 11, wherein the fungal host cell is a yeast cell.

14. The process according to claim 11, wherein the fungal host cell is a *Saccharomyces* or *Yarrowia* cell.

15. The process according to claim 11, wherein the fungal host cell is a *Yarrowia lipolytica* or *Saccharomyces cerevisiae* cell.

16. The process according to claim 11, wherein the fungal host cell further comprises a mutation in a gene encoding an endogenous acyltransferase enzyme that is capable of catalyzing the conversion of retinol into a long chain retinyl ester.

17. The process according to claim 11, further comprising isolating said retinyl acetate.

* * * * *

SEQUENCE LISTING

<160> NUMBER OF SEQ ID NOS: 43

<210> SEQ ID NO 1
<211> LENGTH: 787
<212> TYPE: PRT
<213> ORGANISM: Ustilago maydis

<400> SEQUENCE: 1

Met Val Lys Gly Ser Ser Asn Arg Arg Gln His Ser Ala Ser Leu Gln
1               5                   10                  15

Gly Leu Pro Ser Ser Gln His Cys Ala Pro Val Ile Ser Ile Pro Ser
                20                  25                  30

Pro Pro Pro Pro Ala Glu Asp His Ala Tyr Pro Pro Ser Ser Phe Thr
            35                  40                  45

Ile Pro Leu Ser Lys Asp Glu Glu Leu Ala Glu Ala Gly Pro Ser Arg
        50                  55                  60

```
Pro Gly Ser Ser Ala Ile Ser Arg Arg Pro Val Leu Ser Arg Arg Arg
 65                  70                  75                  80

Thr Ser Lys Lys Glu Tyr Val His Pro Tyr Leu Ser Gly Asn Phe Ala
                 85                  90                  95

Pro Val Thr Thr Glu Cys Pro Leu Thr Asp Cys Leu Phe Glu Gly Thr
            100                 105                 110

Ile Pro Glu Glu Phe Ala Gly Ser Gln Tyr Val Arg Asn Gly Gly Asn
        115                 120                 125

Pro Leu Ala Asn Ser Glu Arg Asp Arg Asp Ala His Trp Phe Asp Ala
    130                 135                 140

Asp Gly Met Leu Ala Gly Val Leu Phe Arg Arg Thr Pro Lys Gly Thr
145                 150                 155                 160

Ile Gln Pro Cys Phe Leu Asn Arg Phe Ile Leu Thr Asp Leu Leu Leu
                165                 170                 175

Ser Thr Pro Glu His Ser Arg Leu Pro Tyr Val Pro Ser Ile Ala Thr
            180                 185                 190

Leu Val Asn Pro His Thr Ser Val Phe Trp Leu Cys Glu Ile Ile
        195                 200                 205

Arg Thr Phe Val Leu Ala Met Leu Thr Trp Leu Pro Gly Leu Gly Leu
    210                 215                 220

Gly Gly Asn Gln Lys Leu Lys Arg Ile Ser Val Ala Asn Thr Ser Val
225                 230                 235                 240

Phe Trp His Asp Gly Lys Ala Met Ala Gly Cys Glu Ser Gly Pro Pro
                245                 250                 255

Met Arg Ile Met Leu Pro Gly Leu Glu Thr Ala Gly Trp Tyr Thr Gly
            260                 265                 270

Glu Glu Asp Lys Glu Lys Glu Thr Cys Asp Lys Asn Ser Gly Asn Ser
        275                 280                 285

Leu Thr Ser Ser Ser Lys Gly Phe Gly Gly Pro Pro Ile Val
    290                 295                 300

Ser Met Leu Arg Glu Phe Thr Thr Ala His Pro Lys Ile Asp Pro Arg
305                 310                 315                 320

Thr Gln Glu Leu Leu Leu Tyr His Met Cys Phe Glu Pro Pro Tyr Leu
                325                 330                 335

Arg Ile Ser Val Ile Pro Ala Ser Gln Ser Lys Lys Thr Asp Leu Pro
            340                 345                 350

Ala His Ala Lys Thr Ile Lys Gly Lys Ala Val Arg Gly Leu Lys Gln
        355                 360                 365

Pro Lys Met Met His Asp Phe Gly Ala Thr Ala Thr Gln Thr Val Ile
    370                 375                 380

Ile Asp Val Pro Leu Ser Leu Asp Met Met Asn Leu Val Arg Gly Lys
385                 390                 395                 400

Pro Ile Leu His Tyr Asp Pro Ser Gln Pro Thr Arg Phe Gly Ile Leu
                405                 410                 415

Pro Arg Tyr Glu Pro Glu Arg Val Arg Trp Tyr Glu Ser Ala Glu Ala
            420                 425                 430

Cys Cys Ile Tyr His Thr Ala Asn Ser Trp Asp Asp Gly Lys Phe
        435                 440                 445

Asp Ala Ser His Glu His Ala Thr Arg Ser Ala Ile Arg Gly Val Asn
    450                 455                 460

Met Leu Gly Cys Arg Leu Asn Ser Ala Thr Leu Val Tyr Ser Ala Gly
465                 470                 475                 480
```

```
Asn Leu Leu Pro Pro Ser His Val Leu Pro Pro Asn Cys Pro Glu
            485                 490                 495
Lys Cys Gln Leu Tyr Tyr Trp Arg Phe Asp Leu Glu His Ala Glu Thr
        500                 505                 510
Asn Thr Ile Ser His Glu Phe Ala Leu Ser Asp Ile Pro Phe Glu Phe
        515                 520                 525
Pro Thr Ile Asn Glu Asp Tyr Ser Met Gln Gln Ala Cys Tyr Val Tyr
        530                 535                 540
Gly Thr Ser Met Arg Asp Gly Thr Phe Asp Ala Gly Leu Gly Lys Ala
545                 550                 555                 560
Ala Lys Ile Asp Ala Leu Val Lys Leu Asp Ala Gln Ala Leu Ile Arg
                565                 570                 575
Lys Gly Lys Ala Met Trp Ser Gln Gly Arg Leu Lys Ala Gly Asp Ser
            580                 585                 590
Val Asp Thr Arg Thr Val Glu Glu Val Leu Thr Ala Gln Arg Asp Gly
        595                 600                 605
Ser Ala Ser Pro Glu Asp Pro Ile Lys Ile Phe Glu Met Pro Arg Gly
        610                 615                 620
Trp Tyr Ala Gln Glu Thr Thr Phe Val Pro Arg Arg Ser Ser Thr Asn
625                 630                 635                 640
Glu Thr Ser Gln Glu Asp Asp Gly Trp Leu Val Cys Tyr Val Phe Asp
                645                 650                 655
Glu Ala Thr Gly Leu His Pro Ser Thr Gly Val Leu Pro Gly Ala
            660                 665                 670
Ser Ser Glu Leu Trp Ile Ile Asp Ala Lys Leu Met Ser Arg Val Val
        675                 680                 685
Cys Arg Ile Lys Leu Pro Gln Arg Val Pro Tyr Gly Leu His Gly Thr
        690                 695                 700
Leu Phe Thr Glu Glu Gln Ile Ala Ser Gln Lys Pro Ile Asp Pro Ser
705                 710                 715                 720
Gln Val Arg Ser Trp Ala Leu Ser Ile Asn Leu Ala Asp Pro Phe Ser
                725                 730                 735
Ser Ser Ala Leu Gly Ser Thr Val Tyr Ser Ala Ala Gly Lys Ala Ala
            740                 745                 750
Thr Ser Lys Phe Lys Asn Arg Glu Glu Thr Tyr Ala Ala Phe Ile Lys
        755                 760                 765
Asp Pro Ile Arg Ile Gly Ala Trp Trp Val Lys Arg Asn Ile Glu Leu
        770                 775                 780
Leu Ile Ala
785

<210> SEQ ID NO 2
<211> LENGTH: 2364
<212> TYPE: DNA
<213> ORGANISM: Artificial Sequence
<220> FEATURE:
<223> OTHER INFORMATION: Yarrowia codon-optimized UmCCO1

<400> SEQUENCE: 2
atggttaagg ctcctctaa ccgacgacag cactccgctt cccttcaggg actcccttct      60
tctcagcact gtgccccgt tatctctatt ccttctcccc ctcccctgc tgaggatcac      120 gcttacccc cttcctcttt cactattcct ctctccaagg atgaggagct tgctgaggcc      180
ggaccctctc gacccggttc ctctgctatt tctcgacgac ctgttctgtc tcgacgacga      240
acttctaaga aggagtacgt tcaccctac ctctccggca actttgcccc tgttaccact      300
```

-continued

```
gagtgccctc tcaccgattg tctctttgag ggtactatcc ctgaggagtt tgctggctcc    360
cagtacgtcc gaaacggcgg aaacccccct tgccaactccg agcgagatcg agatgcccac    420
tggttcgatg ctgacggtat gctggctgga gttctctttc gacgaacccc caagggcacc    480
attcagcctt gtttcctcaa ccgattcatt ctcaccgacc tcctgctctc taccccctgag   540 cactctcgac tcccttacgt cccttccatc gctactctcg tcaaccccca cacttccgtc    600
ttttggctcc tttgtgagat catccgaact ttcgttctgg ctatgcttac ctggctccct    660
ggcctcggac tcggtggcaa ccagaagctc aagcgaatct ctgttgctaa cacctccgtt    720
ttctggcacg acggaaaggc tatggctgga tgtgagtctg acccccctat gcgaatcatg    780
ctccctggtc ttgagactgc cggctggtac actggtgagg aggataagga aaggagact    840 tgtgataaga actctggcaa ctctctcact tcttcctctt ctaagggttt tggcggaggc    900
cctcccattg tctccatgct tcgagagttt accactgctc accccaagat tgaccctcga    960
acccaggagc tccttctcta ccacatgtgc ttcgagcccc cttaccttcg aatctctgtc   1020
atccctgctt tcagtctaa gaagactgac ctccctgctc acgctaagac cattaagggt    1080
aaggctgtgc gaggtcttaa gcagcccaag atgatgcacg atttcggcgc taccgccact   1140
cagaccgtca tcatcgacgt ccctctctcc ctcgacatga tgaacctcgt ccgaggcaag   1200
cccattctgc actacgatcc ctctcagcct acccgattcg gtattcttcc ccgatacgag   1260
cctgagcgag tgcgatggta cgagtctgcc gaggcttgct gtatctacca caccgccaac   1320
tcttgggatg acgatggcaa gtttgacgct tctcacgagc acgctacccg atccgccatc   1380
cgaggcgtca acatgctcgg ctgccgactc aactctgcca ccctcgtgta ctctgctgga   1440
aaccttctcc ctccctctca cgtccttccc cctcccaact gccctgagaa gtgtcagctc   1500
tactactggc gattcgacct tgagcacgct gagactaaca ccatttccca cgagtttgct   1560
ctgtccgaca ttcctttcga gttccccacc atcaacgagg actactctat gcagcaggct   1620
tgttacgttt acggtacttc catgcgagat ggcacctttg acgctggact cggaaaggct   1680
gctaagattg acgcccttgt aagctggac gctcaggccc ttattcgaaa gggcaaggcc    1740
atgtggtccc agggacgact taaggctgga gactctgtgg acacccgaac cgttgaggag   1800
gttctcactg ctcagcgaga tggttctgcc tcccctgagg accctatcaa gatttttcgag   1860 atgccccgag gatggtacgc tcaggagact accttcgtcc ctcgacgatc ctctactaac   1920
gagacttctc aggaggatga cggttggctc gtctgctacg tgttcgatga ggccactggc   1980
cttcacccct tccaccggaga ggttctccct ggcgcttcct ccgagctgtg gatcattgat   2040
gccaagctca tgtcccgagt cgtttgccga atcaagctcc cccagcgagt cccttacgga   2100
ctccacggca ctctctttac cgaggagcag attgcctctc agaagcctat cgacccttct   2160
caggtccgat cctgggctct gtctatcaac cttgccgatc ccttctcctc ttccgccctt   2220
ggctctaccg tgtactccgc cgctggtaag gctgccacct ccaagtttaa gaaccgagag   2280
gagacttacg ctgccttcat caaggaccct atccgaatcg gcgcttggtg ggtcaagcga   2340
aacatcgagc tcctgattgc ttaa                                           2364
```

<210> SEQ ID NO 3
<211> LENGTH: 696
<212> TYPE: PRT
<213> ORGANISM: Fusarium fujikuroi

<400> SEQUENCE: 3

```
Met Lys Phe Leu Gln Gln Asn Ser Phe Thr Gln Thr Ser Met Ser Gln
1               5                   10                  15

Pro His Glu Asp Val Ser Pro Ala Ile Arg His Pro Tyr Leu Thr Gly
            20                  25                  30

Asn Phe Ala Pro Ile His Lys Thr Thr Asn Leu Thr Pro Cys Thr Tyr
        35                  40                  45

Ser Gly Cys Ile Pro Pro Glu Leu Thr Gly Gln Tyr Val Arg Asn
    50                  55                  60

Gly Gly Asn Pro Val Ser His Gln Asp Leu Gly Lys Asp Ala His Trp
65                  70                  75                  80

Phe Asp Gly Asp Gly Met Leu Ser Gly Val Ala Phe Arg Lys Ala Ser
                85                  90                  95

Ile Asp Gly Lys Thr Ile Pro Glu Phe Val Asn Gln Tyr Ile Leu Thr
            100                 105                 110

Asp Leu Tyr Leu Ser Arg Lys Thr Thr Ser Ile Ala Ser Pro Ile Met
        115                 120                 125

Pro Ser Ile Thr Thr Leu Val Asn Pro Leu Ser Thr Met Phe Gln Ile
130                 135                 140

Met Phe Ala Thr Phe Arg Thr Ile Phe Leu Val Ile Leu Ser Asn Leu
145                 150                 155                 160

Pro Gly Ser Gln Gln Ala Ile Lys Arg Ile Ser Val Ala Asn Thr Ala
                165                 170                 175

Val Leu Tyr His Asp Gly Arg Ala Leu Ala Thr Cys Glu Ser Gly Pro
            180                 185                 190

Pro Met Arg Ile Gln Leu Pro Ser Leu Asp Thr Val Gly Trp Phe Asp
        195                 200                 205

Gly Val Glu Ala Glu Gly Glu Pro Glu Ile Ser Gln Ala Gly Ser Asp
    210                 215                 220

Asp Ser Pro Phe Gly Gly Ser Gly Ile Phe Ser Phe Met Lys Glu Trp
225                 230                 235                 240

Thr Thr Gly His Pro Lys Val Asp Pro Val Thr Gly Glu Met Leu Leu
                245                 250                 255

Tyr His Asn Thr Phe Met Pro Pro Tyr Val His Cys Ser Val Leu Pro
            260                 265                 270

Lys Ser Asn Glu Lys Ala Pro Gly His Arg Leu Val Asn Gln Pro Val
        275                 280                 285

Leu Gly Val Ser Gly Ala Arg Met Met His Asp Phe Gly Ala Ser Arg
    290                 295                 300

Ser His Thr Ile Ile Met Asp Leu Pro Leu Ser Leu Asp Pro Leu Asn
305                 310                 315                 320

Thr Met Lys Gly Lys Glu Val Val Ala Tyr Asp Pro Thr Lys Pro Ser
                325                 330                 335

Arg Phe Gly Val Phe Pro Arg His Leu Pro Ser Ser Val Arg Trp Phe
            340                 345                 350

His Thr Ala Pro Cys Cys Ile Phe His Thr Ala Asn Thr Trp Asp Ser
        355                 360                 365

Gln Ser Ser Glu Gly Glu Leu Ser Val Asn Leu Leu Ala Cys Arg Met
    370                 375                 380

Thr Ser Ser Thr Leu Val Tyr Thr Ala Gly Asn Ile Arg Pro Pro Val
385                 390                 395                 400

Arg Ser Arg Cys Thr Gln Ala Arg Val Trp Ser Asp Glu Arg Glu Glu
                405                 410                 415
```

```
Thr Ala Cys Arg Tyr Lys Glu Ala Pro Ala Leu Glu Ser Pro Gly Glu
            420                 425                 430

Ser Thr Gly Leu Ala Asp Tyr Phe Pro Ile Thr Ala Glu Ser Asp Asp
        435                 440                 445

Tyr Asp Gln Cys Arg Leu Tyr Tyr Tyr Glu Phe Asp Leu Ala Met Glu
    450                 455                 460

Ser Arg Asn His Val Lys Ser Gln Trp Ala Leu Ser Ala Ile Pro Phe
465                 470                 475                 480

Glu Phe Pro Ser Val Arg Pro Asp Arg Glu Met Gln Glu Ala Arg Tyr
                485                 490                 495

Ile Tyr Gly Cys Ser Thr Ser Thr Ser Cys Phe Gly Val Ala Leu Gly
            500                 505                 510

Arg Ala Asp Lys Val Asp Leu Leu Val Lys Met Asp Ala Lys Thr Leu
        515                 520                 525

Ile Gln Arg Gly Lys Lys Met Asn Ala Thr Ser Ile Thr Gly Cys Val
    530                 535                 540

Asp Arg Arg Ser Val Cys Glu Ile Leu Gln Glu Gln Arg Lys Asp Asp
545                 550                 555                 560

Pro Ile Tyr Ile Phe Arg Leu Pro Pro Asn His Tyr Ala Gln Glu Pro
                565                 570                 575

Arg Phe Val Pro Arg Ala Cys Ser Thr Glu Glu Asp Asp Gly Tyr Leu
            580                 585                 590

Leu Phe Tyr Val Phe Asp Glu Ser Gln Leu Leu Pro Ser Gly Asp Cys
        595                 600                 605

Pro Pro Ser Ala Thr Ser Glu Leu Trp Ile Leu Asp Ala Lys Asn Met
    610                 615                 620

Arg Asp Val Val Ala Lys Val Arg Leu Pro Gln Arg Val Pro Tyr Gly
625                 630                 635                 640

Leu His Gly Thr Trp Phe Ser Gln Asp Ile Glu Ser Gln Arg Ser
                645                 650                 655

Val Glu Ser Leu Arg Ser Leu Glu Val Val Gln Arg Lys Lys Glu Glu
            660                 665                 670

Trp Val Asn Ser Gly Gly Gln Ile Arg Lys Ser Trp Met Val Leu Arg
        675                 680                 685

Glu Lys Leu Glu Lys Ala Val Gly
    690                 695

<210> SEQ ID NO 4
<211> LENGTH: 2091
<212> TYPE: DNA
<213> ORGANISM: Artificial Sequence
<220> FEATURE:
<223> OTHER INFORMATION: Yarrowia codon-optimized FfCarX

<400> SEQUENCE: 4
atgaagtttc tccagcagaa ctcctttacc cagacctcta tgtctcagcc tcacgaggat      60
gtctctcccg ccattcgaca cccttacctt accggcaact tgctcctat tcacaagacc     120 actaacctca ctccctgtac ttactctggc tgcattcccc ccgagcttac cggaggtcag     180
tacgttcgaa acggcggaaa ccctgtctcc caccaggatc tcggaaagga tgctcactgg     240
ttcgatggcg acgtatgct ctctggcgtc gcctttcgaa aggcttccat gatggcaag      300 actatccctg agttcgttaa ccagtacatt cttaccgacc tttacctttc tcgaaagacc     360
acctctattg cttcccctat tatgccctct atcaccaccc tggttaaccc tctctctact     420
atgtttcaga tcatgttcgc caccttccga actatcttcc tcgtcattct ctccaacctc     480
```

```
cctggttctc agcaggctat caagcgaatc tccgttgcca acactgctgt tctttaccac    540
gatggtcgag ctcttgccac ttgcgagtct ggccccccca tgcgaatcca gcttccctcc    600
ctcgataccg ttggctggtt cgacggtgtt gaggctgagg gtgagcctga gatttctcag    660
gccggctctg atgactctcc cttcggcggt tccggcatct tctcctttat gaaggagtgg    720
accaccggcc accctaaggt ggaccccgtt accggagaga tgcttctcta ccacaacacc    780
ttcatgcctc cctacgtgca ctgctctgtt cttcccaagt ctaacgagaa ggctcccgga    840
caccgacttg ttaaccagcc cgttcttggt gtttctggtg cccgaatgat gcacgacttc    900
ggagcctctc gatctcacac tatcatcatg gaccttcccc tgtctctgga ccctctcaac    960
actatgaagg gaaggaggt tgttgcttac gaccctacca gccttctcg attcggtgtg   1020 ttcccccgac accttccctc ttccgtgcga tggtttcaca ctgctccttg ctgtatcttt   1080
cacactgcta acacttggga ttctcagtcc tctgagggag agctttctgt taacctcctt   1140
gcctgccgaa tgacctcttc tacccttgtt tacactgccg gcaacatccg acctcccgtt   1200
cgatctcgat gtactcaggc ccgagtctgg tccgatgagc gagaggagac tgcttgtcga   1260
tacaaggagg ctcctgctct tgagtctcct ggtgagtcca ctggccttgc cgactacttt   1320
cccattaccg ctgagtccga cgactacgat cagtgccgac tctactacta cgagtttgac   1380
cttgctatgg agtcccgaaa ccacgtcaag tcccagtggg ctctctctgc cattcctttc   1440
gagtttccct ctgtgcgacc tgaccgagag atgcaggagg ctcgatacat ctacggctgt   1500
tccacttcca cttcttgctt cggtgtggct ctcggacgag ctgataaggt tgaccttctc   1560
gttaagatgg atgccaagac cctcattcag cgaggaaaga agatgaacgc tacttccatc   1620
accggatgcg ttgatcgacg atctgtctgc gagatccttc aggagcagcg aaaggatgac   1680
cctatttaca ttttccgact tccccctaac cactacgctc aggagccccg attcgttccc   1740
cgagcttgtt ctactgagga ggacgacgga tacctccttt tctacgtgtt cgacgagtct   1800
cagctccttc cctctggcga ttgtcctccc tctgctactt ctgagctttg gattcttgac   1860
gctaagaaca tgcgagatgt tgtggccaag gtccgacttc cccagcgagt tccttacggt   1920
ctgcacggta cttggttctc ttctcaggat attgagtctc agcgatctgt ggagtctctt   1980
cgatctcttg aggttgtgca cgaaagaag gaggagtggg ttaactctgg aggccagatt   2040
cgaaagtcct ggatggttct tcgagagaag ctggagaagg ctgttggata g           2091
```

<210> SEQ ID NO 5
<211> LENGTH: 369
<212> TYPE: PRT
<213> ORGANISM: Crocus sativus

<400> SEQUENCE: 5

```
Met Gln Val Asp Pro Thr Lys Gly Ile Gly Leu Ala Asn Thr Ser Leu
1               5                   10                  15

Gln Phe Ser Asn Gly Arg Leu His Ala Leu Cys Glu Tyr Asp Leu Pro
            20                  25                  30

Tyr Val Val Arg Leu Ser Pro Glu Asp Gly Asp Ile Ser Thr Val Gly
        35                  40                  45

Arg Ile Glu Asn Asn Val Ser Thr Lys Ser Thr Thr Ala His Pro Lys
    50                  55                  60

Thr Asp Pro Val Thr Gly Glu Thr Phe Ser Phe Ser Tyr Gly Pro Ile
65                  70                  75                  80

Gln Pro Tyr Val Thr Tyr Ser Arg Tyr Asp Cys Asp Gly Lys Lys Ser
                85                  90                  95
```

-continued

```
Gly Pro Asp Val Pro Ile Phe Ser Phe Lys Glu Pro Ser Phe Val His
                100                 105                 110

Asp Phe Ala Ile Thr Glu His Tyr Ala Val Pro Asp Ile Gln Ile
        115                 120                 125

Val Met Lys Pro Ala Glu Ile Val Arg Gly Arg Met Ile Gly Pro
130                 135                 140

Asp Leu Glu Lys Val Pro Arg Leu Gly Leu Leu Pro Arg Tyr Ala Thr
145                 150                 155                 160

Ser Asp Ser Glu Met Arg Trp Phe Asp Val Pro Gly Phe Asn Met Val
                165                 170                 175

His Val Val Asn Ala Trp Glu Glu Gly Gly Glu Val Val Ile
                180                 185                 190

Val Ala Pro Asn Val Ser Pro Ile Glu Asn Ala Ile Asp Arg Phe Asp
        195                 200                 205

Leu Leu His Val Ser Val Glu Met Ala Arg Ile Glu Leu Lys Ser Gly
210                 215                 220

Ser Val Ser Arg Thr Leu Leu Ser Ala Glu Asn Leu Asp Phe Gly Val
225                 230                 235                 240

Ile His Arg Gly Tyr Ser Gly Arg Lys Ser Arg Tyr Ala Tyr Leu Gly
                245                 250                 255

Val Gly Asp Pro Met Pro Lys Ile Arg Gly Val Val Lys Val Asp Phe
        260                 265                 270

Glu Leu Ala Gly Arg Gly Glu Cys Val Val Ala Arg Glu Phe Gly
                275                 280                 285

Val Gly Cys Phe Gly Gly Glu Pro Phe Phe Val Pro Ala Ser Ser Lys
        290                 295                 300

Lys Ser Gly Gly Glu Glu Asp Asp Gly Tyr Val Val Ser Tyr Leu His
305                 310                 315                 320

Asp Glu Gly Lys Gly Glu Ser Ser Phe Val Val Met Asp Ala Arg Ser
                325                 330                 335

Pro Glu Leu Glu Ile Leu Ala Glu Val Val Leu Pro Arg Arg Val Pro
        340                 345                 350

Tyr Gly Phe His Gly Leu Phe Val Thr Glu Ala Glu Leu Leu Ser Gln
        355                 360                 365

Gln
```

<210> SEQ ID NO 6
<211> LENGTH: 1110
<212> TYPE: DNA
<213> ORGANISM: Artificial Sequence
<220> FEATURE:
<223> OTHER INFORMATION: Yarrowia codon-optimized CsZCO

<400> SEQUENCE: 6

```
atgcaggtgg accccaccaa gggtatcggc ctggccaaca cttctctcca gttctccaac      60
ggacgactcc acgctctttg cgagtacgac ctcccctacg tcgttcgact ctcccccgag     120
gacggtgaca tctctaccgt cggacgaatc gagaacaacg tttctactaa gtctaccacc     180
gcccacccca agaccgaccc cgtcaccgga gagaccttct cttttctccta cggtcccatt     240 cagccctacg tcacctactc ccgatacgac tgcgacggca agaagtccgg ccccgacgtg     300
cccatcttct ctttcaagga gccctctttc gtccacgact cgccatcac cgagcactac     360 gccgtctttc ccgacattca gatcgtgatg aagcccgccg agatcgttcg aggacgacga     420
atgatcggcc ccgaccttga aaggtccccc cgactgggcc ttctcccccg atacgccacc     480
```

-continued

| | |
|---|---|
| tccgactccg agatgcgatg gttcgacgtg cccggtttca acatggttca cgtggttaac | 540 |
| gcttgggagg aggagggcgg agaggtcgtg gtcatcgtgg ccccccaacgt gtcccccatt | 600 |
| gagaacgcca tcgaccgatt cgacctcctc cacgtgtctg tggagatggc ccgaatcgag | 660 |
| ctgaagtccg gttccgtgtc ccgaacccct ctctctgccg agaacctcga tttcggtgtg | 720 |
| attcaccgag ctactccgg tcgaaagtcc cgatacgctt acctcggagt cggcgacccc | 780 |
| atgcccaaga ttcgaggtgt ggtcaaggtg gacttcgagc tggccggacg aggagagtgc | 840 |
| gtggttgccc gacgagagtt cggcgtgggt tgtttcggtg gagagcccct ctttgtcccc | 900 |
| gcttcttcca gaagtctgg aggcgaggag gacgatggct acgttgtgtc ttaccttcac | 960 |
| gacgagggaa agggagagtc ctctttcgtc gtgatggacg ctcgatctcc cgagctggag | 1020 |
| attcttgccg aggtggttct gccccgacga gttccctacg gttttcacgg cctctttgtt | 1080 |
| accgaggccg agcttctctc ccagcagtag | 1110 |

<210> SEQ ID NO 7
<211> LENGTH: 620
<212> TYPE: PRT
<213> ORGANISM: Drosophila melanogaster

<400> SEQUENCE: 7

Met Ala Ala Gly Val Phe Lys Ser Phe Met Arg Asp Phe Ala Val
1               5                   10                  15

Lys Tyr Asp Glu Gln Arg Asn Asp Pro Gln Ala Glu Arg Leu Asp Gly
            20                  25                  30

Asn Gly Arg Leu Tyr Pro Asn Cys Ser Ser Asp Val Trp Leu Arg Ser
        35                  40                  45

Cys Glu Arg Glu Ile Val Asp Pro Ile Glu Gly His Ser Gly His
    50                  55                  60

Ile Pro Lys Trp Ile Cys Gly Ser Leu Leu Arg Asn Gly Pro Gly Ser
65                  70                  75                  80

Trp Lys Val Gly Asp Met Thr Phe Gly His Leu Phe Asp Cys Ser Ala
                85                  90                  95

Leu Leu His Arg Phe Ala Ile Arg Asn Gly Arg Val Thr Tyr Gln Asn
            100                 105                 110

Arg Phe Val Asp Thr Glu Thr Leu Arg Lys Asn Arg Ser Ala Gln Arg
        115                 120                 125

Ile Val Val Thr Glu Phe Gly Thr Ala Ala Val Pro Asp Pro Cys His
    130                 135                 140

Ser Ile Phe Asp Arg Phe Ala Ala Ile Phe Arg Pro Asp Ser Gly Thr
145                 150                 155                 160

Asp Asn Ser Met Ile Ser Ile Tyr Pro Phe Gly Asp Gln Tyr Tyr Thr
                165                 170                 175

Phe Thr Glu Thr Pro Phe Met His Arg Ile Asn Pro Cys Thr Leu Ala
            180                 185                 190

Thr Glu Ala Arg Ile Cys Thr Thr Asp Phe Val Gly Val Val Asn His
        195                 200                 205

Thr Ser His Pro His Val Leu Pro Ser Gly Thr Val Tyr Asn Leu Gly
    210                 215                 220

Thr Thr Met Thr Arg Ser Gly Pro Ala Tyr Thr Ile Leu Ser Phe Pro
225                 230                 235                 240

His Gly Glu Gln Met Phe Glu Asp Ala His Val Val Ala Thr Leu Pro
                245                 250                 255

```
Cys Arg Trp Lys Leu His Pro Gly Tyr Met His Thr Phe Gly Leu Thr
            260                 265                 270

Asp His Tyr Phe Val Ile Val Glu Gln Pro Leu Ser Val Ser Leu Thr
        275                 280                 285

Glu Tyr Ile Lys Ala Gln Leu Gly Gly Gln Asn Leu Ser Ala Cys Leu
    290                 295                 300

Lys Trp Phe Glu Asp Arg Pro Thr Leu Phe His Leu Ile Asp Arg Val
305                 310                 315                 320

Ser Gly Lys Leu Val Gln Thr Tyr Glu Ser Glu Ala Phe Phe Tyr Leu
                325                 330                 335

His Ile Ile Asn Cys Phe Glu Arg Asp Gly His Val Val Val Asp Ile
            340                 345                 350

Cys Ser Tyr Arg Asn Pro Glu Met Ile Asn Cys Met Tyr Leu Glu Ala
        355                 360                 365

Ile Ala Asn Met Gln Thr Asn Pro Asn Tyr Ala Thr Leu Phe Arg Gly
    370                 375                 380

Arg Pro Leu Arg Phe Val Leu Pro Leu Gly Thr Ile Pro Pro Ala Ser
385                 390                 395                 400

Ile Ala Lys Arg Gly Leu Val Lys Ser Phe Ser Leu Ala Gly Leu Ser
                405                 410                 415

Ala Pro Gln Val Ser Arg Thr Met Lys His Ser Val Ser Gln Tyr Ala
            420                 425                 430

Asp Ile Thr Tyr Met Pro Thr Asn Gly Lys Gln Ala Thr Ala Gly Glu
        435                 440                 445

Glu Ser Pro Lys Arg Asp Ala Lys Arg Gly Arg Tyr Glu Glu Glu Asn
    450                 455                 460

Leu Val Asn Leu Val Thr Met Glu Gly Ser Gln Ala Glu Ala Phe Gln
465                 470                 475                 480

Gly Thr Asn Gly Ile Gln Leu Arg Pro Glu Met Leu Cys Asp Trp Gly
                485                 490                 495

Cys Glu Thr Pro Arg Ile Tyr Tyr Glu Arg Tyr Met Gly Lys Asn Tyr
            500                 505                 510

Arg Tyr Phe Tyr Ala Ile Ser Ser Asp Val Asp Ala Val Asn Pro Gly
        515                 520                 525

Thr Leu Ile Lys Val Asp Val Trp Asn Lys Ser Cys Leu Thr Trp Cys
    530                 535                 540

Glu Glu Asn Val Tyr Pro Ser Glu Pro Ile Phe Val Pro Ser Pro Asp
545                 550                 555                 560

Pro Lys Ser Glu Asp Asp Gly Val Ile Leu Ala Ser Met Val Leu Gly
                565                 570                 575

Gly Leu Asn Asp Arg Tyr Val Gly Leu Ile Val Leu Cys Ala Lys Thr
            580                 585                 590

Met Thr Glu Leu Gly Arg Cys Asp Phe His Thr Asn Gly Pro Val Pro
        595                 600                 605

Lys Cys Leu His Gly Trp Phe Ala Pro Asn Ala Ile
610                 615                 620

<210> SEQ ID NO 8
<211> LENGTH: 1863
<212> TYPE: DNA
<213> ORGANISM: Artificial Sequence
<220> FEATURE:
<223> OTHER INFORMATION: Yarrowia codon-optimized DmNinaB
```

<400> SEQUENCE: 8

```
atggccgctg gtgttttcaa gtcttttatg cgagatttct ttgctgttaa gtacgatgag      60
cagcgaaacg acccccaggc cgagcgactg acggcaacg gacgactgta ccccaactgc     120
tcctctgatt tttggcttcg atcttgcgag cgagagatcg ttgacccat tgagggccac     180
cactccggtc acattcccaa gtggatttgc ggttccctgc tccgaaacgg ccccggctct     240
tggaaggttg gcgacatgac cttcggccac ctgttcgact gctccgccct gctccaccga     300
tttgccattc gaaacggacg agtcacctac cagaaccgat tgttgacac tgagactctg     360
cgaaagaacc gatctgccca gcgaattgtt gtcaccgagt ttggcactgc cgctgttccc     420
gatccctgtc actccatctt cgaccgattt gccgccattt ttcgacccga ttctggaacc     480
gataactcca tgatttccat ctaccccttc ggcgaccagt actacacttt caccgagact     540
ccctttatgc accgaattaa ccctgcact ctcgctactg aggctcgaat ctgcaccacc     600
gacttcgttg gcgttgtcaa ccacacttct cacccccacg ttcttccctc tggcactgtt     660
tacaacctgg gcaccactat gacccgatct ggacccgctt acactatcct ctctttcccc     720
cacggcgagc agatgttcga ggacgctcac gttgtcgcca ctctgccctg ccgatggaag     780
ctgcaccccg gttatatgca caccttcggc ctcactgacc actactttgt cattgttgag     840
cagccccttt ccgttccct cactgagtac atcaaggccc agcttggcgg acagaacctt     900
tccgcttgcc tcaagtggtt cgaggaccga cccactctct tcaccttat tgatcgagtt     960
tccggcaagc tggtccagac ctacgagtcc gaggctttct tctacctgca catcatcaac    1020
tgctttgagc gagatggcca cgttgtcgtt gacatttgct cttaccgaaa ccccgagatg    1080
attaactgca tgtacctgga ggccattgcc aacatgcaga ctaaccccaa ctacgctacc    1140
ctctttcgag acgacccct tcgattcgtc ctgcccctcg cactattcc cccgcctct     1200
atcgccaagc gaggactcgt caagtccttc tccctcgctg gactctccgc tccccaggtt    1260
tctcgaacca tgaagcactc cgtttctcag tacgccgata ttacctacat gcccaccaac    1320
ggaaagcagg ccactgctgg agaggagtcc cccaagcgag atgccaagcg aggccgatac    1380
gaggaggaga acctttgtcaa cctggttact atggagggct ctcaggccga ggcttttcag    1440
ggcaccaacg gcattcagct tcgacccgag atgctgtgtg attggggctg tgagactccc    1500
cgaatctact acgagcgata catgggcaag aactaccgat acttctacgc catttcttcc    1560
gatgttgatg ctgtcaaccc cggcaccctc atcaaggttg atgtctggaa caagtcttgt    1620
cttacctggt gcgaggagaa cgtctacccc tctgagccca ttttgtccc ctctcccgat    1680
cccaagtccg aggacgatgg cgttatcctg gcctctatgg ttcttggcgg tcttaacgac    1740
cgatacgtcg gccttattgt tctttgtgcc aagaccatga ccgagctggg ccgatgtgat    1800
ttccacacca acggacccgt tcccaagtgc ctccacggtt ggtttgctcc caacgccatt    1860
tag                                                                    1863
```

<210> SEQ ID NO 9
<211> LENGTH: 525
<212> TYPE: PRT
<213> ORGANISM: Danio rerio

<400> SEQUENCE: 9

```
Met Leu Ser Phe Phe Trp Arg Asn Gly Ile Glu Thr Pro Glu Pro Leu
1               5                   10                  15

Lys Ala Asp Val Ser Gly Ser Ile Pro Pro Trp Leu Gln Gly Thr Leu
            20                  25                  30
```

-continued

```
Leu Arg Asn Gly Pro Gly Leu Phe Ser Val Gly Asn Thr Ser Tyr Lys
         35                  40                  45

His Trp Phe Asp Gly Met Ala Leu Ile His Ser Phe Thr Phe Lys Asp
 50                  55                  60

Gly Glu Val Phe Tyr Arg Ser Lys Tyr Leu Lys Ser Glu Thr Tyr Lys
 65                  70                  75                  80

Lys Asn Ile Ala Ala Asp Arg Ile Val Val Ser Glu Phe Gly Thr Met
                 85                  90                  95

Val Tyr Pro Asp Pro Cys Lys Asn Ile Phe Ser Arg Ala Phe Ser Tyr
                100                 105                 110

Met Met Asn Ala Ile Pro Asp Phe Thr Asp Asn Asn Leu Ile Asn Ile
             115                 120                 125

Ile Lys Tyr Gly Glu Asp Tyr Tyr Ala Ser Ser Glu Val Asn Tyr Ile
         130                 135                 140

Asn Gln Ile Asp Pro Leu Thr Leu Glu Thr Leu Gly Arg Thr Asn Tyr
145                 150                 155                 160

Arg Asn His Ile Ala Ile Asn Leu Ala Thr Ala His Pro His Tyr Asp
                 165                 170                 175

Glu Glu Gly Asn Thr Tyr Asn Met Gly Thr Ala Ile Met Asn Leu Gly
             180                 185                 190

Arg Pro Lys Tyr Val Ile Phe Lys Val Pro Ala Asn Thr Ser Asp Lys
         195                 200                 205

Glu Asn Lys Lys Pro Ala Leu Ser Glu Val Gln Val Cys Ser Ile
         210                 215                 220

Pro Ile Arg Pro Ser Leu Tyr Pro Ser Tyr Phe His Ser Phe Gly Met
225                 230                 235                 240

Thr Glu Asn Tyr Ile Ile Phe Val Glu Gln Ala Phe Lys Leu Asp Ile
                 245                 250                 255

Val Lys Leu Ala Thr Ala Tyr Phe Arg Asp Ile Asn Trp Gly Ser Cys
             260                 265                 270

Leu Lys Phe Asp Gln Asp Ile Asn Val Phe His Leu Val Asn Lys
         275                 280                 285

Lys Thr Gly Lys Ala Val Ser Val Lys Tyr Tyr Thr Asp Pro Phe Val
         290                 295                 300

Thr Phe His His Ile Asn Ala Tyr Glu Asp Asp Gly His Val Val Phe
305                 310                 315                 320

Asp Leu Ile Thr Tyr Lys Asp Ser Lys Leu Tyr Asp Met Phe Tyr Ile
                 325                 330                 335

Gln Asn Met Lys Gln Asp Val Lys Arg Phe Ile Glu Thr Asn Lys Asp
             340                 345                 350

Phe Ala Gln Pro Val Cys Gln Arg Phe Val Leu Pro Val Asn Val Asp
         355                 360                 365

Lys Glu Thr Pro Gln Asp Ile Asn Leu Val Lys Leu Gln Asp Thr Thr
         370                 375                 380

Ala Thr Ala Val Leu Lys Glu Asp Gly Ser Val Tyr Cys Thr Pro Asp
385                 390                 395                 400

Ile Ile Phe Lys Gly Leu Glu Leu Pro Ala Ile Asn Tyr Lys Phe Asn
                 405                 410                 415

Ser Lys Lys Asn Arg Tyr Phe Tyr Gly Thr Arg Val Glu Trp Ser Pro
             420                 425                 430

Tyr Pro Asn Lys Val Ala Lys Val Asp Val Val Thr Arg Thr His Lys
         435                 440                 445
```

| | | | | | | | | | | | |
|---|---|---|---|---|---|---|---|---|---|---|---|
Ile Trp Thr Glu Glu Glu Cys Tyr Pro Ser Glu Pro Val Phe Ile Ala
    450                 455                 460

Ser Pro Asp Ala Val Asp Glu Asp Asp Gly Val Ile Leu Ser Ser Val
465                 470                 475                 480

Val Ser Phe Asn Pro Gln Arg Pro Pro Phe Leu Val Val Leu Asp Ala
                485                 490                 495

Lys Ser Phe Lys Glu Ile Ala Arg Ala Thr Ile Asp Ala Ser Ile His
                500                 505                 510

Met Asp Leu His Gly Leu Phe Ile His Asp Lys Ser Thr
                515                 520                 525

<210> SEQ ID NO 10
<211> LENGTH: 1578
<212> TYPE: DNA
<213> ORGANISM: Artificial Sequence
<220> FEATURE:
<223> OTHER INFORMATION: Yarrowia codon-optimized DrBCO

<400> SEQUENCE: 10

| | |
|---|---|
| atgctctctt tcttctggcg aaacggtatc gagaccccg agccctcaa ggctgacgtt | 60 |
| tccggctcta tccctccctg gcttcaggga acccttctcc gaaacggtcc tggtctgttc | 120 |
| tccgttggca acacttccta caagcactgg ttcgatggta tggctctcat tcactccttc | 180 |
| acctttaagg atggtgaggt tttttaccga tctaagtacc tgaagtctga gacttacaag | 240 |
| aagaacatcg ctgccgaccg aatcgttgtg tctgagttcg aaccatggt gtaccccgat | 300 |
| ccctgcaaga cattttctc ccgagccttc tcttacatga tgaacgccat tcctgacttt | 360 |
| accgataaca acctcattaa catcattaag tacggtgagg attactacgc tcctctgag | 420 |
| gtcaactaca tcaaccagat tgaccccctg acccttgaga ctctcggacg aactaactac | 480 |
| cgaaaccaca ttgccatcaa ccttgccact gctcaccctc actacgacga ggagggtaac | 540 |
| acttacaaca tgggcactgc tattatgaac ctcggtcgac ccaagtacgt gattttcaag | 600 |
| gtgcccgcca cacctctga taaggagaac aagaagcctg ccctctctga ggtggagcag | 660 |
| gtttgctcca ttcccatccg accctcccctt tacccttctt acttccactc ttttggcatg | 720 |
| actgagaact acatcatctt cgttgagcag gccttcaagc tggacatcgt caagctggct | 780 |
| actgcttact ccgagatat taactgggga tcttgcctta agttcgacca ggatgacatt | 840 |
| aacgtgttcc acctggtcaa caagaagact ggtaaggctg tgtccgtgaa gtactacact | 900 |
| gaccccttg ttaccttcca ccacatcaac gcttacgagg acgatggcca cgtcgtcttc | 960 |
| gatctcatta cttacaagga ctctaagctg tacgatatgt tctacattca gaacatgaag | 1020 |
| caggacgtca gcgatttat tgagactaac aaggacttcg ctcagcccgt gtgccagcga | 1080 |
| tttgtccttc ccgtcaacgt tgataaggag accctcagg acatcaacct tgtcaagctg | 1140 |
| caggacacca ctgccactgc tgtcctgaag gaggacggct ctgtcactg cacccctgac | 1200 |
| atcattttta agggtcttga gctccctgct atcaactaca gtttaactc taagaagaac | 1260 |
| cgatacttct acggcacccg agtggagtgg tccccttacc ctaacaaggt cgctaaggtg | 1320 |
| gacgttgtta ctcgaaccca caagatttgg actgaggagg agtgttaccc ttctgagcct | 1380 |
| gtcttattg cctccctga cgccgttgat gaggatgacg gtgtgattct tcttctgtg | 1440 |
| gtttctttca accccagcg accccctttc ctggttgtcc tcgatgctaa gtccttcaag | 1500 |
| gagattgctc gagctaccat cgatgcctct attcacatgg accttcacgg ccttttcatc | 1560 |
| cacgacaagt ctacctaa | 1578 |

<210> SEQ ID NO 11
<211> LENGTH: 281
<212> TYPE: PRT
<213> ORGANISM: Artificial Sequence
<220> FEATURE:
<223> OTHER INFORMATION: Danio rerio BCO TPI aa

<400> SEQUENCE: 11

```
Lys Gln Lys Ser Asn His Ile Leu Gln Tyr Ser Pro Val Ile Thr Ala
1               5                   10                  15

Ser Ile Thr Pro Val Gln Val Ser Leu Gly Phe Leu Phe Thr Asp Thr
            20                  25                  30

Val Ile Tyr Leu Thr Ile Ser Leu Gln Val Thr Gln Lys Val His Val
        35                  40                  45

Gly Asn Glu Pro Gln Thr Lys Thr Arg Tyr Asp Lys Ile Ala Leu Phe
    50                  55                  60

Asp Ala Glu Phe Asp Gly Val Ser Ile Gly Val Met Thr Phe Ile Cys
65                  70                  75                  80

Ile His Thr Lys Lys Ser Trp Trp Tyr Phe Cys Val Ile Thr Ser Asp
                85                  90                  95

Ile Tyr Ala Pro Pro Asn Pro Pro Ala Thr Val Lys Ser Val Ser Leu
            100                 105                 110

Leu Tyr Met Leu Thr Lys Pro Pro Thr Val Gln Arg Asn Pro Ser Ala
        115                 120                 125

Lys Ser His Asn Gln Leu Ile Thr Thr His Pro Met Thr Ser Pro Gln
    130                 135                 140

Ile Leu Tyr Ala Phe Arg His Tyr Tyr Ser Ser Leu Gln Arg Arg Cys
145                 150                 155                 160

Leu Arg Phe His Phe Cys Ser Ile Thr Ser Leu Asn Pro Tyr Arg Gln
                165                 170                 175

Ile Arg Pro Trp His Val Ser Arg Leu Ile Ser Pro Arg Val Leu His
            180                 185                 190

Gln Gly Gly Gly Val Arg Asn Thr Val Arg Ala His Ser Lys Gly Val
        195                 200                 205

Arg Val Arg Ala Ser Asp Asn Ile Ala Trp Thr Arg Arg His Ile Leu
    210                 215                 220

Asp Phe Trp Ala Arg Cys Ile His Leu Leu Arg Phe Pro Thr Leu Pro
225                 230                 235                 240

Pro Val Ser Pro Ser Gln Pro Ile Glu Gly Asn Leu Ile Arg Asp Thr
                245                 250                 255

Phe Val Ile His Ser Gln Ile Tyr Lys Gln Cys His Ser Pro Ser Tyr
            260                 265                 270

Ser Tyr Ile Gln His Asn Tyr Ile Gln
        275                 280
```

<210> SEQ ID NO 12
<211> LENGTH: 880
<212> TYPE: DNA
<213> ORGANISM: Artificial Sequence
<220> FEATURE:
<223> OTHER INFORMATION: Yarrowia codon-optimized DrBCO-TPI

<400> SEQUENCE: 12
aaacaaaaga gctgaaatca tatccttcag tagtagtata gtcctgttat cacagcatca      60 attaccccg tccaagtaag ttgattggga tttttgttta cagatacagt aatatacttg     120
actatttctt tacaggtgac tcagaaagtg catgttggaa atgagccaca gaccaagaca     180

-continued

```
agatatgaca aaattgcact attcgatgca gaattcgacg gtgtttccat tggtgttatg      240
acattcatct gcattcatac aaaaaagtct tggtagtggt acttttgcgt tattacctcc      300
gatatctacg cacccccaa cccccctgct acagtaaaga gtgtgagtct actgtacatg       360
cttactaaac cacctactgt acagcgaaac ccctcagcaa aatcacacaa tcagctcatt      420
acaacacacc caatgacctc accacaaatt ctatacgcct tttgacgcca ttattacagt      480
agcttgcaac gccgttgtct taggttccat ttttagtgct ctattacctc acttaacccg      540
tataggcaga tcaggccatg gcactaagtg tagagctaga ggttgatatc gccacgagtg      600
ctccatcagg gctagggtgg ggttagaaat acagtccgtg cgcactcaaa aggcgtccgg      660
gttagggcat ccgataatat cgcctggact cggcgccata ttctcgactt ctgggcgcgt      720
tgtattcatc tcctccgctt cccaacactt ccaccgttt ctccatccca accaatagaa       780
tagggtaacc ttattcggga cactttcgtc atacatagtc agatatacaa gcaatgtcac      840
tctccttcgt actcgtacat acaacacaac tacattcaaa                            880
```

```
<210> SEQ ID NO 13
<211> LENGTH: 531
<212> TYPE: PRT
<213> ORGANISM: Ictalurus punctatus

<400> SEQUENCE: 13

Met Glu Ala Ile Phe Cys Arg Asn Gly Thr Glu Thr Pro Glu Pro Val
1               5                   10                  15

Lys Ala Val Val Ser Gly Ala Ile Pro Pro Trp Leu Gln Gly Thr Leu
            20                  25                  30

Leu Arg Asn Gly Pro Gly Leu Phe Ser Ile Gly Lys Thr Ser Tyr Asn
        35                  40                  45

His Trp Phe Asp Gly Leu Ser Leu Ile His Ser Phe Thr Phe Lys His
    50                  55                  60

Gly Asp Val Tyr Tyr Arg Ser Lys Phe Leu Arg Ser Asp Thr Tyr Lys
65                  70                  75                  80

Lys Asn Ile Ala Ala Asn Arg Ile Val Val Ser Glu Phe Gly Thr Met
                85                  90                  95

Val Tyr Pro Asp Pro Cys Lys Asn Ile Phe Ser Lys Ala Phe Thr Tyr
            100                 105                 110

Leu Leu Asn Ser Ile Pro Asp Phe Thr Asp Asn Asn Leu Val Ser Ile
        115                 120                 125

Ile Lys Tyr Gly Asp Asp Tyr Tyr Thr Ser Ser Glu Ile Asn Tyr Ile
    130                 135                 140

Asn Gln Ile Asn Pro Val Thr Leu Asp Thr Ile Gly Arg Ala Asn Tyr
145                 150                 155                 160

Arg Asn Tyr Ile Ser Leu Asn Leu Ala Thr Ala His Pro His Tyr Asp
                165                 170                 175

Asp Glu Gly Asn Thr Tyr Asn Met Gly Thr Ala Ile Leu Ala Met Ser
            180                 185                 190

Gly Pro Lys Tyr Val Ile Phe Lys Val Pro Ala Thr Thr Ser Asp Ile
        195                 200                 205

Lys Asp Asn Gly Lys Thr Asn Leu Ala Leu Lys Asn Leu Gln Gln Ile
    210                 215                 220

Cys Ala Ile Pro Phe Arg Ser Lys Leu Tyr Pro Ser Tyr Tyr His Ser
225                 230                 235                 240

Phe Gly Met Thr Gln Asn Tyr Ile Ile Phe Val Glu Gln Pro Phe Lys
                245                 250                 255
```

```
Leu Asp Ile Ile Arg Leu Ala Thr Ala Tyr Phe Arg Thr Thr Trp
            260                 265                 270

Gly Lys Cys Leu Phe Tyr Asp Gln Asp Val Thr Leu Phe His Ile
        275                 280                 285

Ile Asn Arg Lys Thr Gly Asp Ala Val Asn Thr Lys Phe Tyr Gly Asp
    290                 295                 300

Ala Leu Val Val Phe His His Ile Asn Ala Tyr Glu Glu Asp Gly His
305                 310                 315                 320

Ile Val Phe Asp Leu Ile Ser Tyr Lys Asp Ser Ser Leu Tyr Asp Leu
                325                 330                 335

Phe Tyr Ile Asp Tyr Met Lys Gln Glu Ala Pro Lys Phe Thr Glu Thr
            340                 345                 350

Ser Lys Ala Phe Ser Arg Pro Val Cys Gln Arg Phe Val Ile Pro Leu
        355                 360                 365

Asn Ala Asp Leu Lys Gly Asn Pro Leu Gly Lys Asn Leu Val Arg Leu
    370                 375                 380

Glu Asp Thr Ser Ala Thr Ala Val Phe Gln Met Asp Gly Ser Leu Tyr
385                 390                 395                 400

Cys Thr Pro Glu Thr Leu Phe Gln Gly Leu Glu Leu Pro Ser Ile Asn
                405                 410                 415

Tyr Gln Tyr Asn Gly Lys Lys Tyr Arg Tyr Phe Tyr Gly Ser Met Met
            420                 425                 430

Asp Trp Ser Pro Gln Ala Asn Lys Ile Ala Lys Val Asp Val Asp Thr
        435                 440                 445

Lys Thr His Leu Glu Trp Thr Glu Glu Asp Cys Tyr Pro Ser Glu Pro
450                 455                 460

Lys Phe Val Ala Ser Pro Gly Ala Val Asp Glu Asp Asn Gly Val Ile
465                 470                 475                 480

Leu Ser Ser Val Val Ser Val Asn Pro Lys Lys Ser Pro Phe Met Leu
                485                 490                 495

Val Leu Asp Ala Lys Thr Leu Lys Glu Ile Ala Arg Ala Ser Ile Asp
            500                 505                 510

Ala Thr Val His Leu Asp Leu His Gly Ile Phe Ile Pro Gln Glu Thr
        515                 520                 525

Glu Leu Lys
    530

<210> SEQ ID NO 14
<211> LENGTH: 1596
<212> TYPE: DNA
<213> ORGANISM: Artificial Sequence
<220> FEATURE:
<223> OTHER INFORMATION: Yarrowia codon-optimized IpBCO

<400> SEQUENCE: 14
atggaggcca tttctgtcg aaacggcacc gagactcccg agcccgtcaa ggctgttgtg      60
tccggtgcta tcccccttg gcttcaggga acccttctcc gaaacggacc cggccttttc      120
tccattggta agacttccta caaccactgg tttgacggac tctctcttat tcactctttc      180
acctttaagc acggtgatgt ttactaccga tctaagttcc tccgatccga tacctacaag      240
aagaacattg ctgccaaccg aatcgttgtg tctgagtttg cactatggt ctaccccgat      300 ccctgcaaga acattttctc taaggccttc acttacctgc tcaactctat tccgatttc      360 accgacaaca accttgtctc tattattaag tacggcgatg actactacac ttcttccgag      420
attaactaca tcaaccagat caacccgtt actctcgaca ctattggacg agccaactac      480
```

-continued

```
cgaaactaca tttcccttaa ccttgctact gcccaccctc actacgatga cgagggaaac    540
acctacaaca tgggcactgc tatcctggct atgtctggac ccaagtacgt catcttcaag    600
gtgcccgcta ctacctctga tattaaggac aacggaaaga ctaaccttgc tctgaagaac    660
ctgcagcaga tctgcgccat tcctttccga tctaagctct acccttctta ctaccactcc    720
tttggtatga ctcagaacta catcattttc gttgagcagc ccttcaagct ggacattatt    780
cgactggcca ctgcttactt ccgacgaacc acctggggca agtgcctctt ttacgaccag    840
gacgatgtta ctctcttcca cattatcaac cgaaagactg gtgacgccgt gaacactaag    900
ttctacggtg atgctctcgt ggttttccac cacatcaacg cctacgagga ggacggccac    960
atcgtttttg acctgatctc ttacaaggac tcttctctct acgaccttt  ctacattgac   1020 tacatgaagc aggaggctcc taagttcact gagacttcca aggcttttc  tcgacccgtc   1080 tgtcagcgat tcgtcatccc tctcaacgct gacctcaagg gaaaccccct gggcaagaac   1140
cttgtccgac ttgaggacac ttctgctacc gctgtgttcc agatggacgg ttccctgtac   1200
tgtactcccg agactctctt tcagggtctt gagctcccct tccattaacta ccagtacaac   1260 ggaaagaagt accgatactt ctacggctct atgatggatt ggtcccctca ggctaacaag   1320
atcgctaagg tggacgttga taccaagact caccttgagt ggaccgagga ggattgctac   1380
ccttctgagc ctaagtttgt cgcttcccct ggcgctgtcg atgaggataa cggtgtgatc   1440
ctgtcttctg ttgtctccgt caaccccaag aagtccccct ttatgctcgt gctcgatgct   1500
aagaccctca aggagatcgc tcgagcctct attgacgcca ctgttcacct cgacctccac   1560 ggaatttttca tccctcagga gactgagctt aagtaa                             1596
```

<210> SEQ ID NO 15
<211> LENGTH: 527
<212> TYPE: PRT
<213> ORGANISM: Esox lucius

<400> SEQUENCE: 15

```
Met Ala Gln Ile Ile Phe Gly Lys Asn Gly Thr Glu Ser Pro Glu Pro
1               5                   10                  15

Val Lys Ala Glu Ile Thr Gly Cys Ile Pro Glu Trp Leu Gln Gly Thr
            20                  25                  30

Leu Leu Arg Asn Gly Pro Gly Leu Phe Lys Val Gly Asp Thr Glu Tyr
        35                  40                  45

Asn His Trp Phe Asp Gly Met Ala Leu Ile His Ser Phe Thr Phe Lys
    50                  55                  60

Asp Gly Asp Val Tyr Tyr Arg Ser Lys Phe Leu Arg Ser Asp Thr Phe
65                  70                  75                  80

Gln Lys Asn Thr Lys Ala Asn Lys Ile Val Val Ser Glu Phe Gly Thr
                85                  90                  95

Met Ile Tyr Pro Asp Pro Cys Lys Asn Met Phe Ser Lys Ala Phe Ser
            100                 105                 110

Tyr Leu Leu Ala Ala Ile Pro Asp Phe Thr Asp Asn Asn Leu Ile Asn
        115                 120                 125

Ile Ile Arg Tyr Gly Glu Asp Tyr Tyr Ala Ser Ser Glu Ile Asn Tyr
    130                 135                 140

Ile Asn Gln Ile Asp Pro Val Thr Leu Glu Val Ile Gly Lys Met Asn
145                 150                 155                 160

Tyr Arg Lys His Ile Ser Leu Asn Leu Ala Thr Ala His Pro His Tyr
                165                 170                 175
```

```
Asp Glu Glu Gly Asn Thr Tyr Asn Met Gly Ile Ala Leu Met Arg Phe
                180                 185                 190
Gly Met Pro Lys Tyr Val Ile Phe Lys Val Pro Val Asp Ala Ser Asp
            195                 200                 205
Lys Glu Gly Lys Lys Pro Ala Leu Glu Glu Val Glu Gln Val Cys Asn
210                 215                 220
Ile Pro Phe Arg Ser Thr Leu Phe Pro Ser Tyr Phe His Ser Phe Gly
225                 230                 235                 240
Met Ser Glu Asn Tyr Ile Ile Phe Val Glu Gln Pro Phe Lys Leu Asp
                245                 250                 255
Ile Leu Arg Leu Ala Thr Ala Asn Phe Arg Gly Ser Thr Trp Gly Ser
            260                 265                 270
Cys Leu Lys Tyr Asp Lys Glu Asp Ile Thr Leu Ile His Leu Val Asp
            275                 280                 285
Lys Lys Thr Gly Lys Ala Val Ser Thr Lys Phe Tyr Ala Asp Ala Leu
290                 295                 300
Val Val Phe His His Ile Asn Ala Tyr Glu Asp Asp Asn His Val Val
305                 310                 315                 320
Phe Asp Met Ile Thr Tyr Lys Asp Ser Asn Leu Tyr Glu Met Phe Tyr
                325                 330                 335
Leu Ala Asn Met Arg Glu Glu Ser Asn Lys Phe Ile Glu Asp Lys Val
            340                 345                 350
Asn Phe Ser Gln Pro Ile Cys Gln Arg Phe Val Leu Pro Leu Asn Val
            355                 360                 365
Asp Lys Asp Thr Thr Lys Gly Thr Asn Met Val Met Leu Lys Asn Thr
370                 375                 380
Thr Ala Lys Ala Val Met Gln Asp Asp Gly Ser Val Tyr Cys Lys Pro
385                 390                 395                 400
Asp Thr Ile Phe Ala Gly Leu Glu Leu Pro Gly Ile Asn Tyr Lys Phe
                405                 410                 415
Asn Gly Lys Lys Tyr Arg Tyr Phe Tyr Gly Ser Arg Val Glu Trp Thr
            420                 425                 430
Pro Phe Pro Asn Lys Ile Gly Lys Val Asp Ile Leu Thr Lys Lys His
            435                 440                 445
Ile Glu Trp Thr Glu Glu Cys Tyr Pro Ser Glu Pro Val Phe Val
450                 455                 460
Ala Ser Pro Gly Ala Met Glu Glu Asp Asp Gly Val Ile Leu Ser Ser
465                 470                 475                 480
Ile Val Ser Leu Asn Pro Asn Lys Ser Pro Phe Met Leu Val Leu Asn
                485                 490                 495
Ala Lys Asn Phe Glu Glu Ile Ala Arg Ala Ser Ile Asp Ala Ser Val
            500                 505                 510
His Leu Asp Leu His Gly Leu Phe Ile Pro Ser Gln Lys Thr Asn
            515                 520                 525

<210> SEQ ID NO 16
<211> LENGTH: 1584
<212> TYPE: DNA
<213> ORGANISM: Artificial Sequence
<220> FEATURE:
<223> OTHER INFORMATION: Yarrowia codon-optimized E1BCO

<400> SEQUENCE: 16
atggctcaga ttattttggg caagaacggc actgagtctc ctgagcctgt caaggccgag      60
attaccggat gtatccctga gtggctccag ggtactctcc ttcgaaacgg tcccggtctt     120
```

```
ttcaaggtgg gtgataccga gtacaaccac tggttcgatg gcatggccct gattcactct    180
tttaccttca aggatggtga cgtgtactac cgatctaagt ccttcgatc cgacaccttc     240 cagaagaaca ctaaggctaa caagattgtt gtgtctgagt ttggcaccat gatttaccct    300 gaccccctgca agaacatgtt ttccaaggct ttctcctacc tccttgctgc catccctgac   360
ttcaccgata caacctgat taacattatc cgatacggtg aggactacta cgcctcttcc    420
gagatcaact acatcaacca gattgaccct gttaccctgg aggtgattgg aaagatgaac    480
taccgaaagc acatttctct gaaccttgct actgcccacc tcactacga cgaggaggga    540 aacacttaca acatgggaat cgccctcatg cgatttggca tgcccaagta cgtcatcttc    600
aaggttcctg tcgatgcttc tgataaggag ggcaagaagc ctgcccttga ggaggtggag    660
caggtctgca acattccctt tcgatctacc ctcttcccct cttacttcca ctcttttggc    720
atgtctgaga actacatcat ctttgtcgag cagccttca agctggacat cctccgactg     780
gccactgcta acttccgagg atctacctgg ggttcctgcc tgaagtacga caaggaggac    840
attactctca tccacctggt cgacaagaag actggtaagg ctgtttccac caagttctac    900
gctgatgctc tggttgtttt ccaccacatt aacgcctacg aggacgacaa ccacgtggtt    960
ttcgatatga tcacctacaa ggactccaac ctgtacgaga tgttctacct tgctaacatg    1020
cgagaggagt ctaacaagtt cattgaggac aaggtcaact tctcccagcc tatctgccag    1080
cgatttgtcc tccccctcaa cgttgacaag ataccacta agggaaccaa catggtgatg     1140
ctcaagaaca ctaccgccaa ggccgtgatg caggatgacg gctctgtgta ctgcaagcct    1200
gacaccattt ttgctggtct tgagctccct ggcattaact acaagttcaa cggcaagaag    1260
taccgatact tttacggctc tcgagtggag tggactccct ccctaacaa gattggaaag     1320 gtggacattc tgaccaagaa gcacattgag tggaccgagg aggagtgtta ccctctgag     1380 cccgttttg ttgcctcccc cggagctatg gaggaggatg acggagtcat tctttcttct    1440
attgtctctc tcaaccctaa caagtccccc ttcatgcttg tcctcaacgc taagaacttt    1500
gaggagattg ctcgagcctc catcgatgcc tctgttcacc tcgatctcca cggactcttc    1560
attccctctc agaagactaa ctag                                           1584
```

<210> SEQ ID NO 17
<211> LENGTH: 531
<212> TYPE: PRT
<213> ORGANISM: Latimeria chalumnae

<400> SEQUENCE: 17

Met Gln Ser Leu Phe Gly Lys Asn Lys Arg Glu Cys Pro Glu Pro Ile
1               5                   10                  15

Lys Ala Glu Val Lys Gly Gln Ile Pro Ala Trp Leu Gln Gly Thr Leu
                20                  25                  30

Leu Arg Asn Gly Pro Gly Met His Thr Val Gly Glu Thr Ser Tyr Asn
            35                  40                  45

His Trp Phe Asp Gly Leu Ala Leu Met His Ser Phe Thr Phe Lys Asp
        50                  55                  60

Gly Glu Val Phe Tyr Gln Ser Lys Tyr Leu Arg Ser Asp Thr Tyr Lys
65                  70                  75                  80

Lys Asn Met Glu Ala Asn Arg Ile Val Val Ser Glu Phe Gly Thr Met
                85                  90                  95

Ala Tyr Pro Asp Pro Cys Lys Asn Ile Phe Ser Lys Ala Phe Ser Tyr
            100                 105                 110

-continued

```
Leu Ser His Thr Ile Pro Glu Phe Thr Asp Asn Cys Leu Ile Asn Ile
        115                 120                 125

Met Lys Cys Gly Glu Asp Tyr Tyr Ala Val Thr Glu Thr Asn Phe Ile
130                 135                 140

Arg Lys Ile Asp Pro Lys Ser Leu Asp Thr Leu Glu Lys Val Asp Tyr
145                 150                 155                 160

Thr Lys Tyr Ile Ala Leu Asn Leu Ala Ser Ser His Pro His Tyr Asp
                165                 170                 175

Ala Ala Gly Asp Thr Ile Asn Met Gly Thr Ser Ile Ala Asp Lys Gly
                180                 185                 190

Lys Thr Lys Tyr Leu Ile Val Lys Ile Pro Asn Met Lys Pro Val Glu
        195                 200                 205

Ser Glu Lys Lys Lys Val Tyr Phe Lys Asn Leu Glu Val Leu Cys
        210                 215                 220

Ser Ile Pro Ser His Gly Arg Leu Asn Pro Ser Tyr Tyr His Ser Phe
225                 230                 235                 240

Gly Ile Thr Glu Asn Tyr Ile Val Phe Val Glu Gln Pro Phe Lys Leu
                245                 250                 255

Asp Leu Leu Lys Leu Ala Thr Ala Tyr Phe Arg Gly Ile Asn Trp Ala
                260                 265                 270

Ser Cys Leu Asn Phe His Ser Glu Asp Lys Thr Phe Ile His Ile Ile
        275                 280                 285

Asp Arg Arg Thr Lys Thr Ser Val Ser Thr Lys Phe His Thr Asp Ala
        290                 295                 300

Leu Val Leu Tyr His His Val Asn Ala Tyr Glu Glu Asp Gly His Val
305                 310                 315                 320

Val Phe Asp Val Ile Ala Tyr Asn Asp Ser Ser Leu Tyr Asp Met Phe
                325                 330                 335

Tyr Leu Ala Asn Val Arg Gln Glu Ser Ala Glu Phe Glu Ala Lys Asn
                340                 345                 350

Thr Ser Ser Ser Lys Pro Ala Cys Arg Arg Phe Val Ile Pro Leu Gln
        355                 360                 365

Pro Asp Lys Asp Ala Glu Leu Gly Thr Asn Leu Val Lys Leu Ala Ser
        370                 375                 380

Thr Thr Ala Asp Ala Ile Lys Glu Lys Asp Ser Ile Tyr Cys His Pro
385                 390                 395                 400

Glu Ile Leu Val Glu Asp Ile Glu Leu Pro Arg Ile Asn Tyr Asn Tyr
                405                 410                 415

Asn Gly Lys Lys Tyr Arg Tyr Ile Tyr Val Thr Gly Ile Ala Trp Lys
                420                 425                 430

Pro Ile Pro Thr Lys Ile Val Lys Phe Asp Thr Leu Thr Arg Lys Ser
        435                 440                 445

Val Glu Trp Gln Glu Glu Asp Cys Trp Pro Ala Glu Pro Val Phe Val
        450                 455                 460

Pro Ser Pro Asp Ala Lys Glu Glu Asp Gly Ile Val Leu Ser Ser
465                 470                 475                 480

Ile Val Cys Thr Ser Pro Asn Lys Phe Pro Phe Leu Leu Ile Leu Asp
                485                 490                 495

Ala Lys Thr Phe Thr Glu Leu Ala Arg Ala Ser Ile Asn Ala Asp Val
                500                 505                 510
```

His Leu Asp Leu His Gly Tyr Phe Ile Pro Glu Lys Lys Lys Ala Gln
    515                 520                 525

Ile Thr His
    530

<210> SEQ ID NO 18
<211> LENGTH: 1596
<212> TYPE: DNA
<213> ORGANISM: Artificial Sequence
<220> FEATURE:
<223> OTHER INFORMATION: Yarrowia codon-optimized LcBCO

<400> SEQUENCE: 18

| | | |
|---|---|---|
| atgcagtctc tgttcggtaa gaacaagcga gagtgtcctg agcccattaa ggctgaggtg | 60 |
| aagggtcaga ttcctgcttg gctccagggt actctccttc gaaacggccc tggcatgcac | 120 |
| accgttggcg agacttctta caaccactgg ttcgacggac tcgctcttat gcactccttc | 180 |
| acctttaagg atggtgaggt tttttaccag tctaagtacc tgcgatccga cacctacaag | 240 |
| aagaacatgg aggccaaccg aattgtcgtg tctgagttcg aaccatggc ctaccccgat | 300 |
| ccctgcaaga acattttttc caaggctttt tcttaccttt ctcacaccat ccctgagttt | 360 |
| accgacaact gtctgatcaa cattatgaag tgtggtgagg attactacgc tgttactgag | 420 |
| actaacttca tccgaaagat tgatcccaag tccctcgaca ccctggagaa ggttgactac | 480 |
| accaagtaca ttgctcttaa cctggcttcc tcccacccc actacgatgc tgctggtgat | 540 |
| accattaaca tgggcacctc tatcgctgat aagggaaaga ctaagtacct gattgttaag | 600 |
| attcccaaca tgaagcccgt tgagtctgag aagaagaaga aggtctactt taagaacctg | 660 |
| gaggtgctct gctccatccc ttctcacgga cgacttaacc cttcttacta ccactccttt | 720 |
| ggcatcactg agaactacat cgttttcgtg gagcagccct ttaagctgga ccttctcaag | 780 |
| ctggccaccg cctacttccg aggtattaac tgggcctctt gtcttaactt ccactccgag | 840 |
| gacaagactt tcattcacat catcgatcga cgaaccaaga cctccgtttc cactaagttt | 900 |
| cacaccgatg ctctcgttct ttaccaccac gtcaacgctt acgaggagga tggccacgtt | 960 |
| gttttcgatg tcattgccta caacgactct tctctctacg atatgtttta cctcgccaac | 1020 |
| gttcgacagg agtctgccga gtttgaggct aagaacacct cttcctccaa gcctgcttgt | 1080 |
| cgacgatttg tcattcccct gcagcctgac aaggatgctg agctgggcac taacctggtc | 1140 |
| aagctcgctt ccactaccgc cgacgccatt aaggagaagg actccatttta ctgccaccct | 1200 |
| gagatcctgg ttgaggatat tgagctccct cgaattaact acaactacaa cggcaagaag | 1260 |
| taccgataca tttacgttac tggtatcgcc tggaagccca ttcccactaa gattgtcaag | 1320 |
| tttgacactc tcactcgaaa gtccgtggag tggcaggagg aggactgttg gcccgccgag | 1380 |
| cctgtctttg ttccttcccc cgatgccaag gaggaggacg atggtattgt ctttcttcc | 1440 |
| atcgtgtgta cttcccctaa caagtttccc ttcctcctta ttctggacgc caagaccttt | 1500 |
| accgagctcg ctcgagcttc tattaacgcc gatgtccacc tcgaccttca cggatacttt | 1560 |
| atccctgaga agaagaaggc ccagatcacc cactag | 1596 |

<210> SEQ ID NO 19
<211> LENGTH: 325
<212> TYPE: PRT
<213> ORGANISM: Fusarium fujikuroi

<400> SEQUENCE: 19

```
Met Thr Thr Lys Tyr Thr Ser Val His Glu Ser Pro Asn Gly Pro Gly
1               5                   10                  15

Asp Ala Arg Pro Thr Ala Ser Gln Ile Ile Asp Asp Tyr Asn Leu Glu
            20                  25                  30

Gly Glu Leu Ser Gly Lys Thr Val Leu Val Thr Gly Cys Ser Ser Gly
        35                  40                  45

Ile Gly Val Glu Thr Ala Arg Ala Ile Tyr Arg Thr Gly Ala Thr Leu
    50                  55                  60

Tyr Leu Thr Ala Arg Asp Val Asp Lys Ala Lys Thr Val Leu Pro Asp
65                  70                  75                  80

Leu Val Asp Thr Ser Arg Val His Phe Leu His Leu Asp Leu Asn Ser
                85                  90                  95

Leu Glu Ser Val Arg Gly Phe Ala Glu Asn Phe Lys Ser Lys Ser Thr
            100                 105                 110

Gln Leu His Ile Leu Ile Glu Asn Ala Gly Val Met Ala Cys Pro Glu
        115                 120                 125

Gly Arg Thr Val Asp Gly Phe Glu Thr Gln Phe Gly Ile Asn His Leu
    130                 135                 140

Ala His Phe Leu Leu Phe Tyr Leu Leu Lys Asp Thr Leu Leu Asn Ser
145                 150                 155                 160

Ser Thr Pro Ala Phe Asn Ser Arg Val Val Ile Leu Ser Ser Cys Ala
                165                 170                 175

His Gln Ala Gly Ser Val His Leu Asn Asn Leu Ser Leu Glu Gly Gly
            180                 185                 190

Tyr Glu Pro Trp Lys Ser Tyr Gly Gln Ser Lys Thr Ala Asn Leu Trp
        195                 200                 205

Thr Ala Arg Glu Ile Glu Lys Arg Phe Gly Ala Ser Gly Ile His Ser
    210                 215                 220

Trp Ala Val His Pro Gly Ser Ile Ala Thr Glu Leu Gln Arg His Val
225                 230                 235                 240

Ser Asp Glu Leu Lys Gln Lys Trp Ala Asp Asp Lys Glu Gly Ala Lys
                245                 250                 255

Leu Trp Lys Ser Thr Glu Gln Gly Ala Ala Thr Thr Val Leu Ala Ala
            260                 265                 270

Val Ser Pro Glu Leu Glu Gly Lys Gly Gly Leu Tyr Leu Glu Asp Thr
        275                 280                 285

Gln Val Ala Lys Pro Pro Ala Arg Gly Met Phe Gly Val Ala Asp Trp
    290                 295                 300

Ala Tyr Asp Glu Asp Gly Pro Ser Lys Leu Trp Ala Lys Ser Leu Glu
305                 310                 315                 320

Leu Leu Lys Leu Gln
            325
```

<210> SEQ ID NO 20
<211> LENGTH: 978
<212> TYPE: DNA
<213> ORGANISM: Artificial Sequence
<220> FEATURE:
<223> OTHER INFORMATION: Yarrowia codon-optimized FfRDH12

<400> SEQUENCE: 20

```
atgaccacta agtacacttc cgttcacgag tctcccaacg gccctggtga cgctcgaccc      60
accgcttccc agattatcga cgattacaac cttgagggag agctttctgg caagactgtt     120
```

```
ctcgtcaccg gctgttcctc tggtattggt gttgagactg cccgagctat ttaccgaact    180
ggtgccaccc tttacctcac tgcccgagat gtcgataagg ccaagaccgt tcttcccgac    240
cttgttgaca cttcccgagt ccactttctc caccttgacc ttaactctct ggagtctgtt    300
cgaggttttg ctgagaactt caagtctaag tccactcagc ttcacattct catcgagaac    360
gctggcgtga tggcctgtcc cgagggccga accgtcgatg gttttgagac tcagtttggt    420
atcaaccacc ttgctcactt tctcctcttt tacctcctca aggataccct tctcaactct    480
tctacccccg ctttcaactc ccgagttgtc atcctctctt cttgtgctca ccaggctggt    540
tccgttcacc ttaacaacct gtctcttgag ggtggatacg agccttggaa gtcttacggc    600
cagtccaaga ctgccaacct ttggactgcc cgagagatcg agaagcgatt tggtgcttcc    660
ggtatccact ttgggctgt tcaccccggt tccatcgcta ctgagcttca gcgacacgtt    720
tccgacgagc ttaagcagaa gtgggctgac gataaggagg gtgccaagct gtggaagtcc    780
accgagcagg gtgccgccac cactgtcctt gctgctgttt ccctgagct tgagggtaag    840 ggcggtcttt accttgagga tacccaggtt gccaagcccc ctgcccgagg aatgtttggt    900
gttgctgact gggcttacga tgaggatggc ccctctaagc tctgggccaa gtctcttgag    960
ctccttaagc tccagtaa                                                  978

<210> SEQ ID NO 21
<211> LENGTH: 525
<212> TYPE: PRT
<213> ORGANISM: Saccharomyces bayanus

<400> SEQUENCE: 21

Met Asn Thr Tyr Ser Glu Lys Thr Ser Leu Val Gln Asp Glu Cys Leu
1               5                   10                  15

Ala Lys Met Ile Gln Asn Gly His Ser Arg Arg Met Gly Ser Val Glu
            20                  25                  30

Asp Leu Tyr Ala Ala Leu Asn Arg Gln Lys Leu Tyr Arg Asn Phe Ser
        35                  40                  45

Thr Tyr Ser Glu Leu Asn Asp Tyr Cys Thr Lys Asp Gln Leu Ala Leu
    50                  55                  60

Ala Leu Arg Asn Ile Cys Leu Lys Asn Pro Thr Leu Leu His Ile Val
65                  70                  75                  80

Leu Pro Ala Arg Trp Pro Asp His Glu Asn Tyr Tyr Leu Ser Ser Glu
                85                  90                  95

Tyr Tyr Ser Gln Pro His Pro Lys His Asp Tyr Ile Ser Val Leu Pro
            100                 105                 110

Glu Leu Lys Phe Asp Gly Val Ile Leu Asn Glu Gln Pro Glu His Asn
        115                 120                 125

Ala Leu Met Lys Gln Ile Leu Glu Glu Leu Lys Asp Ser Asn Gly Ser
    130                 135                 140

Tyr Thr Ala Lys Ile Phe Lys Leu Thr Thr Ala Leu Thr Ile Pro Tyr
145                 150                 155                 160

Ala Gly Pro Thr Ser Pro Thr Trp Arg Leu Ile Cys Leu Pro Glu Glu
                165                 170                 175

Gly Tyr Thr Asp Lys Trp Lys Lys Phe Ile Phe Leu Ser Asn His Cys
            180                 185                 190

Met Cys Asp Gly Arg Thr Ser Ile His Phe Phe Gln Asp Leu Arg Asp
        195                 200                 205

Glu Leu Asn Asn Ile Lys Thr Pro Pro Lys Lys Leu Asp Tyr Ile Phe
    210                 215                 220
```

Gln Tyr Glu Lys Asp Tyr Gln Leu Leu Arg Lys Leu Pro Glu Pro Ile
225                 230                 235                 240

Glu Asn Met Ile Asp Phe Arg Pro Pro Tyr Met Phe Ile Pro Lys Ser
            245                 250                 255

Leu Ile Ser Gly Phe Ile Tyr Ser His Leu Arg Phe Ser Ser Lys Gly
        260                 265                 270

Val Cys Thr Arg Met Asp Glu Leu Glu Lys Asn Asp Asp Ile Val Thr
    275                 280                 285

Glu Ile Ile Thr Ile Ser Pro Ser Glu Leu Gln Lys Ile Arg Thr Lys
290                 295                 300

Ile Lys Ser Asn Ile Pro Gly Lys Cys Thr Ile Thr Pro Phe Leu Glu
305                 310                 315                 320

Val Cys Trp Phe Val Ser Leu His Lys Trp Gly Lys Phe Phe Lys Pro
            325                 330                 335

Leu Lys Phe Glu Trp Leu Thr Asp Val Phe Ile Pro Ala Asp Cys Arg
        340                 345                 350

Ser Leu Leu Pro Glu Asp Glu Asp Val Arg Ala Met Tyr Arg Tyr Gly
    355                 360                 365

Ala Asn Val Gly Phe Val Asp Phe Thr Pro Trp Ile Ser Glu Phe Asn
370                 375                 380

Met Asn Asp Ser Lys Glu Asn Phe Trp Pro Leu Ile Ala His Tyr His
385                 390                 395                 400

Glu Val Ile Ser Gly Ala Ile Asn Asp Lys Lys His Leu Asn Gly Leu
            405                 410                 415

Gly Phe Asn Ile Gln Gly Leu Val Gln Lys Tyr Val Asn Ile Asp Lys
        420                 425                 430

Val Met Arg Asp Arg Ala Leu Gly Lys Ser Arg Gly Gly Thr Leu Leu
    435                 440                 445

Ser Asn Val Gly Ile Phe His Gln Ser Glu Glu Thr Asp Ser Arg Tyr
450                 455                 460

Ser Ile Arg Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
            485                 490                 495

Val Ile Ser Ser Thr Lys Asn Ala Val Gly Ser Gln Glu Leu Leu Glu
        500                 505                 510

Glu Leu Cys Ala Met Tyr Lys Ala Leu Leu Leu Asp Pro
    515                 520                 525

<210> SEQ ID NO 22
<211> LENGTH: 1578
<212> TYPE: DNA
<213> ORGANISM: Artificial Sequence
<220> FEATURE:
<223> OTHER INFORMATION: Yarrowia codon-optimized SbATF1

<400> SEQUENCE: 22
atgaacacct actctgagaa gacctctctt gttcaggacg agtgtctggc taagatgatt    60
cagaacggtc actctcgacg aatgggctct gtcgaggacc tttacgccgc cctcaaccga   120
cagaagctct accgaaactt ctctacttac tctgagctga cgattactg cactaaggat   180 cagctcgctc ttgctctccg aaacatttgt ctgaagaacc ccactctcct tcacattgtt   240
cttcccgctc gatggcccga tcacgagaac tactaccttt cttctgagta ctactctcag   300
ccccacccca agcacgatta catctctgtt cttcccgagc tgaagttcga tggtgtgatt   360

-continued

| | |
|---|---|
| ctcaacgagc agcccgagca caacgccctt atgaagcaga ttcttgagga gcttaaggat | 420 |
| tccaacggtt cttacactgc taagattttc aagctcacta ccgctctcac tattccctac | 480 |
| gctggtccca cttctcccac ttggcgactg atttgtctgc ccgaggaggg atacaccgat | 540 |
| aagtggaaga agtttatttt cctttccaac cactgcatgt gtgatggtcg aacctctatt | 600 |
| cacttctttc aggatctccg agatgagctt aacaacatca agactccccc caagaagctc | 660 |
| gactacattt tccagtacga aaggactac cagcttctcc gaaagctccc cgagcccatt | 720 |
| gagaacatga ttgattttcg acccccctac atgtttattc ccaagtccct tatttccggc | 780 |
| ttcatttact cccaccttcg attctcctct aagggtgtgt gtacccgaat ggacgagctt | 840 |
| gagaagaacg acgatattgt tactgagatc atcaccatct ctccctctga gcttcagaag | 900 |
| attcgaacta agatcaagtc taacattccc ggcaagtgca ccatcactcc cttccttgag | 960 |
| gtttgttggt ttgtttctct ccacaagtgg ggcaagtttt tcaagcccct caagttcgag | 1020 |
| tggcttaccg atgttttat tcccgctgat tgccgatctc tgctccccga ggacgaggac | 1080 |
| gtgcgagcta tgtaccgata cggcgctaac gtcggttttg ttgacttcac tcctggatt | 1140 |
| tctgagttta acatgaacga ctctaaggag aacttctggc cccttattgc tcactaccac | 1200 |
| gaggttattt ctggtgccat caacgacaag aagcacctca acggtcttgg tttcaacatt | 1260 |
| cagggccttg tccagaagta cgtcaacatt gacaaggtga tgcgagatcg agcccttggt | 1320 |
| aagtcccgag gaggcaccct gctctctaac gtgggtattt tccaccagtc tgaggagact | 1380 |
| gactcccgat actctatccg agacctcgct ttcggtcagt ttcagggttc ttggcaccag | 1440 |
| gctttctctc tcggtgtttg ttccactaac gtgaagggaa tgaacattgt tatttcttcc | 1500 |
| actaagaacg ccgtgggttc ccaggagctc cttgaggagc tttgtgccat gtacaaggct | 1560 |
| ctgctccttg acccctaa | 1578 |

<210> SEQ ID NO 23
<211> LENGTH: 391
<212> TYPE: PRT
<213> ORGANISM: Fragaria x ananassa

<400> SEQUENCE: 23

Met Ser Tyr Lys Asn Asn His Ser Ile Leu Ser Lys Pro Asn Asp Pro
1               5                   10                  15

Val Glu Val Ile Arg Asp Ala Leu Ser Lys Ala Leu Gln Phe Tyr Tyr
            20                  25                  30

Pro Leu Ala Gly Arg Leu Arg Glu Gly Pro Asn Lys Lys Leu Met Val
        35                  40                  45

Asp Cys Thr Gly Glu Gly Ile Leu Phe Val Glu Ala Asn Ala Glu Val
    50                  55                  60

Thr Leu Asp Glu Leu Gly Asp Ala Ile Leu Pro Cys Pro Phe Leu
65                  70                  75                  80

Asp Gly Phe Leu Phe Asn Val Pro Gly Ser Asp Gly Ile Leu Gly Ser
                85                  90                  95

Pro Leu Cys Leu Ile Gln Val Thr Arg Leu Ser Cys Gly Gly Phe Ile
            100                 105                 110

Phe Ala Leu Arg Leu Asn His Thr Ile Cys Asp Ala Leu Gly Leu Val
        115                 120                 125

Gln Phe Leu Asn Ala Val Gly Glu Ile Ala Gln Gly Lys Tyr Ala Pro
    130                 135                 140

Ser Ile Thr Pro Val Trp Glu Arg Glu Leu Leu Ser Ala Arg Asp Pro
145                 150                 155                 160

```
Pro Arg Ile Ser Cys Thr His Glu Glu Phe Asp Asp Ser Ile Asp His
                165                 170                 175

Ser Tyr Pro Asn Tyr Gly Ala Thr Val Gln Gln Cys Tyr Cys Phe Gly
            180                 185                 190

Pro Lys Glu Ile Lys Ser Leu Arg Glu His Leu Pro Pro His Leu Ser
        195                 200                 205

Thr Cys Ser Ser Thr Phe Glu Leu Ile Thr Ala Cys Val Trp Lys Cys
    210                 215                 220

Arg Thr Ile Ser Leu Asp Met Asp Pro Glu Gln Ile Val Arg Leu Ser
225                 230                 235                 240

Cys Val Val Thr Ala Leu Gly Lys His Asn Asn Val Cys Leu Pro Leu
                245                 250                 255

Gly Tyr Tyr Gly Asn Thr Phe Thr Tyr Pro Ala Val Val Ser Thr Ala
            260                 265                 270

Glu Arg Leu Cys Asn Ser Pro Leu Gly Tyr Ala Val Glu Leu Val Lys
        275                 280                 285

Lys Ser Lys Ala Lys Met Ser Glu Glu Tyr Leu Arg Ser Ala Ile Asp
    290                 295                 300

Phe Val Glu Val Arg Gly Arg Pro Pro Phe Ala Leu Glu Gly Met Ser
305                 310                 315                 320

Asp Phe Leu Val Ser Asp Asn Thr Arg Thr Gly Leu Gly Glu Ile Asp
                325                 330                 335

Phe Gly Phe Gly Lys Pro Val Tyr Ala Gly Val Ala Lys Ser Thr Asp
            340                 345                 350

Leu Ile Ser Phe Tyr Val Arg Ser Thr Asn Lys Glu Glu Arg Glu Ile
        355                 360                 365

Leu Val Pro Val Cys Leu Pro Ile Leu Ser Met Glu Ile Phe Gln Gln
370                 375                 380

Glu Leu Lys Lys Met Ile Gly
385                 390

<210> SEQ ID NO 24
<211> LENGTH: 1176
<212> TYPE: DNA
<213> ORGANISM: Artificial Sequence
<220> FEATURE:
<223> OTHER INFORMATION: Yarrowia codon-optimized FaATF

<400> SEQUENCE: 24
atgtcttaca agaacaacca ctctattctg tctaagccta cgaccctgt cgaggtgatt      60 cgagatgccc tgtccaaggc ccttcagttt tactaccctc tcgctggacg actccgagag    120
ggtcccaaca agaagctcat ggtggactgc actggtgagg gaatcctctt tgttgaggct    180
aacgctgagg tcactctcga tgagctcggc gatgctatcc ttccccttg tccttttctt    240 gacggtttc tctttaacgt gcccggttct gacggtattc ttggttctcc tctctgtctt    300
attcaggtca ctcgactctc ttgtggaggt tttattttg ctctgcgact taaccacact    360
atttgcgatg ctctgggtct tgttcagttt ctcaacgctg ttggcgagat tgcccaggga    420
aagtacgctc cttctattac ccctgtttgg gagcgagagc tcctctctgc ccgagaccct    480
ccccgaattt cctgtactca cgaggagttt gacgattcta ttgaccactc ttaccctaac    540
tacggtgcta ccgttcagca gtgttactgt tttggtccca aggagatcaa gtcccttcga    600
gagcaccttc cccctcacct ttctacttgt tcttccactt tcgagcttat tactgcttgt    660
gtgtggaagt gccgaactat ctctctcgat atggaccctg agcagattgt ccgactctct    720
```

```
tgcgttgtta ctgctcttgg taagcacaac aacgtttgtc tccctctcgg atactacgga    780
aacactttca cttaccctgc tgttgtttct actgccgagc gactttgtaa ctctcccctg    840
ggttacgctg tggagcttgt caagaagtcc aaggctaaga tgtctgagga gtaccttcga    900
tctgctattg actttgtcga ggttcgagga cgaccccct ttgctcttga gggtatgtct     960
gacttccttg tttccgataa cactcgaact ggtcttggtg agattgactt tggcttcgga   1020
aagcctgttt acgctggagt tgccaagtcc accgatctca tctccttta cgtccgatcc    1080 actaacaagg aggagcgaga gattcttgtc cctgtttgcc ttcccattct gtctatggag   1140 attttcagc aggagctcaa gaagatgatt ggttaa                              1176
```

<210> SEQ ID NO 25
<211> LENGTH: 219
<212> TYPE: PRT
<213> ORGANISM: Escherichia coli

<400> SEQUENCE: 25

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

<210> SEQ ID NO 26
<211> LENGTH: 660
<212> TYPE: DNA
<213> ORGANISM: Artificial Sequence
<220> FEATURE:
<223> OTHER INFORMATION: Yarrowia codon-optimized EcCAT

<400> SEQUENCE: 26

```
atggagaaga agattactgg ttacaccact gtcgatattt ctcagtggca ccgaaaggag     60
cactttgagg cttttcagtc tgttgctcag tgtacttaca accagaccgt tcagctcgat    120
```

-continued

```
attaccgctt tccttaagac tgtcaagaag aacaagcaca agttttaccc tgcctttatt      180
cacattcttg cccgactgat gaacgctcac cctgagttcc gaatggctat gaaggatggt      240
gagctcgtga tttgggattc tgttcaccct tgttacaccg ttttcacga gcagactgag       300 actttctctt ccctctggtc tgagtaccac gatgacttcc gacagttcct tcacatttac      360
tctcaggatg tcgcctgtta cggtgagaac ctggcttact tccctaaggg ttttattgag      420
aacatgtttt tcgtgtctgc taaccctgg gtttccttca cctcttttga ccttaacgtg       480
gctaacatgg acaacttctt cgcccccgtt ttcactatgg aaagtacta cactcagggc      540 gacaaggtgc tcatgcccct ggccattcag gttcaccacg ctgtctgtga tggctttcac      600
gtcggtcgaa tgcttaacga gcttcagcag tactgcgatg agtggcaggg cggcgcttag      660
```

<210> SEQ ID NO 27
<211> LENGTH: 363
<212> TYPE: PRT
<213> ORGANISM: Euonymus alatus

<400> SEQUENCE: 27

```
Met Met Asp Ala His Gln Glu Ile Lys Asn Phe Ile Lys Val Trp Val
1               5                   10                  15

Gln Ala Met Val Cys Leu Ser Tyr Ala Tyr Tyr Phe Ser Ser Arg Leu
                20                  25                  30

Pro Lys Gly Leu Leu Arg Leu Leu Ser Leu Pro Val Leu Tyr Leu
        35                  40                  45

Leu Leu Ile Ala Pro Leu Asn Ile Ser Ser Phe Ile Leu Ser Ser Ile
    50                  55                  60

Thr Gly Phe Phe Leu Ala Trp Leu Thr Thr Phe Lys Val Ile Ser Phe
65                  70                  75                  80

Ala Phe Asp Gln Gly Pro Leu Tyr Pro Leu Pro Gln Asn Leu Leu His
                85                  90                  95

Phe Ile Ser Ile Ala Cys Leu Pro Ile Thr Ile Lys Arg Asn Pro Ser
            100                 105                 110

Pro Lys Leu Lys Ser Thr Thr Asn Pro Ser Pro Ile Ser His Leu Leu
        115                 120                 125

Lys Lys Ala Phe Met Ser Phe Pro Ser Lys Val Leu Phe His Trp Val
    130                 135                 140

Ile Ala His Leu Tyr Gln Tyr Lys Lys Tyr Met Asp Pro Asn Val Val
145                 150                 155                 160

Leu Val Ile Tyr Cys Cys His Val Tyr Val Met Leu Asp Ile Ser Leu
                165                 170                 175

Ser Leu Cys Ala Thr Leu Ala Glu Phe Leu Cys Gly Phe Asp Val Glu
            180                 185                 190

Pro Gln Phe Lys Glu Pro Tyr Leu Ala Thr Ser Leu Gln Asp Phe Trp
        195                 200                 205

Gly Arg Arg Trp Asn Ile Ile Val Ser Ser Val Leu Arg Ser Thr Val
    210                 215                 220

Tyr Ala Pro Thr Arg Asn Ile Ala Ser Tyr Leu Ile Gly Ser Arg Trp
225                 230                 235                 240

Ala Tyr Phe Pro Ala Ile Ile Ala Thr Phe Val Val Ser Gly Val Met
                245                 250                 255

His Asp Val Val Tyr Tyr Val Tyr Met Met His Met Tyr Pro Lys Trp
            260                 265                 270

Asp Met Thr Gly His Phe Val Leu His Gly Ile Cys Glu Ala Leu Glu
        275                 280                 285
```

```
Val Glu Met Lys Cys Lys Arg Ser Arg Ser Asp Lys Trp Arg Arg His
    290                 295                 300
Pro Ala Val Asp Trp Val Met Val Met Gly Phe Val Met Gly Thr Ser
305                 310                 315                 320
Val Ser Leu Leu Phe Val Pro Leu Leu Arg Asp Asn Val Asp Gln Ile
                325                 330                 335
Val Ala Glu Glu Tyr Ser Ile Leu Phe Asn Phe Val Arg Glu Lys Ile
                340                 345                 350
Val Met Leu Gly Thr Arg Phe Val Cys Gly Asn
                355                 360

<210> SEQ ID NO 28
<211> LENGTH: 1092
<212> TYPE: DNA
<213> ORGANISM: Artificial Sequence
<220> FEATURE:
<223> OTHER INFORMATION: Yarrowia codon-optimized EaCAcT

<400> SEQUENCE: 28
atgatggatg ctcaccagga gatcaagaac ttcatcaagg tttgggtgca ggctatggtg      60
tgtctttctt acgcttacta cttctcctct cgacttccca agggactcct tcgacttctc     120
tctcttctcc ctgttcttta ccttctcctt atcgctcccc ttaacatttc ctctttcatt     180
ctttcttcta tcaccggctt cttccttgct tggcttacca ctttcaaggt catctctttt     240
gctttcgatc agggtcctct ctaccctctc cctcagaacc tccttcactt catttccatt     300
gcttgtctcc ctatcactat caagcgaaac ccctctccta agctcaagtc caccactaac     360
ccttctccta tttctcacct tctcaagaag gcttttatgt cttttccctc taaggttctt     420
ttccactggg tcattgctca cctttaccag tacaagaagt acatggaccc taacgtggtc     480
ctcgttatct actgttgtca cgtttacgtt atgcttgaca tttctctctc tctgtgtgct     540
accctggctg agtttctctg tggttttgac gttgagcctc agtttaagga gccttacctt     600
gctacttctc ttcaggactt tggggccga cgatggaaca ttattgtctc ttctgtcctg     660
cgatccactg tttacgctcc cactcgaaac attgcttctt accttattgg atctcgatgg     720
gcttactttc ccgctattat tgctactttc gttgtgtctg gagttatgca cgatgtcgtg     780
tactacgttt acatgatgca catgtacccc aagtgggata tgactggtca cttcgtcctt     840
cacggaattt gtgaggctct ggaggtggag atgaagtgta agcgatctcg atctgacaag     900
tggcgacgac accctgctgt cgattgggtg atggtgatgg ttttgtcat gggtacttct     960 gtttccctcc ttttcgtccc ctctccttcga gataacgtcg atcagattgt tgctgaggag    1020
tactctattc tctttaactt tgttcgagag aagattgtca tgcttggtac tcgatttgtc    1080
tgtggaaact aa                                                        1092

<210> SEQ ID NO 29
<211> LENGTH: 459
<212> TYPE: PRT
<213> ORGANISM: Malus domestica

<400> SEQUENCE: 29

Met Met Pro Phe Ser Val Leu Gln Val Lys Arg Leu Gln Leu Glu Leu
1               5                   10                  15
Ile Thr Pro Ala Lys Pro Thr Leu Gln Glu Ala Lys Phe Leu Ser Asp
                20                  25                  30
Ile Asp Asp Gln Glu Gly Leu Arg Phe Gln Val Pro Val Ile Met Cys
                35                  40                  45
```

```
Tyr Lys Asp Asn Pro Ser Leu Asn Lys Asn Cys Asn Pro Val Lys Val
 50                  55                  60

Ile Arg Glu Ala Leu Ser Arg Ala Leu Val Tyr Tyr Pro Leu Ala
 65                  70                  75                  80

Gly Arg Leu Lys Glu Gly Pro Asn Arg Lys Leu Met Val Asp Cys Asn
                 85                  90                  95

Gly Glu Gly Ile Leu Phe Val Glu Ala Ser Ala Asp Val Thr Leu Glu
                100                 105                 110

Gln Leu Gly Asp Lys Ile Leu Pro Pro Cys Pro Leu Leu Glu Glu Phe
                115                 120                 125

Leu Phe Asn Phe Pro Gly Ser Asp Gly Ile Ile Gly Cys Pro Leu Leu
130                 135                 140

Leu Val Gln Val Thr Cys Leu Thr Cys Gly Gly Phe Ile Leu Ala Leu
145                 150                 155                 160

Arg Val Asn His Thr Met Cys Asp Ala Pro Gly Leu Leu Leu Phe Leu
                165                 170                 175

Thr Ala Ile Ala Glu Met Ala Arg Gly Ala His Ala Pro Ser Ile Leu
                180                 185                 190

Pro Val Trp Glu Arg Glu Leu Leu Phe Ser Arg Asp Pro Pro Arg Ile
                195                 200                 205

Thr Cys Ala His His Glu Tyr Glu Asp Val Ile Asp His Ser Asp Gly
210                 215                 220

Leu Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
                260                 265                 270

Lys Cys Arg Thr Leu Ala Leu Asn Ile Asn Pro Lys Glu Ala Val Arg
                275                 280                 285

Val Ser Cys Ile Val Asn Ala Arg Gly Lys His Asn Asn Val Arg Leu
                290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
                340                 345                 350

Ala Asp Leu Leu Val Leu Arg Gly Arg Pro Gln Tyr Ser Ser Thr Gly
                355                 360                 365

Ser Tyr Leu Ile Val Ser Asp Asn Thr Arg Ala Gly Phe Gly Asp Val
                370                 375                 380

Asn Phe Gly Trp Gly Gln Pro Val Phe Ala Gly Pro Ala Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
                420                 425                 430

Gln Glu Leu Glu Arg Ile Thr Gln Glu Pro Lys Glu Asp Ile Cys Asn
                435                 440                 445

Asn Leu Arg Ser Thr Arg Ile Met Ser Met Met
450                 455
```

<210> SEQ ID NO 30
<211> LENGTH: 1380
<212> TYPE: DNA
<213> ORGANISM: Artificial Sequence
<220> FEATURE:
<223> OTHER INFORMATION: Yarrowia codon-optimized MdATF

<400> SEQUENCE: 30

```
atgatgccct ctctgttct ccaggttaag cgacttcagc ttgagcttat taccctgcc      60
aagcccactc tccaggaggc taagtttctc tctgacatcg acgatcagga gggccttcga    120
tttcaggttc ctgtcattat gtgttacaag ataacccttc tcttaacaa gaactgtaac    180
cctgttaagg tgattcgaga ggctctttcc gagctcttg tttactacta ccctctcgct    240
ggacgactta aggagggtcc taaccgaaag ctcatggtcg attgcaacgg tgagggtatt    300
ctgttcgttg aggcttctgc tgatgttacc cttgagcagc ttggtgataa gattcttccc    360
ccttgtcctc tccttgagga gttccttttc aactttcccg gttctgatgg tattattggt    420
tgtcctctcc ttctcgttca ggtcacttgc cttacctgtg gaggctttat tcttgccctt    480
cgagtcaacc acactatgtg tgatgctcct ggtctgctcc tgttcctgac cgccatcgct    540
gagatggccc gaggagctca cgctccttct attcttcccg tttgggagcg agagcttctc    600
ttttcccgag atccccctcg aattacttgt gctcaccacg agtacgagga cgttattgac    660
cactctgacg tctttacgc ttcttccaac cagtctaaca tggttcagcg atctttctac    720
tttggtgcca aggagatgcg agttcttcga aagcagattc ctccccacct tatttctacc    780
tgctctacct ttgacctat taccgcttgt ctttggaagt gtcgaacct gctcttaac     840
attaacccta aggaggctgt tcgagttct tgcattgtta acgcccgagg aaagcacaac    900
aacgttcgac tccccttgg ttactacgga aacgcttttg cttttcccgc tgctatctct    960
aaggccgagc ctctctgtaa gaacccctt ggttacgctc ttgagcttgt caagaaggct   1020
aaggctacta tgaacgagga gtaccttcga tctgtggctg atctccttgt tcttcgagga   1080
cgacctcagt actcttctac cggatcttac cttattgttt ctgataacac ccgagctggt   1140
tttggtgatg ttaactttgg ttggggacag cccgtttttg ctggacccgc caaggccctt   1200
gaccttatt cctctacgt tcagcacaag aacaacactg aggatggtat tcttgttcct   1260
atgtgtctcc cttcctccgc tatggagcga tttcagcagg agcttgagcg aattactcag   1320
gagcctaagg aggatatttg taacaaccctt cgatctactc gaatcatgtc tatgatgtaa   1380
```

<210> SEQ ID NO 31
<211> LENGTH: 465
<212> TYPE: PRT
<213> ORGANISM: Petunia x hybrida

<400> SEQUENCE: 31

```
Met Cys Pro Lys Leu Ala Arg Ile Asn Ser Tyr Met Gly Asn Thr Asp
1               5                   10                  15

Phe His Val Thr Val Lys Lys Lys Glu Val Val Ala Ala Val Leu Pro
            20                  25                  30

Met His His Glu His Trp Leu Pro Met Ser Asn Leu Asp Leu Leu Leu
        35                  40                  45

Pro Pro Leu Asp Phe Gly Val Phe Phe Cys Tyr Lys Arg Ser Lys Ile
    50                  55                  60

Asn Asn Asp Thr Lys Asp Asp Asp Glu Thr Ile Lys Lys Ala Leu Ala
65                  70                  75                  80
```

-continued

```
Glu Thr Leu Val Ser Phe Tyr Ala Leu Ala Gly Glu Val Val Phe Asn
                85                  90                  95

Ser Leu Gly Glu Pro Glu Leu Leu Cys Asn Asn Arg Gly Val Asp Phe
            100                 105                 110

Phe His Ala Tyr Ala Asp Ile Glu Leu Asn Asn Leu Asp Leu Tyr His
        115                 120                 125

Pro Asp Val Ser Val His Glu Lys Leu Ile Pro Ile Lys Lys His Gly
    130                 135                 140

Val Leu Ser Val Gln Val Thr Gly Leu Lys Cys Gly Gly Ile Val Val
145                 150                 155                 160

Gly Cys Thr Phe Asp His Arg Val Ala Asp Ala Tyr Ser Ala Asn Met
                165                 170                 175

Phe Leu Val Ala Trp Ala Ala Ile Ala Arg Lys Asp Asn Asn Ile Asn
            180                 185                 190

Thr Val Ile Pro Ser Phe Arg Arg Ser Leu Leu Asn Pro Arg Arg Pro
        195                 200                 205

Pro Gln Phe Asp Asp Ser Phe Ile Asp Ser Thr Tyr Val Phe Leu Ser
    210                 215                 220

Ser Pro Pro Lys Gln Pro Asn Asp Val Leu Thr Ser Arg Val Tyr Tyr
225                 230                 235                 240

Ile Asn Ser Gln Glu Ile Asn Leu Leu Gln Ser Gln Ala Thr Arg Asn
                245                 250                 255

Gly Ser Lys Arg Ser Lys Leu Glu Cys Phe Ser Ala Phe Leu Trp Lys
            260                 265                 270

Thr Ile Ala Glu Gly Gly Ile Asp Asp Ser Lys Arg Cys Lys Leu Gly
        275                 280                 285

Ile Val Val Asp Gly Arg Gln Arg Leu Arg His Asp Ser Ser Thr Thr
    290                 295                 300

Met Lys Asn Tyr Phe Gly Asn Val Leu Ser Val Pro Tyr Thr Glu Ala
305                 310                 315                 320

Ser Val Gly Gln Leu Lys Gln Thr Pro Leu Gly Lys Val Ala Asp Leu
                325                 330                 335

Val His Thr Cys Leu Asp Asn Val Ala Asn Glu His His Phe Pro Ser
            340                 345                 350

Leu Ile Asp Trp Val Glu Leu His Arg Pro Arg Gln Ala Ile Val Lys
        355                 360                 365

Val Tyr Cys Lys Asp Glu Cys Asn Asp Glu Ala Ala Ile Val Val Ser
    370                 375                 380

Ser Gly Leu Arg Phe Pro Leu Ser Gln Val Asn Phe Gly Trp Gly Cys
385                 390                 395                 400

Pro Asp Phe Gly Ser Tyr Ile Phe Pro Trp Gly Gln Thr Gly Tyr
                405                 410                 415

Val Met Pro Met Pro Ser Pro Asn Lys Asn Gly Asp Trp Ile Val Tyr
            420                 425                 430

Met His Leu Gln Lys Lys His Leu Asp Leu Val Glu Thr Arg Ala Pro
        435                 440                 445

His Ile Phe His Pro Leu Thr Ala Cys Tyr Leu Asp Leu Thr Ala Thr
    450                 455                 460

Tyr
465
```

```
<210> SEQ ID NO 32
<211> LENGTH: 1398
<212> TYPE: DNA
<213> ORGANISM: Artificial Sequence
<220> FEATURE:
<223> OTHER INFORMATION: Yarrowia codon-optimized PhATF

<400> SEQUENCE: 32
atgtgcccta agctcgctcg aattaactct tacatgggaa acactgactt tcacgttacc      60
gtcaagaaga aggaggttgt ggctgctgtt ctccctatgc accacgagca ctggcttccc     120
atgtccaacc ttgaccttct ccttcccccct ctcgactttg gtgttttctt ctgctacaag    180
cgatctaaga ttaacaacga taccaaggat gacgatgaga ctattaagaa ggctcttgct     240
gagactctcg tttcttttta cgctcttgct ggagaggtgg ttttcaactc tctcggagag     300
cccgagcttc tctgtaacaa ccgaggagtt gatttctttc acgcttacgc tgatattgag     360
ctcaacaacc ttgacctttta ccaccccgat gtctctgttc acgagaagct gattcctatc    420
aagaagcacg gcgttctctc tgttcaggtc actggcctta gtgtggagg tatcgttgtt       480
ggatgcactt tcgatcaccg agttgctgat gcttactctg ctaacatgtt ccttgttgct     540
tgggctgcta ttgctcgaaa ggataacaac attaacactg ttatccttc tttccgacga     600
tccctcctta accctcgacg acctcccag tttgacgatt cctttatcga ctccacctac     660
gttttccttt cttctccccc taagcagcct aacgatgtcc tcacttcccg agtgtactac     720
attaactctc aggagattaa cctccttcag tctcaggcta ctcgaaacgg atctaagcga    780
tctaagctgg agtgtttctc cgcctttctc tggaagacta ttgctgaggg aggtattgac    840
gattctaagc gatgtaagct cggaattgtt gtcgatggcc gacagcgact gcgacacgac    900
tcttctacca ccatgaagaa ctactttggc aacgttcttt ctgttccttca cactgaggct    960
tctgttggac agctcaagca gactcccctt ggtaaggttg ctgaccttgt tcacacttgc   1020
ctcgataacg ttgctaacga gcaccacttt ccctctctca ttgactgggt tgagcttcac   1080
cgacctcgac aggctattgt taaggtttac tgtaaggatg agtgtaacga tgaggctgcc   1140
atcgttgtct cctctggact ccgatttccc cttctcagg ttaactttgg ctggggctgt    1200
cctgactttg gctcttacat ttttcccttgg ggcggtcaga ctggttacgt gatgcctatg   1260
ccttctccca caagaacgg tgattggatt gtttacatgc accttcagaa gaagcacctt    1320
gaccttgtcg agactcgagc ccctcacatc ttccacccc ttaccgcttg ttacctcgat    1380
ctcactgcta cttactaa                                                1398

<210> SEQ ID NO 33
<211> LENGTH: 559
<212> TYPE: PRT
<213> ORGANISM: Lachancea mirantina

<400> SEQUENCE: 33

Met Gly Asp Leu Asp Ala Arg Gly Thr Ser Ala His Pro Glu Leu Ser
1               5                   10                  15

Glu Arg Pro Ser Ile Met Pro Ser Met Ser Asp Ile Gln Asp Pro Ser
            20                  25                  30

Gly Asp Asp Lys Ala Thr Pro Arg Gly Ser Ala Ala Gly Leu Pro Gln
        35                  40                  45

Leu Glu Leu Ala Gly His Ala Arg Arg Leu Gly His Leu Glu Asn Phe
    50                  55                  60

Phe Ala Val Gln His Arg Gln Gln Ile Tyr Ser Ser Phe Ala Val Phe
65                  70                  75                  80
```

```
Cys Glu Phe Asp Thr Ala Cys Ser Leu Ala Gln Leu Ala Ser Ala Val
                 85                  90                  95

Arg Asn Val Cys Leu Ser Asn Pro Leu Leu His Thr Val Glu Pro
            100                 105                 110

Lys His Pro Asp Ile Ala Gly Phe Tyr His Ser Asp Glu Tyr Leu Ser
        115                 120                 125

Arg Pro Trp Pro Gln His Asp Tyr Met Arg Val Leu Arg Glu Val His
    130                 135                 140

Val Ala Asp Val Val Met Asn Gly Gln Lys Glu His Ala His Val Val
145                 150                 155                 160

Arg Asp Ala Val Asp Val Phe Gln Ala His Gly Asn Gln Val Thr Ser
                165                 170                 175

Glu Leu Leu Glu Leu Met Thr Gln Ile Glu Ile Pro His Ala Ser Gln
            180                 185                 190

Thr Arg Pro Ser Trp Arg Leu Leu Cys Phe Pro His Gly Glu Ala Asn
        195                 200                 205

Arg Trp Arg Thr Phe Ala Phe Val Ser Asn His Cys Ser Ser Asp Gly
    210                 215                 220

Leu Ser Gly Leu Asn Phe Phe Arg Asp Leu Gln Lys Glu Leu Ala His
225                 230                 235                 240

Gly Pro Thr Ser Gly Ala Pro Gly Ala Pro Gly Ala Ser Gly Val Ile
                245                 250                 255

Phe Asp Tyr Ala Gln Asp Ala Ala Thr Leu Pro Lys Leu Pro Pro Pro
            260                 265                 270

Ile Asp Gln Lys Leu Asp Tyr Arg Pro Ser Lys Lys Ala Leu Leu Gly
        275                 280                 285

Leu Leu Ala Gly Lys Phe Val Arg Glu Lys Leu Gly Tyr Val Ser Ala
    290                 295                 300

Ala Pro Pro Thr Thr Pro Thr Ser Asp Leu Ala His Pro Glu Gly His
305                 310                 315                 320

Gln Tyr Tyr Cys Tyr Leu Val Asn Val Pro Thr Ser Ser Val Ala His
                325                 330                 335

Ile Lys Thr Gln Val Arg Glu Asn Val Pro His Lys Cys Thr Leu Thr
            340                 345                 350

Pro Phe Leu Gln Ala Cys Trp Leu Val Ser Leu Phe Lys Tyr Gly Arg
        355                 360                 365

Val Phe Ser Gly Ser Trp Leu Glu Arg Tyr Thr Asp Val Leu Val Ala
    370                 375                 380

Met Asn Thr Arg Gln Leu Leu Pro Glu Asp Leu Glu Leu Gln Arg Gln
385                 390                 395                 400

Tyr Arg Tyr Gly Ser Asn Val Gly Gly Val Arg Tyr Asn Tyr Pro Ile
                405                 410                 415

Ala Pro Leu Asp Val Arg Asp Asn Asp Gln Lys Phe Trp Ser Leu Val
            420                 425                 430

Glu Ser Tyr Arg Leu Ala Leu Ser Asp Ala Arg Asp Lys Asn Asp Tyr
        435                 440                 445

Leu Tyr Ala Leu Gly Ala Leu Met Leu Pro Glu Ile Tyr Glu Lys Lys
    450                 455                 460

Asn Val Asp Ala Val Val Asn Asp Thr Ile Leu Asn Gln Arg Arg Ser
465                 470                 475                 480

Gly Thr Leu Ile Ser Asn Val Gly Tyr Val Arg Asp Glu Gln Pro Thr
                485                 490                 495
```

```
Ala Phe Ala Ile Lys Asn His Val Phe Ser Gln Gly Val Gly Ala Asn
        500                 505                 510

Arg Asn Ala Phe Val Leu Asn Ile Cys Ala Thr Asp Gln Gly Gly Leu
        515                 520                 525

Asn Ile Ala Ile Ser Ile Ala Lys Gly Thr Leu Ala Ser Arg Gln Glu
        530                 535                 540

Gly Gln Glu Leu Cys Asp Ile Phe Lys Ser Thr Leu Leu Arg Phe
545                 550                 555

<210> SEQ ID NO 34
<211> LENGTH: 1680
<212> TYPE: DNA
<213> ORGANISM: Lachancea mirantina

<400> SEQUENCE: 34
```

| | | |
|---|---|---|
| atgggtgatc tcgacgcgag gggaacatca gcgcacccgg agctctcgga gaggccaagc | 60 |
| atcatgccct cgatgtcgga tatccaggac ccaagcggcg acgacaaggc cacgccccgc | 120 |
| ggctccgccg cggggctgcc gcagctcgag ctcgccggcc acgcccggcg cctgggccat | 180 |
| ttggagaatt tcttcgccgt ccagcaccgg cagcagatct attccagttt cgccgtgttc | 240 |
| tgcgagttcg acaccgcgtg ctcgctcgcg cagctcgcgt ccgctgtgcg aaacgtgtgt | 300 |
| ctttcgaacc cgctgctgct gcacaccgtc gagcccaagc accggacat cgccggcttc | 360 |
| taccactccg acgaatatct gtcccgaccc tggccccagc acgactacat gcgcgttttg | 420 |
| cgcgaggtcc acgtcgccga cgtggtgatg aacggccaga agagcacgc gcatgtcgtg | 480 |
| cgcgacgccg tcgacgtttt ccaagcgcat ggaaaccagg tcaccagcga gctgctcgag | 540 |
| ctcatgaccc agattgagat cccgcacgct cccaaacga gacccagctg gaggttgctg | 600 |
| tgtttcccac acggcgaggc caaccggtgg cgcacgtttg cgtttgtatc aatcattgt | 660 |
| tccagcgacg gtctctcggg tctgaacttc tttcgggacc tgcaaaagga gctcgcgcac | 720 |
| ggccccacct cggggccccc cggggccccg ggggcctccg gcgtcatctt cgactacgcc | 780 |
| caggacgccg caacactgcc caaactgccc ccacccattg accaaaaact cgattaccgt | 840 |
| ccgtccaaga aggccctttt gggacttttg gccggcaagt tcgtgcgtga aaaactcggc | 900 |
| tacgtatcgg ccgccccgcc aacgaccccg acctccgatt ggcgcacccc agaaggtcac | 960 |
| caatactact gctaccttgt aaacgtaccg acatctagtg tggcccacat caaaacgcaa | 1020 |
| gtgcgcgaaa atgtcccgca caatgcacg ctgacgccat tcttacaggc atgctggctc | 1080 |
| gtgtcactgt tcaagtatgg tcgcgttttt tccggctcct ggctcgaacg atacacggac | 1140 |
| gttctcgtcg ctatgaacac ccggcaactg ttgcccgaag atttggaatt gcaacgccag | 1200 |
| taccgttacg gtagtaacgt gggagggta cgttacaatt atccaatcgc accgctcgac | 1260 |
| gtccgcgaca acgaccagaa attctggtcc ctggtggaga gttaccgact ggcccttagc | 1320 |
| gacgcacgcg acaaaaatga ttacttgtac gcattgggtg ctctaatgct tccagagatc | 1380 |
| tacgaaaaaa aaaacgtcga tgctgtggtc aatgacacaa ttctgaacca gcgtcgttcc | 1440 |
| ggaacgttga tcagtaacgt cggctacgtg cgcgatgaac agcccactgc gtttgcaatt | 1500 |
| aagaatcatg tcttttcaca aggcgttggc gccaacagaa acgcatttgt gcttaacata | 1560 |
| tgtgccacgg accaaggcgg cctaaatatc gccatcagta tcgccaaggg aaccttggcg | 1620 |
| tctcgtcaag aaggccaaga actttgcgac atctttaaat caacgttact gcgattctaa | 1680 |

<210> SEQ ID NO 35
<211> LENGTH: 1680
<212> TYPE: DNA
<213> ORGANISM: Artificial Sequence
<220> FEATURE:
<223> OTHER INFORMATION: Yarrowia codon optimized LmATF1

<400> SEQUENCE: 35

| | | | | | |
|---|---|---|---|---|---|
| atgggtgatc | tcgatgcccg | aggaacctct | gctcaccccg | agctctctga | gcgaccttct | 60 |
| attatgcctt | ctatgtctga | tattcaggac | ccttctggtg | atgacaaggc | tactccccga | 120 |
| ggatctgctg | ctgggctgcc | ccagcttgag | cttgctggac | acgcccgacg | acttggccac | 180 |
| cttgagaact | tctttgctgt | ccagcaccga | cagcagattt | actcttcttt | tgctgttttt | 240 |
| tgtgagtttg | acactgcttg | ttctctcgct | cagcttgctt | ctgctgtgcg | aaacgtttgt | 300 |
| cttttctaacc | cccttctcct | tcacactgtt | gagcctaagc | ccctgacat | cgctggattc | 360 |
| taccactctg | acgagtacct | tcccgacct | tggcctcagc | acgattacat | gcgagttctt | 420 |
| cgagaggttc | acgtcgctga | cgttgttatg | aacggacaga | aggagcacgc | tcacgttgtt | 480 |
| cgagatgctg | ttgacgtttt | tcaggctcac | ggaaaccagg | ttacttctga | gctccttgag | 540 |
| cttatgactc | agattgagat | tcctcacgct | tctcagactc | gaccctcttg | gcgacttctc | 600 |
| tgttttcccc | acggagaggc | taaccgatgg | cgaacctttg | cttttgtttc | taaccactgt | 660 |
| tcttctgatg | gtctttctgg | tcttaacttc | tttcgagatc | tccagaagga | gcttgctcac | 720 |
| ggccccacct | ctggtgctcc | tggtgccccc | ggagcttccg | gagttatttt | cgattacgct | 780 |
| caggacgctg | ctaccctgcc | caagctgccc | cctcccattg | atcagaagct | cgattaccga | 840 |
| ccttctaaga | aggctcttct | cggccttctc | gctggcaagt | tcgttcgaga | aagctcggt | 900 |
| tacgtttctg | ctgctcctcc | cactacccct | acctctgacc | ttgctcaccc | tgagggtcac | 960 |
| cagtactact | gttaccttgt | taacgttccc | acttcttctg | ttgcccacat | taagactcag | 1020 |
| gtgcgagaga | acgttcctca | aagtgtact | ctcactcct | ttctccaggc | ttgttggctt | 1080 |
| gtttctctgt | tcaagtacgg | tcgagttttt | tctggttctt | ggcttgagcg | atacaccgat | 1140 |
| gttcttgttg | ctatgaacac | tcgacagctt | ctccccgagg | accttgagct | tcagcgacag | 1200 |
| taccgatacg | gttctaacgt | tggaggtgtt | cgatacaact | accctattgc | tccccttgac | 1260 |
| gttcgagata | acgatcagaa | gttctggtcc | cttgttgagt | cttaccgact | gcccctttct | 1320 |
| gatgcccgag | ataagaacga | ttacctttac | gctcttggtg | ctcttatgct | ccctgagatt | 1380 |
| tacgagaaga | agaacgttga | tgctgttgtt | aacgatacca | ttcttaacca | gcgacgatct | 1440 |
| ggaacccta | tttctaacgt | tggttacgtt | cgagatgagc | agcccactgc | ttttgctatt | 1500 |
| aagaaccacg | ttttttctca | gggagttgga | gctaaccgaa | acgcttttgt | tcttaacatt | 1560 |
| tgtgctaccg | atcagggtgg | tcttaacatc | gctatttcta | ttgctaaggg | aacccttgct | 1620 |
| tctcgacagg | agggacagga | gctttgtgat | attttaagt | ctactctcct | tcgatttaa | 1680 |

<210> SEQ ID NO 36
<211> LENGTH: 536
<212> TYPE: PRT
<213> ORGANISM: Lachancea fermentata

<400> SEQUENCE: 36

Met Ile Ile Ile Leu Thr Lys Pro Lys Phe Pro Ser Ser Asn Ser Arg
1               5                   10                  15

Ser Leu Glu Ile Lys Leu Asn Asn Met Pro Pro Gly Thr Leu Leu Arg
            20                  25                  30

```
Glu Met Ile Glu Asn Gly His Ala Arg Pro Met Gly Ser Ile Glu Asn
             35                  40                  45
Ile Tyr Gly Ile Phe Asn Arg Gln Lys Leu Tyr Arg Asn Phe Ser Met
 50                  55                  60
Phe Ala Glu Ile Asn Asp Phe Cys Asn Glu Arg Gln Leu Arg Ala Ala
 65                  70                  75                  80
Leu Arg Asn Leu Cys Leu Lys Asn Pro Ile Leu His Thr Ile Val
                 85                  90                  95
Pro Glu Ile Trp Pro Phe Asn Glu Lys Tyr Tyr Leu Ser Asp Glu Tyr
                100                 105                 110
Tyr Cys Met Pro Arg Ser Gln His Glu Phe Ile Ala Ile Leu Pro Glu
            115                 120                 125
Leu Asp Leu Ser Asp Ile Leu Ala Asn Lys Gln Thr Gln Tyr Gln Gln
130                 135                 140
Val Leu Glu Lys Ala Phe Arg Glu Phe Glu Ser Ser Asn Phe Cys Tyr
145                 150                 155                 160
Thr Ser Glu Val Tyr Lys Leu Ile Ala Thr Ile Ser Ile Pro Tyr Val
                165                 170                 175
Gly Pro Ser Trp Arg Leu Ile Cys Leu Pro Glu Lys Arg Gly Thr Glu
            180                 185                 190
Trp Arg Lys Phe Ile Phe Ile Ser Asn His Cys Leu Cys Asp Gly Arg
            195                 200                 205
Ser Ala Ala Asn Phe Phe His Asp Leu Lys Glu Leu Asn Cys Asn
            210                 215                 220
Ile Asp Asn Arg Leu Thr Val Thr Thr Ile Phe Ser Tyr Glu Arg Asp
225                 230                 235                 240
His Tyr Leu Leu Pro Lys Leu Pro Glu Pro Leu Glu Lys Arg Ile Asp
                245                 250                 255
Phe Arg Pro Pro Trp Ser Tyr Phe Pro Lys Tyr Leu Val Trp Glu Pro
            260                 265                 270
Ile Val Asn His Phe Lys Phe Ser Ser Asn Cys Ala Thr Ser Arg Leu
            275                 280                 285
Asp Glu Ser Phe Asp Gly Lys Thr Leu Leu Thr Glu Ile Ile Asn Ile
            290                 295                 300
Asp Val Gln Val Leu Glu Lys Val Arg Gln Leu Ile Lys Ala Asn Val
305                 310                 315                 320
His Glu Gly Gly Thr Ile Thr Pro Phe Leu Glu Ile Cys Trp Leu Ile
                325                 330                 335
Ser Leu His Lys Trp Gly Ala Phe Ser Gly Lys Ser Trp Thr Lys Cys
            340                 345                 350
Leu Thr Asp Val Phe Val Pro Val Asp Val Arg Asn Leu Leu Pro Asp
            355                 360                 365
Asp Asp Asp Ile Arg Lys Ser Tyr Arg Tyr Gly Cys Asn Val Ala Ala
            370                 375                 380
Ile Glu Leu Asn Pro Trp Ile Ser Gln Leu Asp Val Glu Lys Asn Ser
385                 390                 395                 400
Asp Glu Phe Trp Ala Leu Val Ser Gln Asn Gln Asn Lys Ile Thr Ser
                405                 410                 415
Leu Leu Gln Lys Lys Glu Gln Leu Asn Leu Ile Gly Phe Asn Thr Leu
            420                 425                 430
Asp Ile Val Glu Lys Asn Phe Asn Leu Asp Arg Glu Leu Cys Val His
            435                 440                 445
```

```
Thr Leu Asn Lys Pro Arg Gln Gly Thr Leu Leu Ser Asn Leu Gly Ile
    450                 455                 460

Phe Pro Gln Asn Ser Gln Glu Arg Asp Arg Tyr Ser Leu Glu Asn Leu
465                 470                 475                 480

Ile Phe Gly Gln Phe Gln Gly Ser Phe Arg Glu Ser Phe Ser Met Cys
                485                 490                 495

Val Cys Ser Thr Asp Arg Lys Gly Met Asn Ile Val Leu Thr Thr Thr
            500                 505                 510

Ser Asp Leu Ile Pro Asn Ser Lys Ser Trp Glu Asp Leu Cys Ser Thr
        515                 520                 525

Phe Lys Ser Ile Ile Ser Asp Thr
    530                 535

<210> SEQ ID NO 37
<211> LENGTH: 1611
<212> TYPE: DNA
<213> ORGANISM: Artificial Sequence
<220> FEATURE:
<223> OTHER INFORMATION: Yarrowia codon optimized LfATF1

<400> SEQUENCE: 37
```

| | | | | | |
|---|---|---|---|---|---|
| atgatcatta | ttctcactaa | gcctaagttc | ccttcctcca | actctcgatc | cctggagatc | 60 |
| aagctgaaca | acatgccccc | tggtactctc | ctgcgagaga | tgatcgagaa | cggacacgcc | 120 |
| cgacctatgg | gctccattga | gaacatttac | ggaattttta | accgacagaa | gctctaccga | 180 |
| aactttccta | tgtttgccga | gatcaacgac | ttttgtaacg | agcgacagct | tcgagccgcc | 240 |
| ctgcgaaacc | tgtgtcttaa | gaaccctatt | ctccttcaca | ccattgtccc | cgagatttgg | 300 |
| cctttcaacg | agaagtacta | cctgtctgac | gagtactact | gtatgcctcg | atctcagcac | 360 |
| gagtttatcg | ctattctgcc | cgagctcgac | ctgtccgata | ttctggccaa | caagcagacc | 420 |
| cagtaccagc | aggttctgga | gaaggctttc | cgagagttcg | agtcctccaa | cttttgttac | 480 |
| acctctgagg | tgtacaagct | gattgctact | atttctatcc | cttacgtggg | ccctcttgg | 540 |
| cgacttattt | gcctccctga | gaagcgagga | accgagtggc | gaaagttcat | cttcattccc | 600 |
| aaccactgtc | tctgtgatgg | tcgatccgcc | gccaactttt | tccacgacct | gaaggaggag | 660 |
| ctgaactgta | acattgacaa | ccgacttacc | gtcactacca | tttctctta | cgagcgagat | 720 |
| cactaccttc | tccccaagct | gcccgagccc | tggagaagc | gaattgattt | ccgacccct | 780 |
| tggtcttact | ttcccaagta | ccttgtctgg | gagcccatcg | tgaaccactt | caagttctcc | 840 |
| tctaactgcg | ctacttcccg | actcgatgag | tctttcgacg | gtaagactct | ccttaccgag | 900 |
| attattaaca | ttgacgtgca | ggtccttgag | aaggttcgac | agctcatcaa | ggccaacgtg | 960 |
| cacgagggtg | gtactatcac | cccttttcctt | gagatttgtt | ggctcatttc | ccttcacaag | 1020 |
| tggggagctt | tctctggtaa | gtcctggact | aagtgcctca | ccgatgtttt | tgttcccgtc | 1080 |
| gatgtccgaa | accttctccc | tgacgacgat | gacatccgaa | agtcttaccg | atacggctgt | 1140 |
| aacgttgctg | ctatcgagct | taaccccttgg | atctctcagc | tcgatgtcga | agaactcc | 1200 |
| gatgagtttt | gggccttgt | ttcccagaac | cagaacaaga | tcacctccct | cctccagaag | 1260 |
| aaggagcagc | tcaacctcat | tggctttaac | accctcgata | ttgtcgagaa | gaactttaac | 1320 |
| ctcgaccgag | agctctgcgt | ccacactctc | aacaagcccc | gacagggtac | tctcctgtcc | 1380 |
| aacctgggta | tttttccctca | gaactcccag | gagcgagatc | gatactccct | ggagaacctg | 1440 |
| attttggtc | agtttcaggg | ttccttccga | gagtcttttct | ctatgtgtgt | ctgttccacc | 1500 |

```
gatcgaaagg gaatgaacat tgttctcacc actacctctg atctcatccc caactccaag    1560
tcctgggagg acctttgctc taccttcaag tctattatct ccgacactta g             1611
```

<210> SEQ ID NO 38
<211> LENGTH: 515
<212> TYPE: PRT
<213> ORGANISM: Lachancea fermentata

<400> SEQUENCE: 38

```
Met Tyr Glu Ser Leu Gln Thr Leu Ile Glu Arg Gly His Ala Arg Arg
1               5                   10                  15

Leu Gly His Val Glu Asn Tyr Phe Val Leu Ala Gln Arg Gln Asp Leu
            20                  25                  30

Tyr Arg Val Phe Ala Tyr Tyr Gly Glu Phe Gly Glu Pro Cys Ser Leu
        35                  40                  45

Arg Gln Leu Thr Gln Ala Leu Arg Ser Met Cys Leu Gln Gln Pro Val
    50                  55                  60

Leu Leu Cys Gln Val Lys Pro Gln Glu Arg Pro Asp Leu Glu Leu Tyr
65                  70                  75                  80

Tyr Arg Ser Glu Glu Tyr Leu Ser Thr Pro Gly Gln Asp Arg Asp Tyr
                85                  90                  95

Ile Ala Leu Ala Asn Lys Val Arg Ile Ser Asp Val Leu Ile Asn Asn
            100                 105                 110

Gln Thr Glu Tyr Ala Glu Val Met His Lys Val Met Glu Glu Tyr Glu
        115                 120                 125

Ala Asn Gly His Asn Phe Thr Ser Lys Ile Phe Glu Ile Leu Ala Pro
    130                 135                 140

Ile Arg Ile Ser His Thr Asp Pro Asn Lys Leu Asn Trp Arg Leu Leu
145                 150                 155                 160

Ala Leu Pro Gly Glu Ile Pro Gly Glu Trp Asn Lys Phe Val Phe Leu
                165                 170                 175

Ser Asn His Ile Leu Lys Asp Gly Ser Ser Gly Ala His Phe Phe Ile
            180                 185                 190

Asp Leu Lys Asp Ser Leu Asn Ser Leu Pro Ser Asp Leu Gln Asp Thr
        195                 200                 205

Asp Arg Ile Phe Asp Tyr Lys Ser Asp Tyr Lys Phe Val Lys Glu Ile
    210                 215                 220

Pro Val Pro Ile Asp Glu Val Leu Asp Tyr Lys Pro Asn Leu Lys Gln
225                 230                 235                 240

Ile Ala Asn Val Phe Ser Thr Gln Leu Val Arg Glu Lys Leu Gly Tyr
                245                 250                 255

Leu Ser Pro Ala Pro Thr Ile Thr Arg Tyr Thr Asp Ala Glu Asn Asn
            260                 265                 270

Thr Asn Glu Tyr His Thr Cys Phe Ile Asn Phe Thr Pro Glu Glu Val
        275                 280                 285

Asp Ser Ile Lys Lys Lys Ile Lys Asp Arg Ala Gly Pro Ser Cys Thr
    290                 295                 300

Met Thr Pro Phe Leu Gln Ala Cys Trp Leu Val Ser Leu Tyr Lys Ser
305                 310                 315                 320

Gly Lys Val Phe Thr Lys Ser Phe Lys Glu Trp Phe Val Asp Met Met
                325                 330                 335

Ile Pro Met Tyr Thr Pro Gln Met Leu Ser Asp Gly Glu Gln Thr Arg
            340                 345                 350
```

```
Ala Asp Tyr Arg Tyr Gly Cys Asn Val Gly Gly Thr Arg Tyr Asn Tyr
        355                 360                 365

Leu Ile Ser Ser Leu Asn Val Gly Asn Asn Ser Lys Lys Phe Trp Lys
    370                 375                 380

Leu Val Ser Tyr Tyr Asn Asp Val Phe Arg Asp Ser Lys Ala Ser Asn
385                 390                 395                 400

Ser Tyr Leu Tyr Leu Ile Gly Met Ile Met Leu Asp Pro Ala Trp Lys
                405                 410                 415

Glu Lys Asn Leu Asp Ala Thr Val Leu Gln Asn Leu Leu Gly Arg His
            420                 425                 430

Arg Gln Gly Thr Val Leu Ser Asn Val Gly Phe Phe Ser Val Asn Gly
        435                 440                 445

Glu Pro Gln Asp Ala Phe His Leu Lys Asn Leu Leu Phe Thr Gln Thr
    450                 455                 460

Val Gly Ser Tyr Thr Phe Ala Phe Asn Leu Asn Val Cys Ser Thr Asp
465                 470                 475                 480

Val Ala Gly Met Asn Val Gly Ala Ser Val Ser Lys Gly Thr Leu Pro
                485                 490                 495

Thr Arg Asn Asp Trp Glu Glu Leu Cys Glu Ile Phe Lys Thr Thr Val
            500                 505                 510

Leu Gln Met
        515

<210> SEQ ID NO 39
<211> LENGTH: 1548
<212> TYPE: DNA
<213> ORGANISM: Artificial Sequence
<220> FEATURE:
<223> OTHER INFORMATION: Yarrowia codon optimized LffATF1

<400> SEQUENCE: 39
atgtacgagt cccttcagac tctcatcgag cgaggacacg ctcgacgact cggccacgtg     60
gagaactact ttgttctcgc tcagcgacag gatctctacc gagttttcgc ttactacgga    120
gagttcggag agccttgctc ccttcgacag ctcactcagg ccctccgatc tatgtgtctt    180
cagcagcctg ttctgctctg ccaggtcaag ccccaggagc gacctgacct cgagctttac    240
taccgatctg aggagtacct gtctactccc ggacaggatc gagattacat cgctcttgct    300
aacaaggtgc gaatctccga tgtccttatc aacaaccaga ctgagtacgc tgaggtcatg    360
cacaaggtta tggaggagta cgaggctaac ggccacaact ttacctctaa gattttttgag    420 attctcgccc ctattcgaat ctctcacacc gatcccaaca agctgaactg gcgactcctt    480
gctcttcccg gagagatccc tggtgagtgg aacaagtttg tcttcctttc aaccacatt    540 cttaaggatg gctcctctgg cgctcacttt ttcattgatc tcaaggattc tctgaactct    600
ctcccttctg acctccagga taccgaccga attttcgatt acaagtccga ctacaagttt    660
gttaaggaga tccccgtccc tatcgatgag gttcttgact acaagcctaa ccttaagcag    720
attgctaacg tcttttctac tcagcttgtt cgagagaagc tgggttacct ctctcctgct    780
cctaccatta ctcgatacac cgatgctgag aacaacacta cgagtacca cacttgcttt    840 attaacttta cccctgagga ggttgattct atcaagaaga agattaagga tcgagccggc    900
ccttcttgca ctatgacccc ttccttcag gcttgctggc tggttccct ttacaagtcc    960 ggcaaggttt tcactaagtc tttcaaggag tggttcgtgg acatgatgat ccctatgtac   1020 acccccaga tgctctctga cggcgagcag acccgagctg actaccgata cggctgtaac   1080
```

```
gttggaggta ctcgatacaa ctacctcatc tcctctctta acgttggaaa caactccaag    1140
aagttttgga agctggtttc ttactacaac gatgtcttcc gagactctaa ggcctccaac    1200
tcttaccttt accttatcgg aatgatcatg cttgaccctg cttggaagga gaagaacctg    1260
gacgccactg tccttcagaa cctccttggt cgacaccgac agggcactgt tctgtctaac    1320
gttggattct tttctgtgaa cggagagccc caggatgctt ttcaccttaa gaaccttctc    1380
tttacccaga ctgttggttc ttacaccttt gctttcaacc tcaacgtctg ctctactgac    1440
gtggccggaa tgaacgttgg cgcttctgtg tctaagggca ccctgcccac tcgaaacgac    1500
tgggaggagc tttgcgagat cttcaagact accgttctcc agatgtaa                1548

<210> SEQ ID NO 40
<211> LENGTH: 23
<212> TYPE: DNA
<213> ORGANISM: Artificial Sequence
<220> FEATURE:
<223> OTHER INFORMATION: primer MO11984

<400> SEQUENCE: 40
agtacataca gtcgtcgtag tgc                                              23

<210> SEQ ID NO 41
<211> LENGTH: 32
<212> TYPE: DNA
<213> ORGANISM: Artificial Sequence
<220> FEATURE:
<223> OTHER INFORMATION: primer MO11985

<400> SEQUENCE: 41
cacacggtct caccgttttt ctgggccttg ag                                    32

<210> SEQ ID NO 42
<211> LENGTH: 46
<212> TYPE: DNA
<213> ORGANISM: Artificial Sequence
<220> FEATURE:
<223> OTHER INFORMATION: primer MO11986

<400> SEQUENCE: 42
cacacggtct caacggcatt cctttattat ctggcttaca actaca                     46

<210> SEQ ID NO 43
<211> LENGTH: 38
<212> TYPE: DNA
<213> ORGANISM: Artificial Sequence
<220> FEATURE:
<223> OTHER INFORMATION: primer MO11987

<400> SEQUENCE: 43
cacacggtct cagtactact ccggtgacaa ggatttcc                              38
```